US010226331B2

(12) United States Patent
Lane et al.

(10) Patent No.: US 10,226,331 B2
(45) Date of Patent: *Mar. 12, 2019

(54) CONFORMABLE PROSTHESES FOR IMPLANTING TWO-PIECE HEART VALVES AND METHODS FOR USING THEM

(71) Applicant: Medtronic, Inc., Minneapolis, MN (US)

(72) Inventors: Ernest Lane, Huntington Beach, CA (US); Michael J. Drews, Sacramento, CA (US); Donnell W. Gurskis, Belmont, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/193,257

(22) Filed: Jun. 27, 2016

(65) Prior Publication Data

US 2016/0324631 A1    Nov. 10, 2016

Related U.S. Application Data

(63) Continuation of application No. 13/453,623, filed on Apr. 23, 2012, now Pat. No. 9,402,719, which is a (Continued)

(51) Int. Cl.
*A61F 2/24*      (2006.01)

(52) U.S. Cl.
CPC .......... *A61F 2/2409* (2013.01); *A61F 2/2412* (2013.01); *A61F 2/2418* (2013.01); (Continued)

(58) Field of Classification Search
CPC ..... A61F 2/2409; A61F 2/2418; A61F 2/2412
See application file for complete search history.

(56) References Cited

U.S. PATENT DOCUMENTS

| 3,371,352 A | 3/1968 | Siposs |
| 3,464,065 A | 9/1969 | Cromie |

(Continued)

FOREIGN PATENT DOCUMENTS

| DE | 19532973 | 11/1996 |
| EP | 1088529 | 4/2001 |

(Continued)

OTHER PUBLICATIONS

PCT International Search Report for PCT/US2006/006439, Applicant: Arbor Surgical Technologies, Inc., Forms PCT/IS/210 and 220, dated May 23, 2006 (7 pages).

(Continued)

*Primary Examiner* — Suba Ganesan
(74) *Attorney, Agent, or Firm* — Dicke, Billig & Czaja, PLLC

(57) ABSTRACT

A heart valve assembly includes an annular prosthesis and a valve prosthesis. The annular prosthesis includes an annular ring for dilating tissue within a biological annulus and a conformable sewing cuff extending radially from the annular member. The valve prosthesis includes a frame and a valve component. The annular ring is introduced into the biological annulus to dilate tissue surrounding the biological annulus and the sewing cuff conforms to tissue above the biological annulus. Fasteners are directed through the sewing cuff to secure the annular prosthesis to the biological annulus. The annular prosthesis may include a baleen element for biasing fabric on the annular ring outwardly to enhance sealing against the biological annulus. A valve prosthesis is then advanced into the sinus cavity, and secured relative to the annular prosthesis. The sewing cuff may enhance a seal between the valve prosthesis and annular prosthesis.

18 Claims, 27 Drawing Sheets

Related U.S. Application Data continuation of application No. 12/754,596, filed on Apr. 5, 2010, now Pat. No. 8,163,014, which is a continuation of application No. 11/069,081, filed on Feb. 28, 2005, now Pat. No. 7,717,955.

(52) U.S. Cl.
CPC ...... *A61F 2/2427* (2013.01); *A61F 2210/009* (2013.01); *A61F 2220/0016* (2013.01); *A61F 2250/006* (2013.01); *A61F 2250/0097* (2013.01)

(56) References Cited

U.S. PATENT DOCUMENTS

| | | |
|---|---|---|
| 3,571,815 A | 3/1971 | Somyk |
| 3,574,865 A | 4/1971 | Hamakaer |
| 3,686,740 A | 8/1972 | Shiley |
| 3,744,060 A | 7/1973 | Bellhouse |
| 3,800,403 A | 4/1974 | Anderson |
| 3,839,741 A | 10/1974 | Haller |
| 3,996,623 A | 12/1976 | Kaster |
| 3,997,923 A | 12/1976 | Posis |
| 4,035,849 A | 7/1977 | Angell |
| 4,259,753 A | 4/1981 | Liotta et al. |
| 4,451,936 A | 6/1984 | Carpentier et al. |
| 4,485,816 A | 12/1984 | Krumme |
| 4,535,483 A | 8/1985 | Klavitter et al. |
| 4,548,202 A | 10/1985 | Duncan |
| 4,680,031 A | 7/1987 | Alonso |
| 4,692,164 A | 9/1987 | Dzemeshkevich et al. |
| 4,790,843 A | 12/1988 | Carpentier et al. |
| 4,851,000 A | 7/1989 | Gupta |
| 4,892,541 A | 1/1990 | Alonso |
| 4,994,077 A | 2/1991 | Dobben |
| 5,032,128 A | 7/1991 | Alonso |
| 5,035,709 A | 7/1991 | Wieting et al. |
| 5,037,434 A | 8/1991 | Lane |
| 5,071,431 A | 12/1991 | Sauter et al. |
| 5,147,391 A | 9/1992 | Lane |
| 5,178,633 A | 1/1993 | Peters |
| 5,192,303 A | 3/1993 | Gatturna |
| 5,370,685 A | 12/1994 | Stevens |
| 5,469,868 A | 11/1995 | Reger |
| 5,549,665 A | 8/1996 | Vesely et al. |
| 5,571,175 A | 11/1996 | Vanney et al. |
| 5,573,543 A | 11/1996 | Akopov |
| 5,669,917 A | 9/1997 | Sauer |
| 5,716,370 A | 2/1998 | Williamson, IV et al. |
| 5,720,755 A | 2/1998 | Dakov |
| 5,725,554 A | 3/1998 | Simon |
| 5,776,188 A | 7/1998 | Shephard |
| 5,860,992 A | 1/1999 | Daniel |
| 5,891,160 A | 4/1999 | Williamson, IV |
| 5,935,163 A | 8/1999 | Gabbay |
| 5,976,183 A | 11/1999 | Ritz |
| 5,984,959 A | 11/1999 | Robertson et al. |
| 6,042,607 A | 3/2000 | Williamson |
| 6,045,576 A * | 4/2000 | Starr .................. A61F 2/2409 623/2.41 |
| 6,059,827 A | 5/2000 | Fenton, Jr. |
| 6,066,160 A | 5/2000 | Colvin et al. |
| 6,096,074 A | 8/2000 | Pedros |
| 6,106,550 A | 8/2000 | Magovern et al. |
| 6,126,007 A | 10/2000 | Kari |
| 6,143,025 A | 11/2000 | Stobie et al. |
| 6,162,233 A | 12/2000 | William son |
| 6,200,306 B1 | 3/2001 | Klostermeyer |
| 6,203,553 B1 | 3/2001 | Robertson |
| 6,217,611 B1 | 4/2001 | Klostermeyer |
| 6,241,765 B1 | 6/2001 | Griffin |
| 6,254,636 B1 | 7/2001 | Peredo |
| 6,287,339 B1 | 9/2001 | Vazquez et al. |
| 6,309,417 B1 | 10/2001 | Spence |
| 6,312,465 B1 | 11/2001 | Griffin et al. |
| 6,319,281 B1 | 11/2001 | Patel |
| 6,358,556 B1 | 3/2002 | Ding et al. |
| 6,371,983 B1 | 4/2002 | Lane |
| 6,402,780 B2 | 6/2002 | Williamson, IV et al. |
| 6,409,759 B1 | 6/2002 | Peredo |
| 6,425,916 B1 | 7/2002 | Garrison et al. |
| 6,447,524 B1 | 9/2002 | Knodel |
| 6,454,799 B1 | 9/2002 | Schreck |
| 6,461,382 B1 | 10/2002 | Cao |
| 6,468,305 B1 | 10/2002 | Otte |
| 6,530,952 B2 | 3/2003 | Vesely |
| 6,569,196 B1 | 5/2003 | Vesely |
| 6,709,457 B1 | 3/2004 | Otte et al. |
| 6,716,244 B2 | 4/2004 | Klaco |
| 6,776,785 B1 | 8/2004 | Yencho |
| 6,790,229 B1 | 9/2004 | Berreklouw |
| 6,893,459 B1 | 5/2005 | Macoviak |
| 6,939,365 B1 | 9/2005 | Fogarty |
| 7,083,648 B2 | 8/2006 | Yu |
| 7,172,625 B2 | 2/2007 | Shu et al. |
| 7,175,659 B2 | 2/2007 | Hill et al. |
| 2002/0055774 A1 | 5/2002 | Liddicoat |
| 2002/0123802 A1 | 9/2002 | Snyders |
| 2002/0128684 A1 | 9/2002 | Foerster |
| 2003/0023302 A1 | 1/2003 | Moe et al. |
| 2003/0045902 A1 | 3/2003 | Weadeock |
| 2003/0109922 A1 | 6/2003 | Peterson |
| 2004/0015232 A1 | 1/2004 | Shu et al. |
| 2004/0030381 A1 | 2/2004 | Shu |
| 2004/0044406 A1 | 3/2004 | Woolfson |
| 2004/0122514 A1 | 6/2004 | Fogarty et al. |
| 2004/0122516 A1 * | 6/2004 | Fogarty .............. A61B 17/0401 623/2.37 |
| 2004/0176839 A1 * | 9/2004 | Huynh .................. A61F 2/2445 623/2.4 |
| 2004/0210305 A1 | 10/2004 | Shu |
| 2004/0225356 A1 | 11/2004 | Frater |
| 2005/0043760 A1 | 2/2005 | Fogarty et al. |
| 2005/0080454 A1 | 4/2005 | Drews |
| 2005/0137686 A1 | 6/2005 | Salahieh et al. |
| 2005/0137689 A1 | 6/2005 | Salahieh et al. |
| 2005/0137691 A1 | 6/2005 | Salahieh et al. |
| 2005/0137696 A1 | 6/2005 | Salahieh et al. |
| 2005/0165479 A1 | 6/2005 | Drews et al. |
| 2006/0122634 A1 | 6/2006 | Ino |

FOREIGN PATENT DOCUMENTS

| | | |
|---|---|---|
| WO | WO9915112 | 4/1999 |
| WO | WO0044311 | 8/2000 |
| WO | WO0056250 | 9/2000 |
| WO | WO0059382 | 10/2000 |
| WO | WO0064380 | 11/2000 |
| WO | WO0110310 | 2/2001 |
| WO | WO0110312 | 2/2001 |
| WO | WO0158363 | 8/2001 |
| WO | WO0182840 | 11/2001 |
| WO | WO0187190 | 11/2001 |
| WO | WO03082363 | 10/2003 |
| WO | WO2004006810 | 1/2004 |
| WO | WO2005/039452 | 5/2005 |
| WO | WO2005039452 | 5/2005 |
| WO | WO2005/072655 | 8/2005 |

OTHER PUBLICATIONS

PCT Written Opinion of the International Search Authority for PCT/US2005/006439, Applicant: Arbor Surgical Technologies, Inc., Form PCT/ISA/237, dated May 23, 2006 (6 pages).

PCT International Search Report for PCT/US2006/006439, Applicant: Arbor Surgical Technologies, Inc., Forms PCT/ISA/210 and PCT/ISA/220, dated May 23, 2006, 7 pages.

PCT Written Opinion for PCT/US2006/006439, Applicant: Arbor Surgical Technologies, Inc., Forms PCT/ISA/237, dated May 23, 2006, 6 pages.

Office Actions and Applicant Responses for related U.S. Appl. No. 10/327,821, 229 pages.

(56) References Cited

OTHER PUBLICATIONS

Office Actions and Applicant Responses for related U.S. Appl. No. 10/355,429, 211 pages.
Office Actions and Applicant Responses for related U.S. Appl. No. 10/379,311, 49 pages.
Office Actions and Applicant Responses for related U.S. Appl. No. 10/646,639, 65 pages.
Office Actions and Applicant Responses for related U.S. Appl. No. 10/765,725, 49 pages.
Office Actions and Applicant Responses for related U.S. Appl. No. 11/069,457, 32 pages.
Office Actions and Applicant Responses for related U.S. Appl. No. 11/069,617, 37 pages.
Office Actions and Applicant Responses for related U.S. Appl. No. 10/681,700, 30 pages.

* cited by examiner

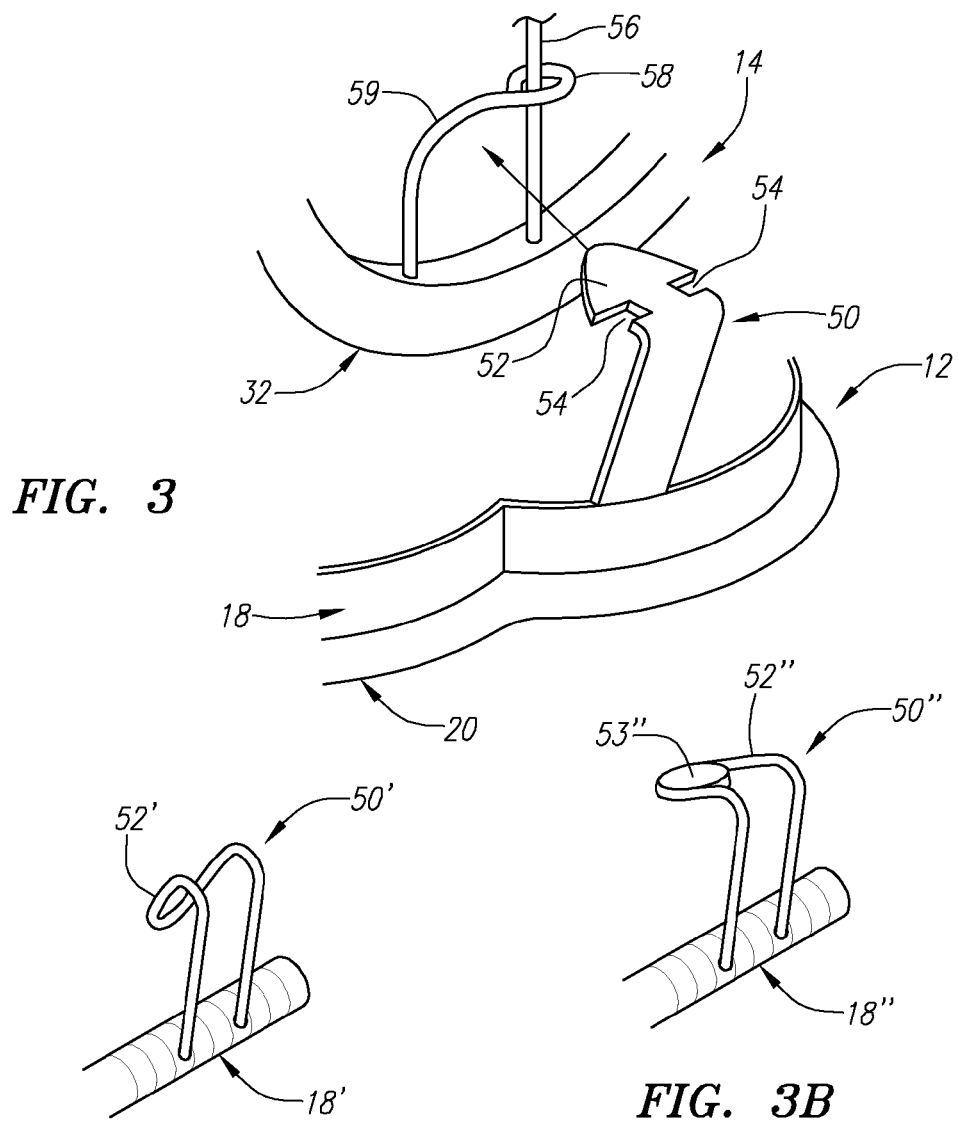
FIG. 3
FIG. 3A
FIG. 3B
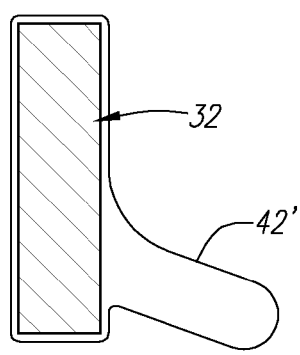
FIG. 4

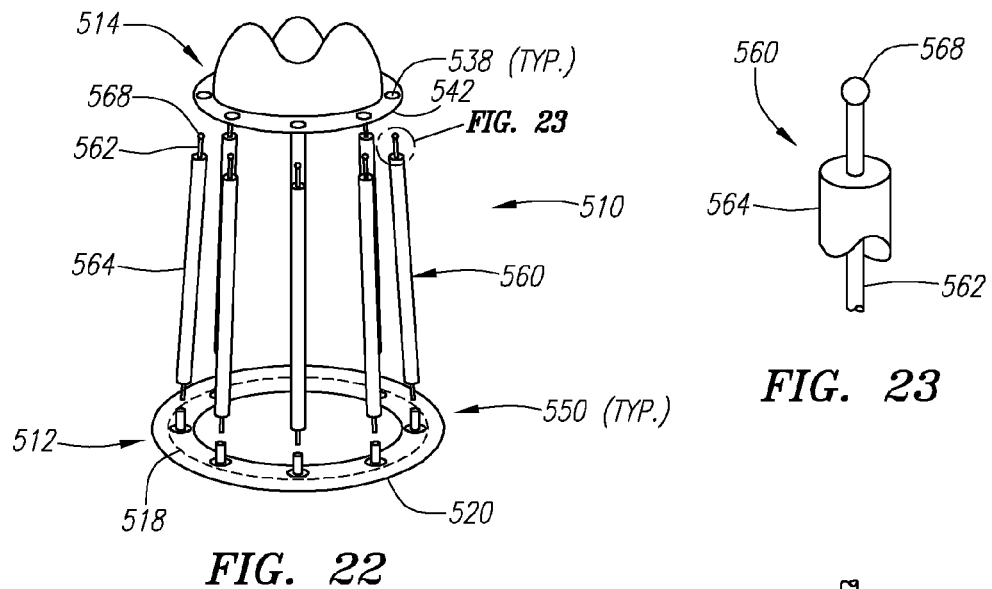
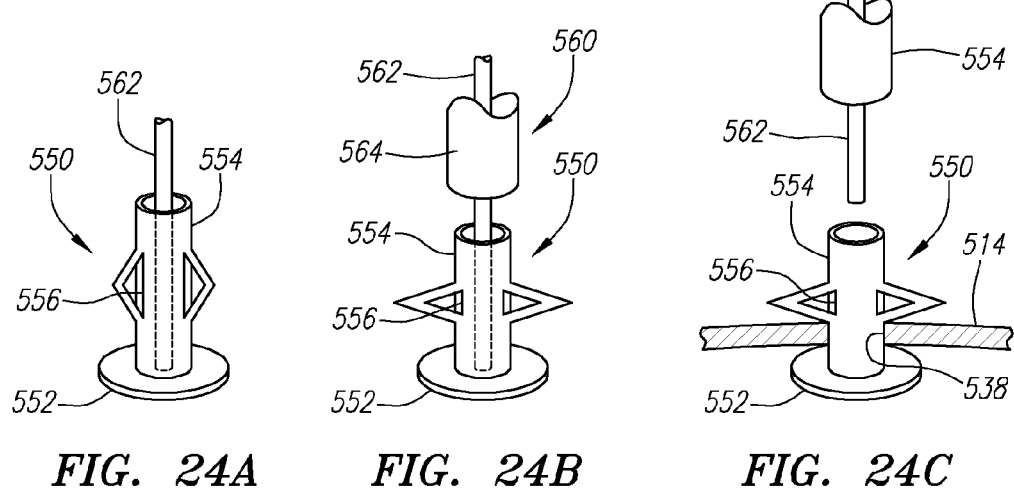
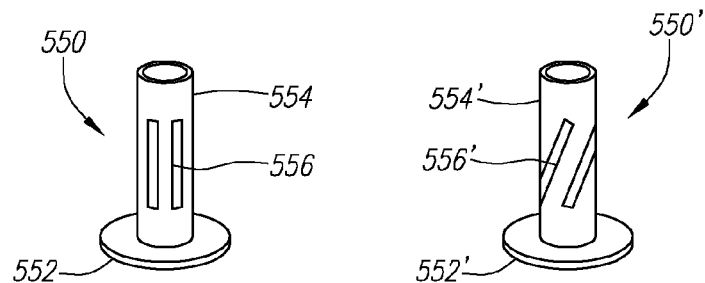

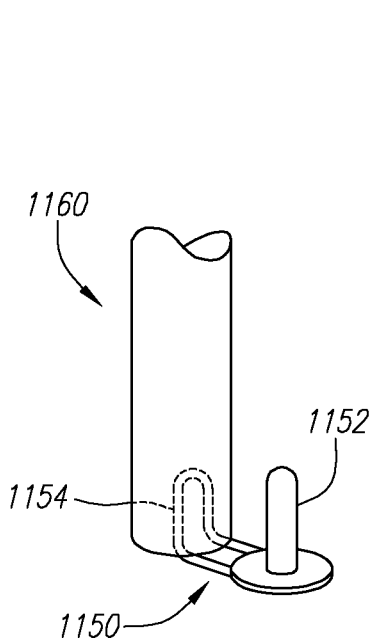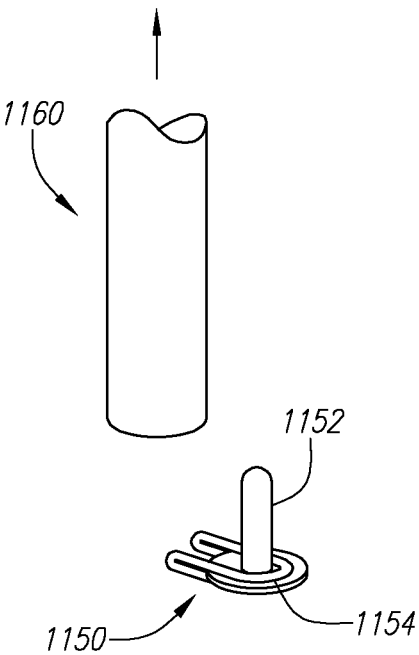
FIG. 38A   FIG. 38B
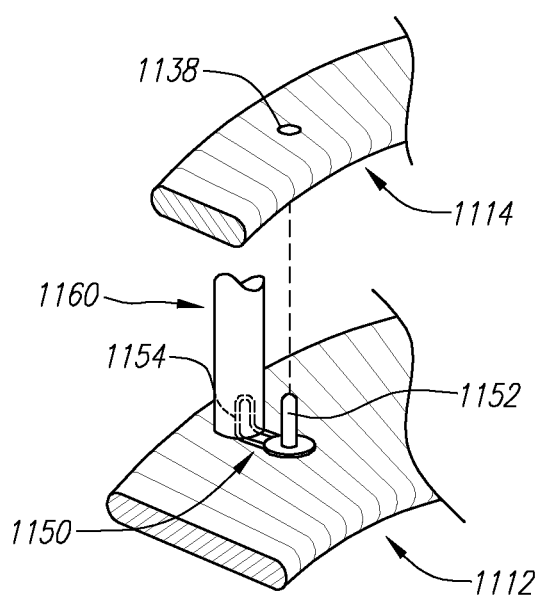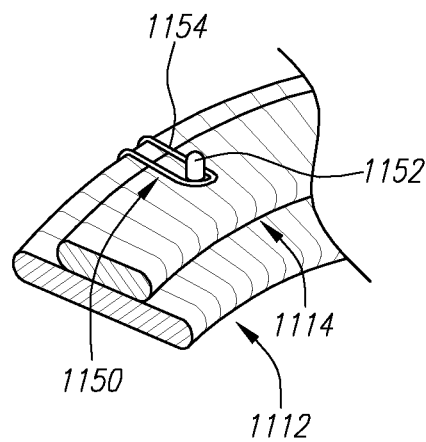
FIG. 39A   FIG. 39B

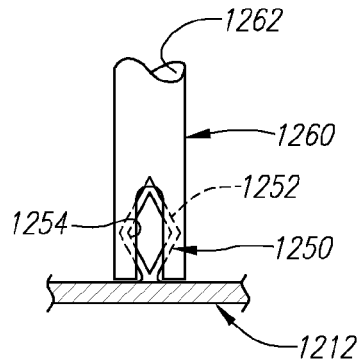
FIG. 40A
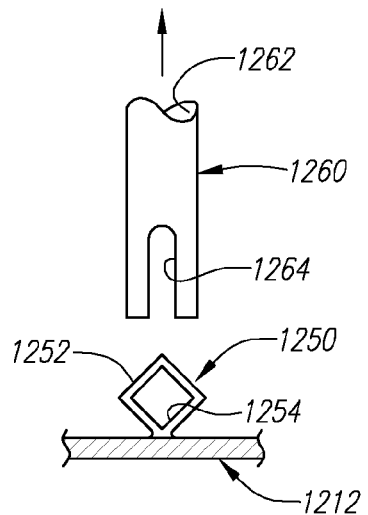
FIG. 40B
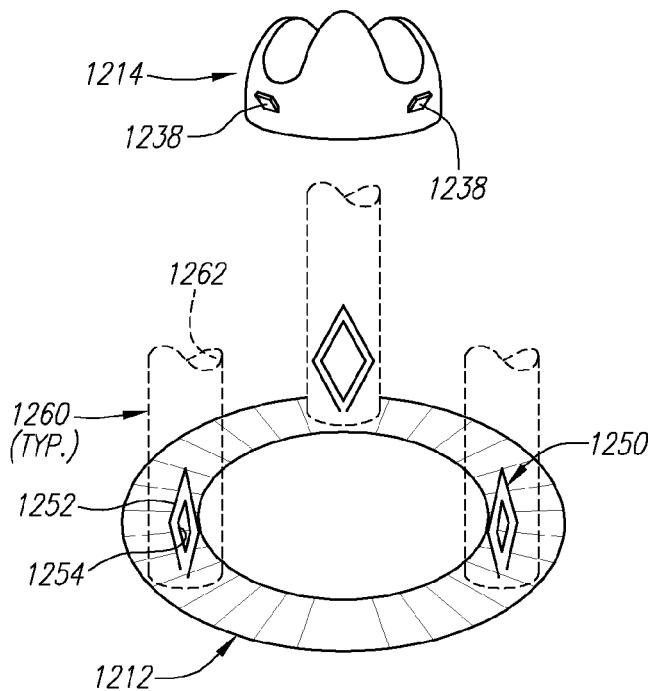
FIG. 41
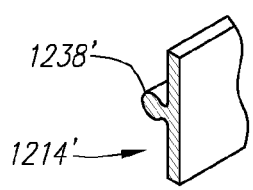
FIG. 43
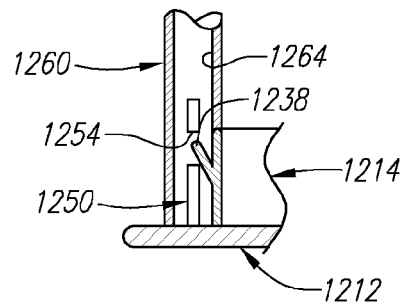
FIG. 42A
FIG. 42B

CONFORMABLE PROSTHESES FOR IMPLANTING TWO-PIECE HEART VALVES AND METHODS FOR USING THEM

This application is a Continuation of U.S. patent application Ser. No. 13/453,623, filed Apr. 23, 2012, now allowed, which is a Continuation of U.S. patent application Ser. No. 12/754,596 filed Apr. 5, 2010, now U.S. Pat. No. 8,163,014, Issued Apr. 24, 2012, which is a Continuation of U.S. patent application Ser. No. 11/069,081 filed Feb. 28, 2005, now U.S. Pat. No. 7,717,955, Issued May 18, 2010, which is incorporated by reference herein in its entirety.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuted down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

SUMMARY OF THE INVENTION

The present invention is directed to heart valves that may be implanted within a patient, and, more particularly, to multiple component heart valve assemblies that may be assembled together, and to apparatus and methods for making and implanting them.

In accordance with one embodiment, a prosthesis is provided for receiving a prosthetic valve to replace a pre-existing natural or prosthetic heart valve within a biological annulus adjacent a sinus cavity. The prosthesis may include an annular member implantable within the biological annulus for contacting tissue surrounding the biological annulus to provide an opening through the biological annulus, and a sewing cuff extending radially outwardly from the annular member. Optionally, the annular member may be resiliently compressible, expandable, and/or otherwise biased for dilating the biological annulus.

In one embodiment, the sewing cuff may be conformable for at least partially adopting a shape of tissue above or within the biological annulus. In addition or alternatively, the sewing cuff may be penetrable by fasteners for securing the sewing cuff to tissue surrounding the sinus cavity. Optionally, the sewing cuff may include one or more conformable elements, e.g., a plurality of flexible ribs and/or a lattice, e.g., to enhance sealing between the prosthetic valve and the annulus member. For example, the conformable element(s) may include a silicone, foam, fabric, or other core secured within fabric to provide the sewing cuff having sufficiently flexibility to conform to yet provide a seal against the surrounding tissue.

In accordance with another embodiment, a heart valve assembly is provided for implantation within a biological annulus that includes an annular prosthesis implantable within a biological annulus including an annular member for contacting tissue surrounding the biological annulus and a sewing cuff. The heart valve assembly also includes a prosthetic valve, e.g., including a multiple lobular shape for implantation above the biological annulus.

Optionally, one or more connectors may be provided on at least one of the annular prosthesis and the prosthetic valve for securing the prosthetic valve to the annular prosthesis. The one or more connectors may secure the prosthetic valve in a predetermined orientation relative to the annular prosthesis. For example, the one or more connectors may include a clip on the annular prosthesis for engaging a portion of the prosthetic valve when the prosthetic valve is secured to the annular prosthesis. Alternatively, the one or more connectors may include one or more latches, detents, interlocking elements on the prosthetic valve and/or the annular prosthesis.

In one embodiment, the sewing cuff may be resiliently flexible for conforming at least partially to the multiple lobular shape of the prosthetic valve and/or to the surrounding tissue, e.g., to enhance a seal between the prosthetic valve, the annular member, and/or the surrounding tissue. In addition or alternatively, the prosthetic valve, annular member, and/or sewing cuff may include a flexible skirt for enhancing a seal between the prosthetic valve and the annular prosthesis. Such enhanced seals may facilitate implanting a prosthetic valve having a multiple-lobular shape, e.g., corresponding to the supra-annular above a biological annulus, and an annular member having a substantially circular shape, e.g., corresponding to the biological annulus.

In accordance with still another embodiment, a prosthesis is provided for receiving a prosthetic valve that includes an annular member, a lattice extending around a circumference of the annular member, and a covering on at least a portion of the lattice to promote tissue ingrowth. The annular member may be sized for delivery within a biological annulus, and/or the lattice resiliently conformable with anatomy surrounding the biological annulus. In one embodiment, the lattice may include a plurality of circumferential elements extending around the circumference and a plurality of transverse elements extending between the ring elements. In addition or alternatively, the lattice may include a plurality of flexible ribs extending upwardly and/or downwardly from an annular base.

In accordance with yet another embodiment, a method is provided for implanting a prosthetic heart valve assembly to replace a natural or prosthetic heart valve implanted within a biological annulus below a sinus cavity. An annular member may be introduced into the biological annulus to direct tissue surrounding the biological annulus outwardly, e.g., to at least partially dilate the biological annulus. A valve prosthesis may be advanced into the sinus cavity, and secured relative to the annular member. A flexible sewing cuff or skirt may extend around the annular member that may be engaged by the valve prosthesis for enhancing a seal between the valve prosthesis and the annulus member.

In accordance with still another embodiment, a heart valve assembly is provided for implantation within a biological annulus that includes a base member implantable within a biological annulus and a valve member. The base member may include a rim extending about the circumference, and the valve member may include a lower edge or other element sized to be engaged with the rim to secure the valve member to the base member. For example, the rim may include a ridge extending upwardly from a base of the base member, thereby defining a space for receiving the lower edge of the valve member therein, e.g., to create an interference fit. Alternatively, the rim may include a plurality of tabs disposed about the circumference and/or extending upwardly from a base of the frame, thereby defining a space for receiving the lower edge of the valve member therein.

In addition or alternatively, the rim may include a ramped and/or tapered surface, e.g., upper edge for guiding the lower edge of the valve member into engagement with the rim. In addition, the lower edge of the valve member may include a ramped and/or tapered surface, and/or may include a plurality of tabs or other elements for engaging the rim of the base member. Optionally, the rim may be deflectable radially outwardly (or inwardly) when the lower edge of the valve member is guided into engagement with the rim, the rim being biased to return radially inwardly (or outwardly) to enhance an interference fit between the rim and the valve member.

In another option, a flexible skirt may extend from the base member and/or valve member for enhancing a seal between the valve member and the base member when the valve member is secured to the base member. For example, the base member may be sufficiently flexible to conform at least partially to the annulus of the heart, and the flexible skirt may deform to accommodate irregularities between the valve member and the base member, e.g., to enhance sealing between the valve member and the base member. The flexible skirt may extend laterally from the valve member and/or base member. For example, the flexible skirt may extend outwardly and/or upwardly from the base member or outwardly and/or downwardly, from the valve member, e.g., such that the flexible skirt enhances contact between the valve member and the base member. Exemplary materials for the flexible skirt may include foam, fabric, and/or silicone.

In accordance with another embodiment, a heart valve assembly is provided for implantation within an annulus of a heart that includes an annular base member and a valve member securable to the base member. The base member may include a circumference generally defining a plane, and may have a multi-lobular shape about the circumference, e.g., including lobes separated by scallops. The base member may include a resilient frame and a cuff extending around the frame about the circumstance. The frame may be biased to have an undulating shape such that lobe portions of the frame extend upwardly out of the plane and scallop portions extend downwardly out of the plane.

The cuff may be penetrable by sutures adjacent the scallop portions for pulling the scallop portions upwardly across the plane when the base member is implanted within an annulus of a heart. Thus, the undulating shape of the frame of the base member may define an amplitude that decreases when the scallop portions are pulled upwardly across the plane. In an exemplary embodiment, the valve member may have a multi-lobular shape and/or may include a valve frame including a circumference and having an undulating shape about the circumference such that the valve frame may nest with the frame of the base member.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 3 is a perspective detail, showing an exemplary connector for securing a valve member to a gasket member.

FIGS. 3A and 3B are perspective details of alternative embodiments of connectors for securing a valve member to a gasket member.

FIG. 4 is a cross-sectional detail of a valve member including a flexible skirt extending from a frame of the valve member.

FIG. 22 is a perspective view of a gasket member including a plurality of retainer elements with pullwire-hypotube actuators that may be received through a valve member when the valve member is directed towards the retainer elements.

FIG. 23 is a detail of a proximal end of a pullwire-hypotube actuator of the embodiment shown in FIG. 22.

FIGS. 24A-24C are perspective details of a retainer element, showing the retainer element buckling into an enlarged configuration when actuated.

FIGS. 25A and 25B are details of a retainer element having a pattern of slots formed therein to bias the retainer element to buckle in a desired manner when actuated.

FIG. 38A is a perspective view of a spring latch retained in an open position by a retaining member.

FIG. 38B is a perspective view of the spring latch of FIG. 38A, with the retaining member withdrawn, and the spring latch in its closed position.

FIGS. 39A and 39B are perspective details of a heart valve assembly including a valve member being secured to a gasket member using the latch of FIGS. 38A and 38B.

FIG. 40A is a side view of a yet another embodiment of a latch constrained in an open position by a retaining member.

FIG. 40B is a side view of the latch of FIG. 40A, with the retaining member withdrawn, and the latch in its closed position.

FIG. 41 is a perspective view of a heart valve assembly including a valve member and a gasket member including a plurality of the latches of FIGS. 40A and 40B.

FIGS. 42A and 42B are cross-sectional views, showing a method for securing the valve member to the gasket member of FIG. 41.

FIG. 43 is a cross-sectional view of an alternative embodiment of a valve member that may be included in the heart valve assembly of FIG. 41.

DETAILED DESCRIPTION OF THE PREFERRED EMBODIMENTS

Figure 1:
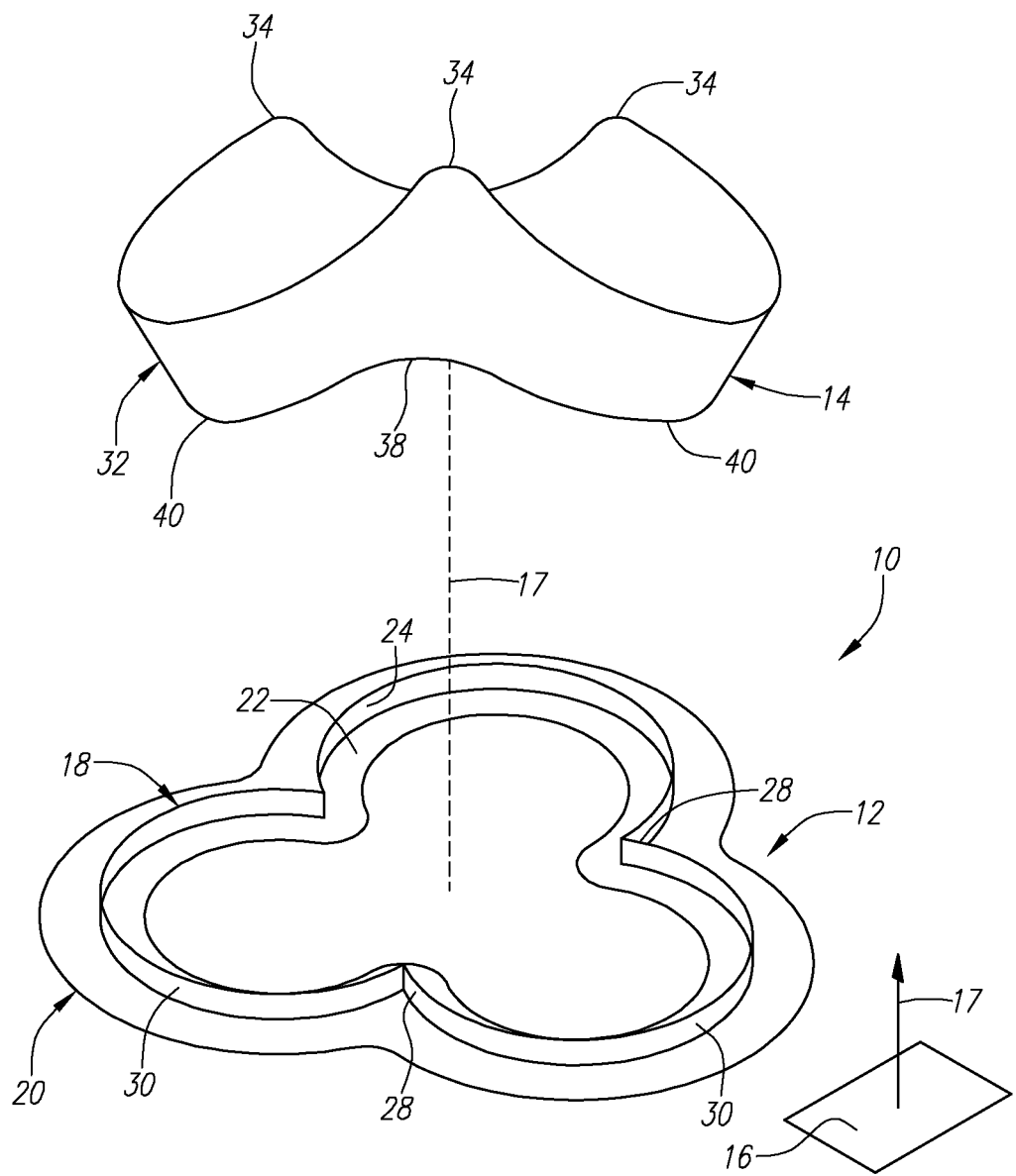
FIG. 1 is a perspective view of a prosthetic heart valve assembly, including a gasket member and a valve member.

Turning to the drawings, FIG. 1 shows an exemplary embodiment of a heart valve assembly 10 that generally includes a base member or "gasket member" 12 and a valve member or "crown" 14. The gasket member 12 is an annular shaped body generally defining a plane 16 and a longitudinal axis 17 extending substantially perpendicular to the plane 16. The gasket member 12 may have a noncircular shape within the plane 16, such as a multiple lobular shape. In one embodiment, the gasket member 12 has a tri-lobular shape, i.e., including three lobes 30 separated by cusps or scallops 28. The shape may correspond generally to a cross-section of a biological annulus within which the gasket member 12 may be implanted, as explained further below. It will be appreciated that the gasket member 12 may define other noncircular shapes within the plane 16, e.g., that may correspond to the anatomy of a patient within which the heart valve assembly 10 is to be implanted.

The gasket member 12 may include an anchoring ring or frame 18 and a flexible cuff or sewing ring 20 that may extend around a periphery of the anchoring ring 18. The anchoring ring 18 may be substantially rigid, e.g., retaining its shape, or semi-rigid, e.g., such that the anchoring ring 18 may be resiliently deformed, e.g., to conform at least partially to the anatomy within which the gasket member 12 is implanted. In addition or alternatively, the anchoring ring 18 may be elastically or super-elastically deformable, e.g., compressible into a smaller configuration, yet resiliently biased to return to the tri-lobular shape shown when released.

The cuff 20 may simply be a layer of fabric or other material covering at least a portion of the anchoring ring 18. For example, a layer of fabric (not shown) may cover all of the anchoring ring 18 other than any connectors and/or bearing surfaces, e.g., for securing the crown 14 to the gasket member 12. In addition or alternatively, as shown, the cuff 20 may include a section of material extending radially outwardly from the anchoring ring 18. The anchoring ring 18 and cuff 20 may be integrally formed as a single component or may be separate components attached to one another. In addition, the cuff 20 may be slidably or fixedly attached to the anchoring ring 18. Turning to FIG. 2, the anchoring ring 18 may include an annular base 22, e.g., a substantially flat sheet cut or otherwise formed to define an annular shape with a circumference, which may be defined by a circular, multiple lobular, or other enclosed loop generally lying in the plane 16. A rim 24 may extend from the base 22 around the circumference, e.g., upwardly out of the plane 16. The rim 24 may define a diameter or other cross-section that is at least marginally larger than the cross-section of the valve member 14, as described further below. Alternatively, the rim may define a diameter that is marginally smaller than the cross-section of the valve member 14.

The rim 24 may extend continuously around the circumference, e.g., along an outer edge 22a of the base 22. Alternatively, the rim may be defined by a plurality of tabs or other elements (not shown) extending upwardly from and/or spaced apart around the circumference of the base 22. Thus, the rim 24 and base 22 may define a space 25 therebetween for receiving and/or engaging a portion of the crown 14 therein, e.g., a lower edge 36 of the crown 14, as described further below.

Figure 2A:
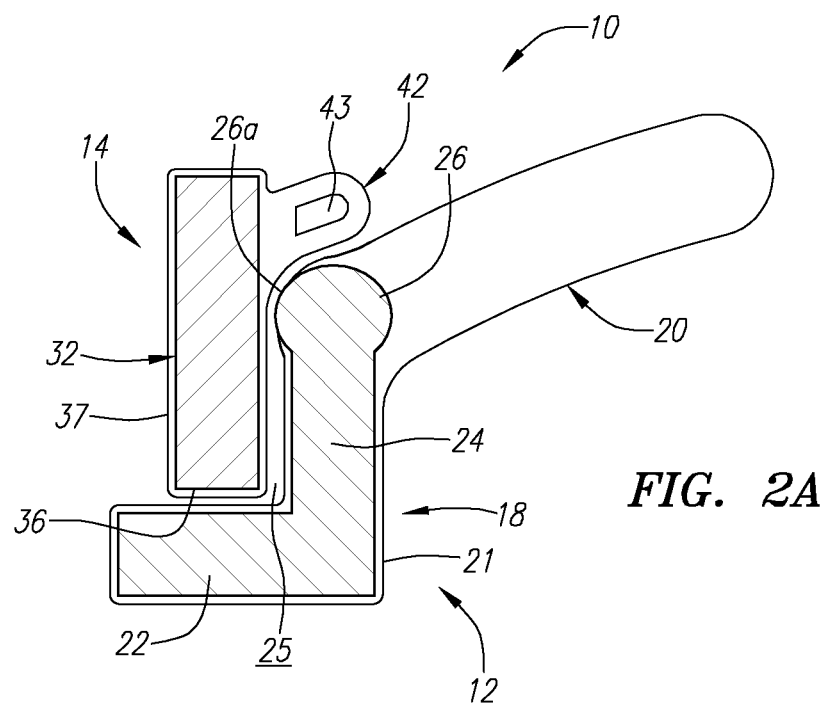
FIG. 2A is a cross-sectional view of the gasket member of FIG. 1, taken along line 2-2, being engaged with a frame of a valve member.

Optionally, the rim 24 may include a ramped edge or surface for guiding the crown 14 into engagement with the rim 24. For example, as shown in FIG. 2A, the rim 24 may terminate in an enlarged lip 26 having a rounded cross-section, thereby providing a ramped upper edge 26a. Alternatively, the lip may have other shapes, e.g., a beveled shape defining a rounded or straight inclined upper edge, such as the inwardly beveled edge 26a' shown in FIG. 2B. The ramped upper edge may facilitate aligning and/or guiding the crown 14 into proper orientation and/or into engagement with the anchoring ring 18, as explained further below.

With continued reference to FIG. 2A, at least a portion of the rim 24, e.g., adjacent the upper edge 26a of the rim 24, may be deflectable relative to the base 22, e.g., to facilitate insertion and/or engagement with the crown 14. As shown, the rim 24 may be deflectable radially outwardly relative to the base 22, e.g., when the lower edge 36 of the crown 14 is guided into the space 25 defined by the rim 24. The rim 24 may be resilient, e.g., elastic or superelastic, such that the rim 24 is biased to return radially inwardly, e.g., for enhancing an interference fit between the rim 24 and the crown 14.

Optionally, the gasket member 12 may include one or more detents or other connectors for securing the crown 14 to the gasket member 12 in addition to or instead of the rim 24. For example, as shown in FIG. 3, the anchoring ring 18 may include a plurality of fingers 50 that extend upwardly, e.g., from the outer edge 22a of the base 22. Each finger 50 may end in a bent tip 52 that includes one or more notches 54 therein. As shown, the bent tip 52 extends inwardly substantially parallel to the plane 16 such that the notch(es) 54 extends over the base 22 below. Alternatively, the bent tip 52 may extend downwardly, e.g., back towards the base 22, to provide a guide for the crown 14 (not shown). In another alternative, shown in FIG. 3A, the finger 50' may be formed from a length of wire, bent to provide a bent tip 52.' Optionally, as shown in FIG. 3B, a wire finger 50" may be provided that includes a knob or catch 53" on the bent tip 52." In addition or alternatively, other connectors may be provided, such as those disclosed in application Ser. No. 10/765,725, the entire disclosure of which is expressly incorporated by reference herein.

Returning to FIG. 1, the crown 14 generally includes an annular shaped body or frame 32 and one or more valve elements. The frame 32 may have a noncircular, e.g., multiple lobular shape, e.g., complementary to the gasket member 12. For example, the crown 14 may have a tri-lobular shape, similar to the gasket member 12, including three lobes 40 separated by cusps or scallops 38. In an exemplary embodiment, the crown 14 is a prosthetic valve member, i.e., an annular frame 32 carrying a plurality of tissue leaflets (not shown for clarity) extending from the frame 32, e.g., attached to commissures 34. The frame 32 may include a plurality of struts (also not shown for clarity) that may be attached to and/or otherwise carry the leaflets. For example, the struts may include a laminate structure, including two or more sheets of flexible material, similar to the struts disclosed in U.S. Pat. No. 6,371,983, the entire disclosure of which is expressly incorporated by reference herein.

Alternatively, the crown 14 may be a connecting device to which a valve (not shown) may be connected or that may otherwise receive a valve component, such as the connection adapter elements shown in co-pending application Ser. No. 10/646,639, filed 22 Aug. 2003, the entire disclosure of which is expressly incorporated by reference herein. In another alternative, the crown 14 may include a mechanical valve or other valve (not shown), such as those disclosed in application Ser. No. 10/765,725, incorporated by reference above.

As best seen in FIG. 2A, the frame 32 may include a lower edge 36 that defines a diameter or other cross-section, e.g., similar to the cross-section of the rim 24. The lower edge 36 may be continuous or may be defined by a plurality of tabs spaced about the circumference of the frame 32. As shown, the cross-section of the lower edge 36 may be marginally smaller than the rim 24 such that the lower edge 36 may be inserted into the rim 24 to at least partially secure the crown 14 to the gasket member 12. Alternatively, the lower edge 36 may be marginally larger than the rim 24 such that the lower edge fits over the rim 24, yet provides a desired interference fit.

Figure 2B:
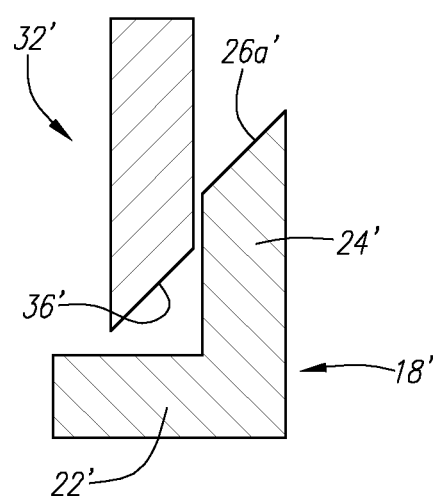
FIG. 2B is a cross-sectional view of an alternative embodiment of a gasket member.

Thus, the lower edge 36 may fit into the space 25 defined by the rim 24 and base 22 yet sufficiently bear against the rim 24 such that the crown 14 may be secured to the gasket member 12 by the friction between the lower edge 36 and the rim 24. Optionally, as shown in FIG. 2B, the lower edge 36' of the frame 32' may be ramped similar to the rim 24,' e.g., to facilitate insertion and/or engagement between the lower edge 36' and the rim 24.'

The frame 32 of the crown 14 may be formed from one or more sheets of material rolled or otherwise formed such that the width of the sheet extends parallel to the longitudinal axis 17. Thus, the lower edge 36 may simply be the edge of the sheet that lies generally within the plane 16. Alternatively, the lower edge 36 may be a corner, e.g., where two surfaces of the frame 32 meet.

In addition or alternatively, the frame 32 and/or other component of the crown 14 may include one or more connectors for securing the crown 14 to the gasket member 12. For example, as shown in FIG. 3, the crown 14 may include one or more sutures 56 with slip knots 58 that may receive corresponding fingers 50 on the gasket member 12. For each connector, the slip knot 58 may be provided by a suture, thread or other filament 59 spaced apart from the corresponding suture 56 by a predetermined distance, e.g., greater than a width of the fingers 50. When the crown 14 is directed into contact with the gasket member 12, each finger 50 may be directed inwardly, e.g., using a tool (not shown), until the bent tip 52 is received through a corresponding suture 56 and filament 59. Alternatively, the finger(s) 50 may be biased inwardly but may be deflected outwardly, e.g., by a tool (not shown) or by ramping the bent tip(s) 52 downwardly, such that the finger(s) 50 may be resiliently moved out of the way as the crown 14 is engaged with the gasket member 12.

With the notch(es) 54 aligned with the filament 59, the suture 56 may be pulled, the resulting tension causing the slip knot 58 to tighten around the bent tip 52, e.g., until a portion of one or both of the filament 59 and the suture 56 are received within the notch(es) 54. The suture 56 may then be knotted or otherwise tied off, and/or cut to secure the crown 14 to the gasket member 12. Similar methods may be used to secure the fingers 50' and 50" shown in FIGS. 3A and 3B within the slip know 58, thereby capturing the bent tip 52' and/or knob 53" within the slip knot 58.

Components of the heart valve assembly 10 (or other embodiments described herein), e.g., the anchoring ring 18 and/or sewing ring 20 of the gasket member 12, and/or the frame 32 and/or struts of the crown 14, may be made from one or more materials, such as an alloy of stainless steel, nickel titanium ("Nitinol"), cobalt-chrome (e.g., ELGILOY® from Elgin Specialty Metals, Elgin, Ill.; CONICHROME® from Carpenter Metals Corp., Wyomissing, Pa.), molybdenum (e.g., molybdenum TZM alloy, as disclosed, for example, in International Publication No. WO 03/082363 A2, published 9 Oct. 2003, the entire disclosure of which is expressly incorporated by reference herein), and/or tungsten-rhenium (e.g., as disclosed in International Publication No. WO 03/082363, the entire disclosure of which is also expressly incorporated by reference herein). In addition or alternatively, the components may be made from polymers, such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, polyetherblock co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, fluorinated ethylene propylene (FEP), and/or thermoplastics. In addition or alternatively, the components may include other materials, such as extruded collagen, silicone, echogenic, radioactive, radiopaque material or combinations thereof. Exemplary radiopaque materials that may be used include barium sulfate, titanium, stainless steel, nickeltitanium alloys, tantalum, and/or gold.

The components of the heart valve assembly 10 may be manufactured using methods known to those skilled in the art. For example, these methods may include molding, machining, casting, forming (e.g., pressure forming), crimping, stamping, melting, screwing, gluing, welding, die cutting, laser cutting, electrical discharge machining (EDM), etching, or combinations thereof.

Any or all components of the heart valve assembly 10 (or other embodiments described herein), for example, the cuff 20, may include a matrix for cell ingrowth, a fabric, or other flexible material, e.g., a fabric covering 21, as shown in FIG. 2A. The fabric or other covering may act as a matrix for cell ingrowth, and/or may be easily penetrated with a needle and/or a fastener, e.g., used to attach the cuff 20 to an annulus within which the heart valve assembly 10 is implanted. Exemplary fabric material may include polyester (e.g., DACRON® from E. I. du Pont de Nemours and Company, Wilmington, Del.), polypropylene, PTFE, ePTFE, nylon, extruded collagen, silicone, and/or combinations thereof. Optionally, the cuff 20 may be an o-ring, or may include a cushioned material, double velour material, and the like, attached using glue or other adhesives and/or fasteners. Similarly, all or a portion of the crown 14 may also include such a matrix, such as a fabric covering 37, as shown in FIG. 2A. Methods for covering all or components of the heart valve assembly 10 may include sintering, spray coating, adhesion, loose covering, dipping, or combinations thereof.

For example, the anchoring ring 18 may be at least partially covered with fabric 21, e.g., to enhance tissue ingrowth. The fabric 21 may cover all surfaces of the anchoring ring 18 or may cover only those areas not intended to contact the crown 14, e.g., the surfaces intended to provide an interference fit or including connectors for securing the crown 14. The fabric 21 may be part of the cuff 20 or the cuff 20 may be attached to the fabric 21. Similarly, the frame 32 and/or any struts (not shown) of the crown 14 may also be at least partially covered with fabric 37. In addition to enhancing tissue ingrowth, such fabric 37 may also provide a desired degree of flexibility of the components of the crown 14, e.g., allowing components to move without fatigue. As shown in FIG. 2A, the fabric 37 may also be shaped to provide a flexible skirt 42 around at least a portion of the crown 14. For example, fabric may be folded over on itself to provide a skirt 42 defined by a double thickness of fabric that extends from the frame 32. The skirt 42 may be free to move and/or conform, e.g., when the crown 14 is secured to the gasket member 12, as described further below. Optionally, the space between the double thickness of fabric may be filled with flexible material 43, e.g., foam, fabric, silicone, and the like, which may be provide a self-supporting shape for the skirt 42, yet may be sufficiently flexible and/or deformable to conform as desired. Alternatively, the skirt 42 may be defined by a single layer of fabric and/or other flexible material (not shown) attached to or otherwise extending from the frame 32 and/or fabric 37.

The skirt 42 may extend laterally from the frame 32, e.g., outwardly and upwardly as shown. Optionally, the skirt 42 may be sufficiently large to at least partially overlap the cuff 20, e.g., such that sutures or fasteners (not shown) may be received through both the skirt 42 and the cuff 20, as explained further below. Alternatively, as shown in FIG. 4, a skirt 42' may be provided that extends outwardly and downwardly from the frame 32. When the crown 14 is directed into contact with the gasket member 12 (not shown), the skirt 42' may contact the gasket member 12 before the frame 32, e.g., to enhance a seal between the crown 14 and the gasket member 12. In another alternative, the skirt 42 may extend substantially perpendicular to or otherwise transversely relative to the longitudinal axis 17.

In addition or alternatively, a flexible skirt (not shown) may be provided on the gasket member 12, similar to the embodiments described further below, e.g., to further enhance a seal between the crown 14 and the gasket member 12. Such a skirt may extend inwardly, outwardly, and/or upwardly to contact the crown 14 as it is engaged with the gasket member 12.

Optionally, the gasket member 12 and/or crown 14 may include one or more guide markers (not shown), e.g., to facilitate aligning the crown 14 with the gasket member 12, such as those disclosed in application Ser. No. 10/765,725, incorporated by reference above, and application Ser. No. 10/327,821, filed Dec. 20, 2002, the entire disclosure of which is also expressly incorporated by reference herein. The guide markers may provide a visual indication (e.g., directly and/or using an imaging apparatus), an auditory indication, and/or a tactile indication of the relative orientation and/or location of the crown 14 with the gasket member 12, e.g., about the longitudinal axis 17. In addition or alternatively, the gasket member 12 and/or crown may include cooperating guides for facilitating orientation and/or engagement of the crown 14 to the gasket member 12. For example, one of the gasket member 12 and/or crown 14 may include one or more grooves or slots and the other may include one or more corresponding tabs or ridges that allow the crown 14 to be engaged with the gasket member 12 in a predetermined orientation, e.g., to facilitate aligning the multi-lobular shapes of the crown 14 and gasket member 12. Exemplary guide elements are disclosed in co-pending application Ser. No. 10/327,821, incorporated by reference above.

Optionally, the heart valve assembly 10 (or other embodiments described herein) and/or any fabric or other materials therein may be filled and/or coated with one or more agent delivery matrices known to those skilled in the art, e.g., therapeutic agents, and/or diagnostic agents. For example, any components, sub-assemblies, or the entire heart valve assembly 10 may be coated, e.g., by dip-coating or spray-coating methods known to one having ordinary skill in the art, utilizing materials such as PTFE, polyester, gelatin, gel, other polymers or combinations thereof. An exemplary method for coating a medical device for vascular use is disclosed in U.S. Pat. No. 6,358,556 by Ding et al., the entire disclosure of which is expressly incorporated by reference herein. Time release coating methods may also be used to delay the release of an agent in the coating. The agents may include one or more of radioactive materials, radiopaque materials, cytogenic agents, cytotoxic agents, cytostatic agents, thrombogenic agents, lubricious and/or hydrophilic materials, anti-inflammatory agents, immunosuppressive agents, and the like. Examples of other agents that may be used are disclosed in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649. The entire disclosures of these references and any others cited therein are expressly incorporated by reference herein.

Turning to FIGS. 5A-5E, an exemplary method is shown for implanting a prosthetic heart valve assembly, such as the heart valve assembly 10 described above, within a biological annulus 90. Alternatively, other methods may be used, such as those described elsewhere herein for implanting the heart valve assembly 10 (or other embodiments described herein). The annulus 90 may be the site for replacement of an existing natural or previously implanted heart valve, such as a tricuspid, mitral, aortic, or pulmonary valve within a patient's heart (not shown). The annulus 90 may have multiple, for example two or three natural lobes 92 (three lobes being shown in FIG. 5A with one lobe cut-away). Although the method described below refers generally to the heart valve assembly 10 shown in FIG. 1, it will be appreciated that any of the components described herein may be implanted using similar procedures.

Before implanting the heart valve assembly 10, the patient may be prepared for the procedure using known methods. For example, the patient may be placed on cardiopulmonary bypass (CPB), and the patient's heart may be exposed, e.g., by sternotomy, thoracotomy, or other open or minimally invasive procedure. An incision may be created in the blood vessel above the valve being replaced (not shown), e.g., the aorta for an aortic valve replacement, in order to access the annulus 90. The existing natural or prosthetic heart valve (also not shown) may be removed from the annulus 90 using known methods.

Figure 5A:
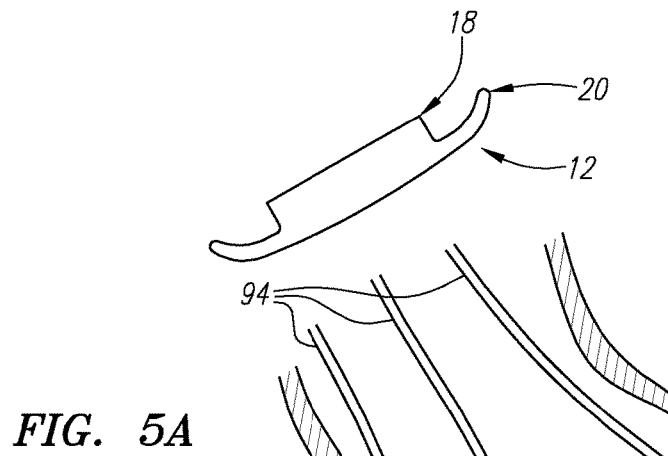
FIGS. 5A-5E are cross-sectional views of an annulus within a heart of a patient, showing a method for implanting a prosthetic heart valve assembly within the annulus.

As shown in FIG. 5A, a plurality of pilot sutures 94 may be secured through tissue surrounding the annulus 90. For example, using conventional methods, a needle (not shown) may be used to deliver each pilot suture 94 through the tissue surrounding the annulus 90. Once each pilot suture 94 is secured through the surrounding tissue, both ends of each pilot suture 94 may be maintained outside the annulus, and may be secured together, e.g., to a single needle to facilitate advancing the respective suture 94 through one or more components of the heart valve assembly 10, as described further below. Other methods may also be used for delivering the pilot sutures or other threads or filaments through the tissue surrounding the annulus 90.

Figure 6:
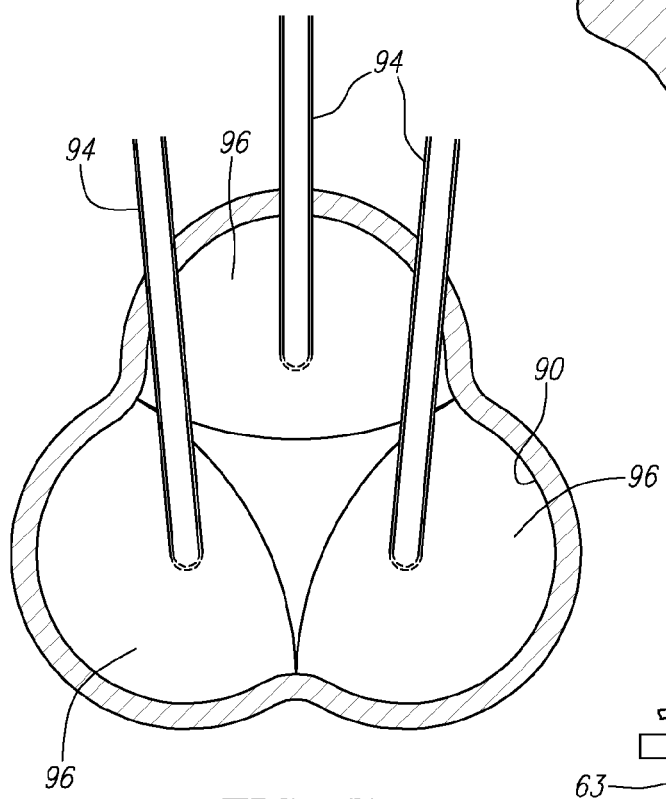
FIG. 6 is a cross-sectional detail of a pledget for distributing forces from a suture secured through tissue.

If desired, as shown in FIG. 6, a pledget 98 may be advanced over or otherwise delivered via each pilot suture 94. The pledget 98 may distribute tensile forces applied, e.g., by pulling the suture 94, over a larger surface of the tissue. Thus, the pledget 98 may prevent the pilot suture 94 from tearing through or otherwise damaging the tissue within the pilot suture 94.

Figure 7:
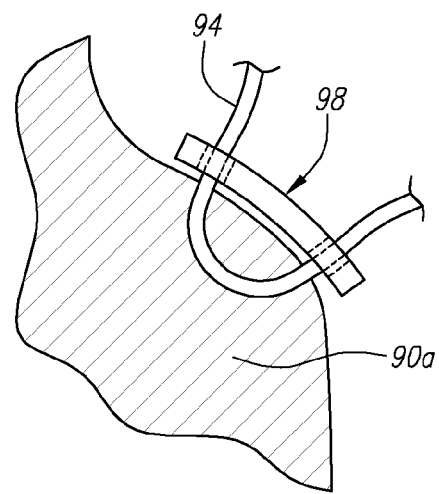
FIG. 7 is a cross-sectional view across an annulus, showing pilot sutures secured through the tissue of each nadir of the annulus.

Returning to FIG. 5A with additional reference to FIG. 7, in one embodiment, a pilot suture 94 is secured through each of the nadirs 96 of the annulus 90. Thus, for a tricuspid annulus, such as the aortic valve annulus shown in FIG. 7, three pilot sutures 94 may be secured through the respective three nadirs 96 of the annulus 90. It will be appreciated that other quantities of sutures (not shown) may be secured within the annulus, e.g., two or more in each nadir or distributed evenly or in another configuration around the annulus 90.

Figure 5B:
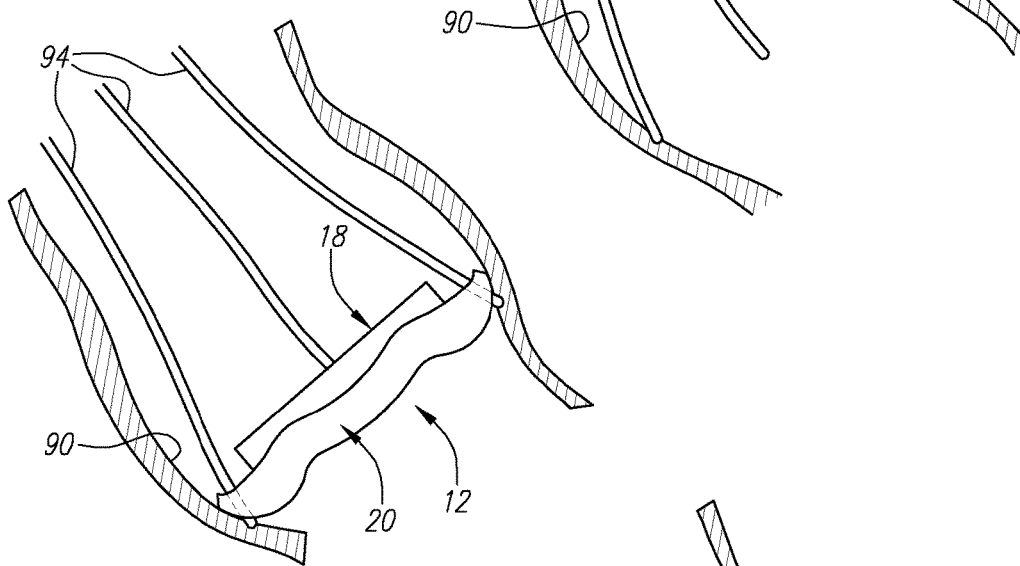

Turning to FIG. 5B, with the desired number of pilot sutures 94 secured to the annulus, a gasket member 12 may be advanced into the annulus 90 via the pilot sutures 94. The gasket member 12 may be selected based upon the anatomy encountered, e.g., having a plurality of lobes 30 matching the lobes 92 of the annulus 90 and/or having a diameter or other cross-sectional dimension corresponding to the interior cross-section of the annulus 90. Optionally, the base member 12 may be implanted above the natural valve annulus, e.g., within the enlarged space above a natural valve annulus. This configuration may allow a larger heart valve assembly 10 to be implanted, thereby maximizing the open area through which blood may flow through the implantation site.

The pilot sutures 94 may be directed through the cuff 20 of the gasket member 12 and the gasket member 12 may be advanced or "parachuted" down the pilot sutures 94 into the annulus 90. For example, the pilot sutures 94 may be driven through the fabric of the cuff 20 using a needle or other tool (not shown) such that the free ends of the pilot sutures 94 remain outside the patient's body. Alternatively, the anchoring ring 18 or other component of the gasket member 12 may include a plurality of openings, tubes, or other elements (not shown) for guiding or otherwise accommodating the sutures 94 therethrough, such as those disclosed in application Ser. No. 10/765,725, incorporated by reference above.

The pilot sutures 94 may be distributed around the circumference of the gasket member 12 in a desired configuration. For example, if a single pilot suture 94 is secured through each nadir 96, the pilot sutures 94 may be advanced through the cuff 20 (or anchoring ring 18) adjacent respective cusps 28 (not shown, see FIG. 1) of the gasket member 12. Thus, as the gasket member 12 is advanced down the pilot sutures 94, the gasket member 12 may automatically align itself with the orientation of the annulus 90, e.g., such that the lobes 30 of the gasket member 12 are received in the lobes 94 of the annulus 90 and the cusps 28 are received over or within the nadirs 96.

Figure 5C:
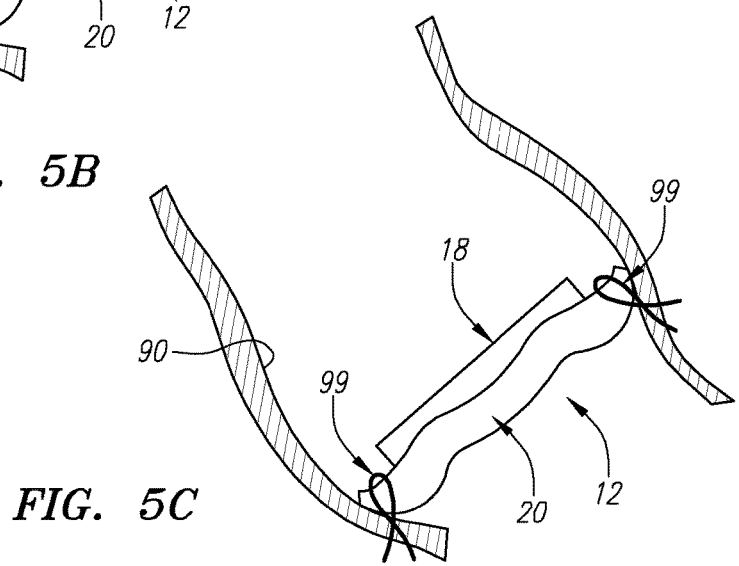

Turning to FIG. 5C (in which the pilot sutures 94 are omitted for clarity), a plurality of fasteners may be directed through the gasket member 12 into the tissue surrounding the annulus 90, e.g., to secure the gasket member 12 within the annulus 90. For example, fasteners 99 may be driven through the cuff 20 of the gasket member 12 into the surrounding tissue, e.g., distributed generally evenly around the circumference of the gasket member 12. Exemplary fasteners that may be used and apparatus and methods for delivering them are disclosed in U.S. Pat. No. 6,402,780 and in co-pending application Ser. No. 10/681,700, filed Oct. 8, 2003. The disclosures of these references and any others cited therein are expressly incorporated by reference herein.

Optionally, to enhance securing the gasket member 12 within the annulus 90, the pilot sutures 94 may be pulled to apply tension to the tissue through which the pilot sutures 94 are secured. For example, as shown in FIG. 7, the nadirs 96 of the annulus 90 may have a tendency to collapse and/or at least partially occlude the annulus 90. Applying tension to the pilot sutures 94 may open the annulus 90 and/or pull the tissue of the nadirs 96 into apposition with the gasket member 12.

Figure 8:
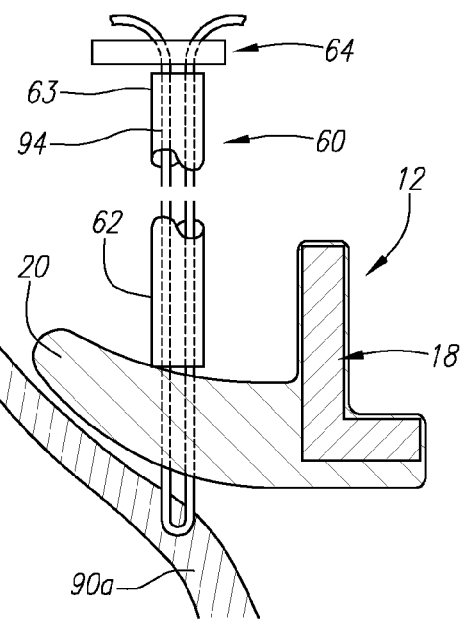
FIG. 8 is a cross-sectional detail showing a tool for maintaining tension on a suture.

Turning to FIG. 8, in one embodiment, a tubular member or tool 60 may be advanced over each pilot suture 94 until a distal end 62 of the tool 60 contacts the cuff 20 at the location where the pilot suture 94 has been directed through the cuff 20. The tool 60 may be a substantially enclosed tube having sufficient length to extend from outside the patient into the annulus 90. Alternatively, the tool 60 may be a "C" shaped tube whose longitudinal edges (not shown) overlap or abut one another, thereby defining a lumen 61 through which a pilot suture 94 may be disposed. For example, a pilot suture 94 may be advanced into the distal end 62 of the tool 60 until it exits a proximal end 63 of the tool 60. Alternatively, if the tool 60 has a "C" shaped cross-section, the pilot suture 94 may be forced transversely between the longitudinal edges into the lumen 61.

Each pilot suture 94 may then be pulled, or, otherwise, sufficient tension may be applied to the pilot suture 94 to pull the underlying tissue 90a into substantial contact with the cuff 20. A clamp 64 may then be applied to prevent the pilot suture 94 and tool 60 from moving relative to one another. For example, as shown in FIG. 6, a clamp 64 may be applied transversely across the free ends 94a of the pilot suture 94 extending from the proximal end 63 of the tool 60. Alternatively, a clamp or other device may be clamped around the proximal end 63 of the tool 60, e.g., to crimp the tool 60 down onto the pilot suture 94. Thus, the free ends 94a of the pilot suture 94 may be secured relative to the tool 60, thereby preserving the desired tension. The tool 60 may then be released, freeing the user's hands for other tasks during the procedure, e.g., driving the fasteners 99 through the cuff 20 into the tissue 90a.

Once sufficient fasteners 99 are installed, the clamp 64 and tool 60 may be removed, e.g., to release the free ends 94a of the pilot sutures 94.

Alternatively, the pilot sutures 94 may be eliminated and the gasket member 12 may be carried using a tool (not shown) into the annulus 90, whereupon a plurality of fasteners 99 may be delivered through the gasket member 12 into the tissue surrounding the annulus 90. Optionally, the tool may include an element (not shown) for presenting the tissue to enhance engagement of the fasteners 12 through the gasket member 12 into the tissue or a separate tool (also not shown) may be introduced into annulus 90 to present the tissue or otherwise enhance delivery of the fasteners 99.

Figure 5D:
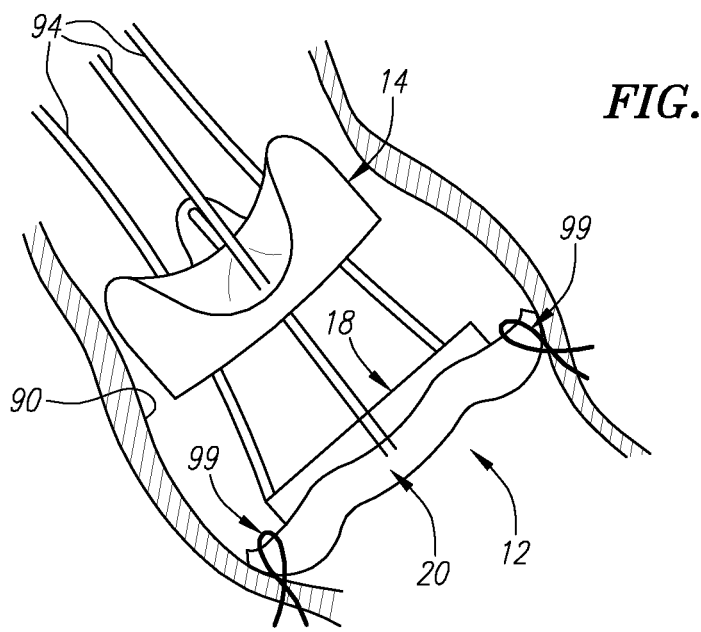

Turning to FIG. 5D, a crown 14 may be advanced into the annulus 90, e.g. via the pilot sutures 94 until the crown 14 contacts the gasket member 12. For example, the needle or other tool (not shown) may be used to direct the pilot sutures 94 through the crown 14, e.g., through the fabric covering 37 (not shown, see FIG. 2A) and/or through corresponding openings or other receiving elements in the frame 32. Similar to the gasket member 12, the pilot sutures 94 may be directed through predetermined locations on the crown 14 to facilitate orienting the crown about longitudinal axis 17 relative to the gasket member 12 and annulus 90. For example, the pilot sutures 94 may be directed through the crown 14 adjacent to the cusps 38 similar to the locations in the gasket member 12.

As the crown 14 is advanced into contact with the gasket member 12 within the annulus 90, the crown 14 may automatically dock into the gasket member 12. For example, as described above with reference to FIG. 2A, the gasket member 12 may include a rim 24 that engages a lower edge 36 of the crown 14 as the crown 14 docks into (or around) the gasket member 12. The interference fit between the lower edge 36 and the rim 24 may provide sufficient connection to secure the crown 14 to the gasket member 12.

In addition or alternatively, as described above with respect to FIG. 3, the gasket member 12 may include a plurality of fingers 50 that may be received in loops defined by sutures 56 and a slip knot 58. Once the fingers 50 are properly received, the sutures 56 may be pulled to tighten the slip knot 58, whereupon the sutures 56 may be tied or otherwise secured. The sutures 56 may then be cut or otherwise removed from the patient's body. In further options, the crown 14 and/or gasket member 12 may include one or more other connectors, such as those disclosed in application Ser. No. 10/765,725, incorporated by reference above. Such connectors may used together to provide redundant connections.

Figure 5E:
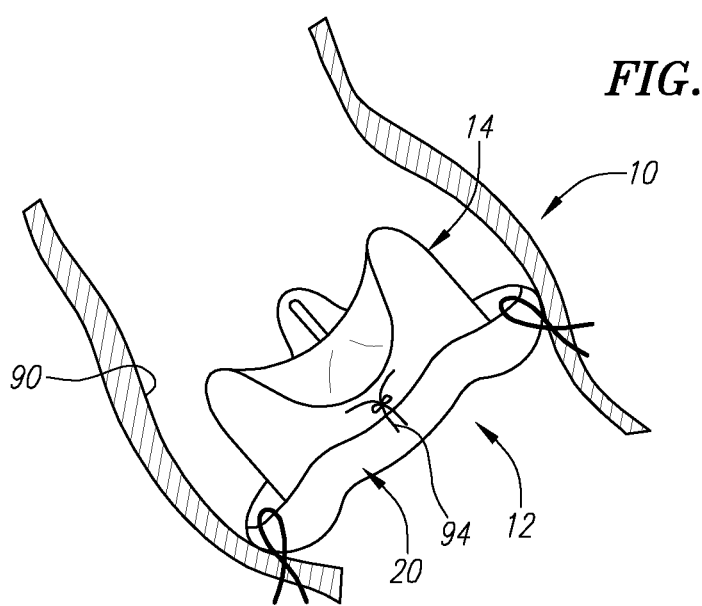

Turning to FIG. 5E, in addition or alternatively, the pilot sutures 94 may be used to secure the crown 14 to the gasket member 12. For example, once the crown 14 is seated sufficiently against the gasket member 12, one or more knots may be directed down each pilot suture 94, similar to knotting procedures used during conventional heart valve replacement. Once sufficient numbers of knots are tied off for each of the pilot sutures 94, the loose portions of the pilot sutures 94 may be cut and removed from the patient's body. In yet another option, clips, staples, or other fasteners (not shown) may be delivered through a portion of the crown 14, which may also penetrate through the gasket member 12, into the surrounding tissue.

Alternatively, if the pilot sutures 94 are eliminated, the crown 14 may be carried into the annulus 90 using a tool (not shown), whereupon the crown 14 may be attached or otherwise secured to the gasket member 12 using any of the methods described herein.

In a further alternative, if the crown 14 does not already include leaflets, leaflets (not shown) may be attached to the crown 14 and/or the base member 12, for example, as disclosed in U.S. Pat. No. 6,371,983, incorporated by reference above. In a further alternative, if the crown 14 is an intermediate connector, a separate valve member (not shown) may be introduced into the annulus 90 and attached to the crown and/or base member. For example, the crown, the base member, and/or the valve member may include guides and/or cooperating connectors for orienting the valve member and/or attaching it to the crown and/or base member, as will be appreciated by those skilled in the art.

Optionally, if it is desirable to remove all or part of the heart valve assembly 10, the crown 14 may be detached and/or removed (not shown) from the base member 12. For example, if the crown 14 is secured by knotting the pilot sutures 94, scissors or another tool (not shown) may be introduced into the annulus 90 to cut the pilot sutures 94. If the fingers/slip knot connectors are used, they may also be cut in a similar manner. In addition or alternatively, if other connectors are used, a tool (not shown) may be introduced into the annulus 90 to disengage the connectors.

Once the pilot sutures 94 are cut and/or other connectors are disengaged, the crown 14 may then be removed from the gasket member 12, e.g., using a holder or other tool (not shown), and withdrawn from the annulus 90. Any interference fit between the crown 14 and gasket member 12 (as described above with reference to FIGS. 2A and 2B, may simply be overcome by applying sufficient force using the holder or other tool. Optionally, the base member 12 may also be removed, e.g., by removing the fasteners 99 securing the base member 12 to the annulus 90.

A replacement crown or an entire heart valve assembly (not shown) may be implanted within the annulus 90 using similar procedures described above for the original crown 14. If pilot sutures are used to deliver and/or secure the crown 14, a plurality of new pilot sutures may be secured through the cuff of the gasket member or through the tissue surrounding the annulus 90, similar to the procedures described above.

Figure 9:
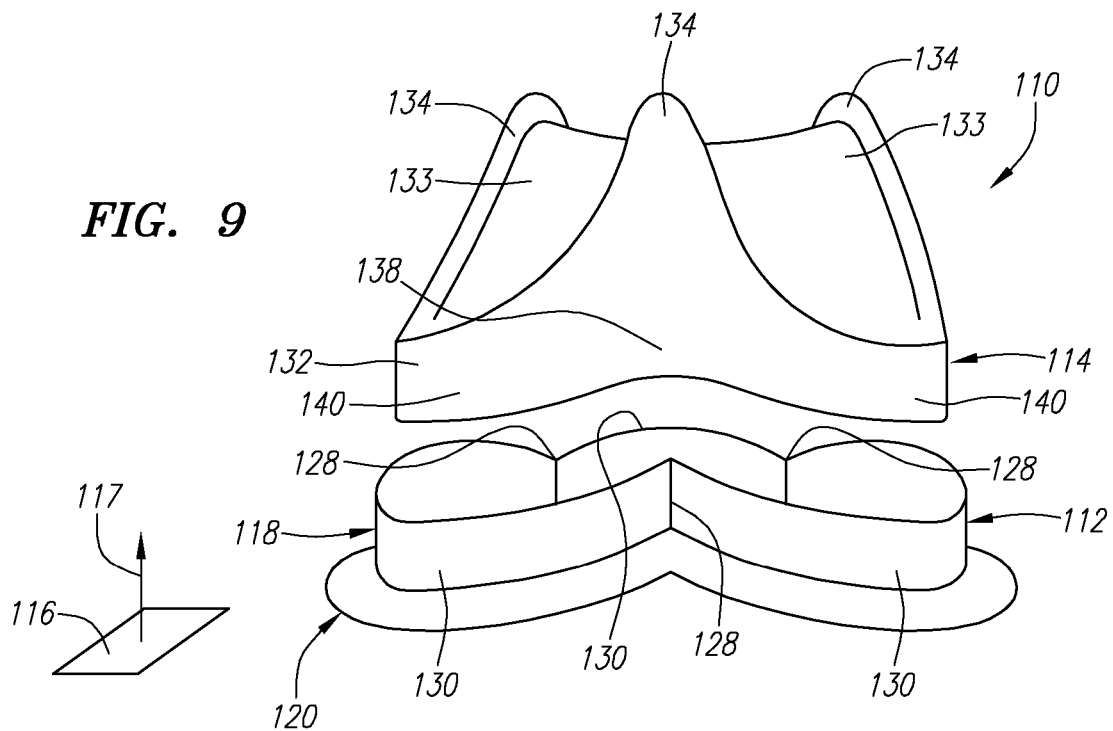
FIG. 9 is a perspective view of another embodiment of a prosthetic heart valve assembly, including a gasket member and a valve member.
Figure 10:
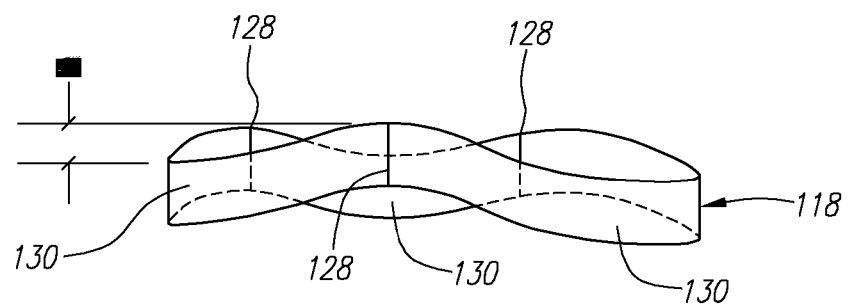
FIG. 10 is a side view of the gasket member of FIG. 9.

Turning to FIGS. 9 and 10, another embodiment of a heart valve assembly 110 is shown that includes a gasket member 112 and a crown 114. Similar to the previous embodiment, the gasket member 112 may include an anchoring ring 118 and a cuff 120, and the crown 114 may a frame 132 and a plurality of leaflets 133. Also, similar to the previous embodiments, the anchoring ring 118 includes a circumference generally defining a plane 116 and a longitudinal axis 117. The anchoring ring 118 may also have a multi-lobular shape about the circumference, including lobes 130 separated by scallops or cusps 128.

Unlike the previous embodiments, the anchoring ring 118 may be biased to have an undulating shape around the circumference that alternately extends above and below the plane 116. In one embodiment, where the anchoring ring 118 has a multi-lobular shape, the lobe portions 130 may extend upwardly out of the plane 116, and the scallop portions 128 may extend downwardly out of the plane 116. For example, the anchoring ring 118 may have a shape corresponding to the commissures and/or nadirs of an annulus of a natural valve that is being replaced. As best seen in FIG. 10, the undulating shape of the anchoring ring 118 may define an amplitude "A" in a relaxed state. The anchoring ring 118 may be sufficient resilient, however, that the amplitude "A" may decrease or increase, e.g., as the lobe portions 130 and/or scallop portions 128 are directed towards or away from the plane 116, as explained further below.

Returning to FIG. 9, the crown 114 generally includes an annular shaped body or frame 132 and one or more valve elements 133. The frame 132 may have a noncircular, e.g., multiple lobular shape, complementary to the gasket member 112. For example, the crown 114 may have a tri-lobular shape, similar to the gasket member 112, including three lobes 140 separated by cusps or scallops 138. The frame 132 may have an undulating shape alternating between adjacent lobe portions 140 and scallop portions 138, defining an amplitude. In one embodiment, in their relaxed states, i.e., when free from external forces, the amplitude of the frame 132 of the crown 114 may be less than the amplitude "A" of the anchoring ring 118 of the gasket member 112.

In an exemplary embodiment, the crown 114 is a prosthetic valve member, i.e., an annular frame 132 carrying a plurality of tissue leaflets 13 extending from the frame 132, e.g., attached to commissures 134. The frame 132 may include a plurality of struts (not shown for clarity), which may be attached to and/or otherwise carry the leaflets, similar to the previous embodiments.

Optionally, the gasket member 112 and/or crown 114 may include one or more detents or other connectors (not shown) for securing the crown 114 to the gasket member 112, similar to the previous embodiments. The gasket member 112 and/or crown 114 may include fabric coverings or other matrices, coatings, and/or guides, also similar to the previous embodiments.

The heart valve assembly 110 may be implanted within a biological annulus, similar to the previous embodiments. Initially, a plurality of pilot sutures may be secured through tissue surrounding the annulus (not shown). For example, a pilot suture may be secured through each of the nadirs of the annulus. With the desired number of pilot sutures secured to the annulus, the gasket member 112 may be advanced into the annulus via the pilot sutures, similar to the previous embodiments. A plurality of fasteners may be directed through the gasket member 112 into the tissue surrounding the annulus to secure the gasket member 112 within the annulus.

To enhance securing the gasket member 112 within the annulus, the pilot sutures may be pulled to apply tension to the tissue through which the pilot sutures are secured, e.g., to open the annulus and/or pull tissue into apposition with the gasket member 112 while the fasteners are delivered. In addition, while tension is applied to the pilot sutures, the scallop portions 128 of the anchoring ring 118 may be drawn upwardly, thereby compressing the gasket member 112 slightly, i.e., reducing the amplitude of the anchoring ring 118.

The crown 114 may then be advanced into the annulus, e.g. via the pilot sutures until the crown 114 contacts the gasket member 112. With the gasket member 112 compressed slightly, the undulating shape of the crown 114 may substantially match the undulating shape of the gasket member 112, which may facilitate docking the crown 114 to the gasket member 112. Similar to the previous embodiments, as the crown 114 is advanced into contact with the gasket member 112 within the annulus, the crown 114 may automatically dock into the gasket member 112, e.g., if cooperating connectors are provided on the crown 114 and gasket member 112. In addition or alternatively, the pilot sutures may be used to secure the crown 114 to the gasket member 112, e.g., by knotting and cutting the pilot sutures, similar to the embodiments described above.

Figure 11:
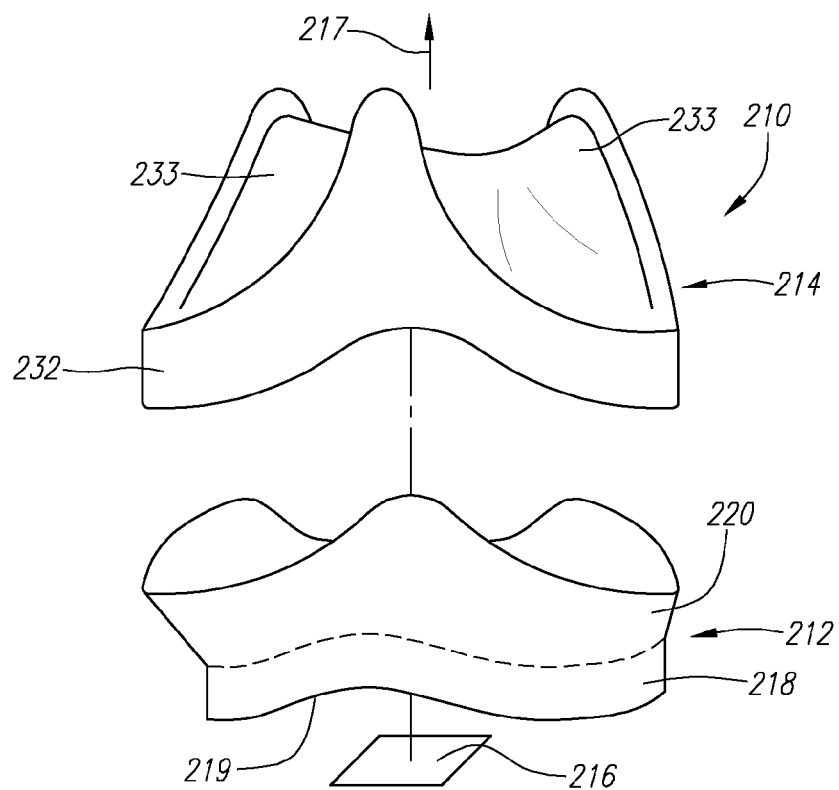
FIG. 11 is a perspective view of yet another embodiment of a prosthetic heart valve assembly, including a gasket member and a valve member.
Figure 12:
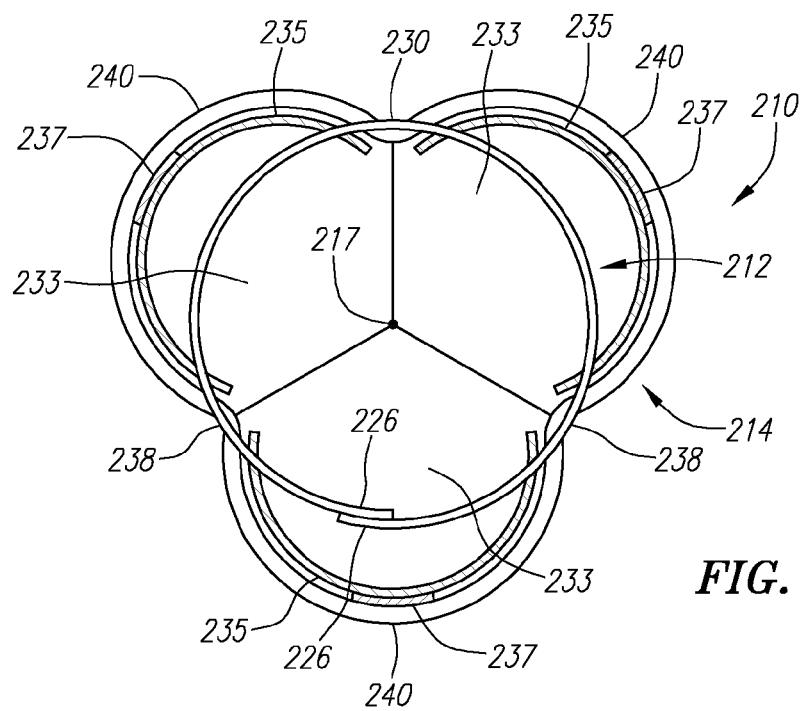
FIG. 12 is a bottom view of the heart valve assembly of FIG. 11 with a sewing cuff and fabric covering omitted for clarity.
Figure 13:
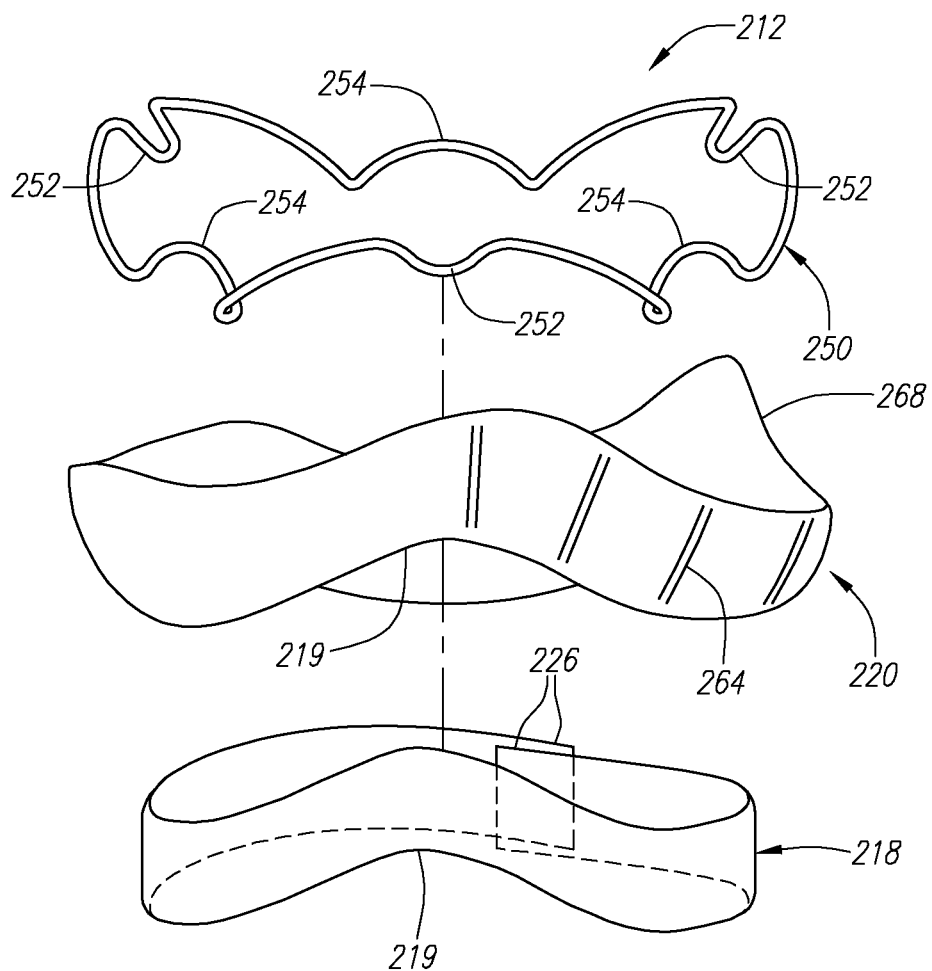
FIG. 13 is an exploded perspective view of the gasket member shown in FIG. 11.
Figure 14:
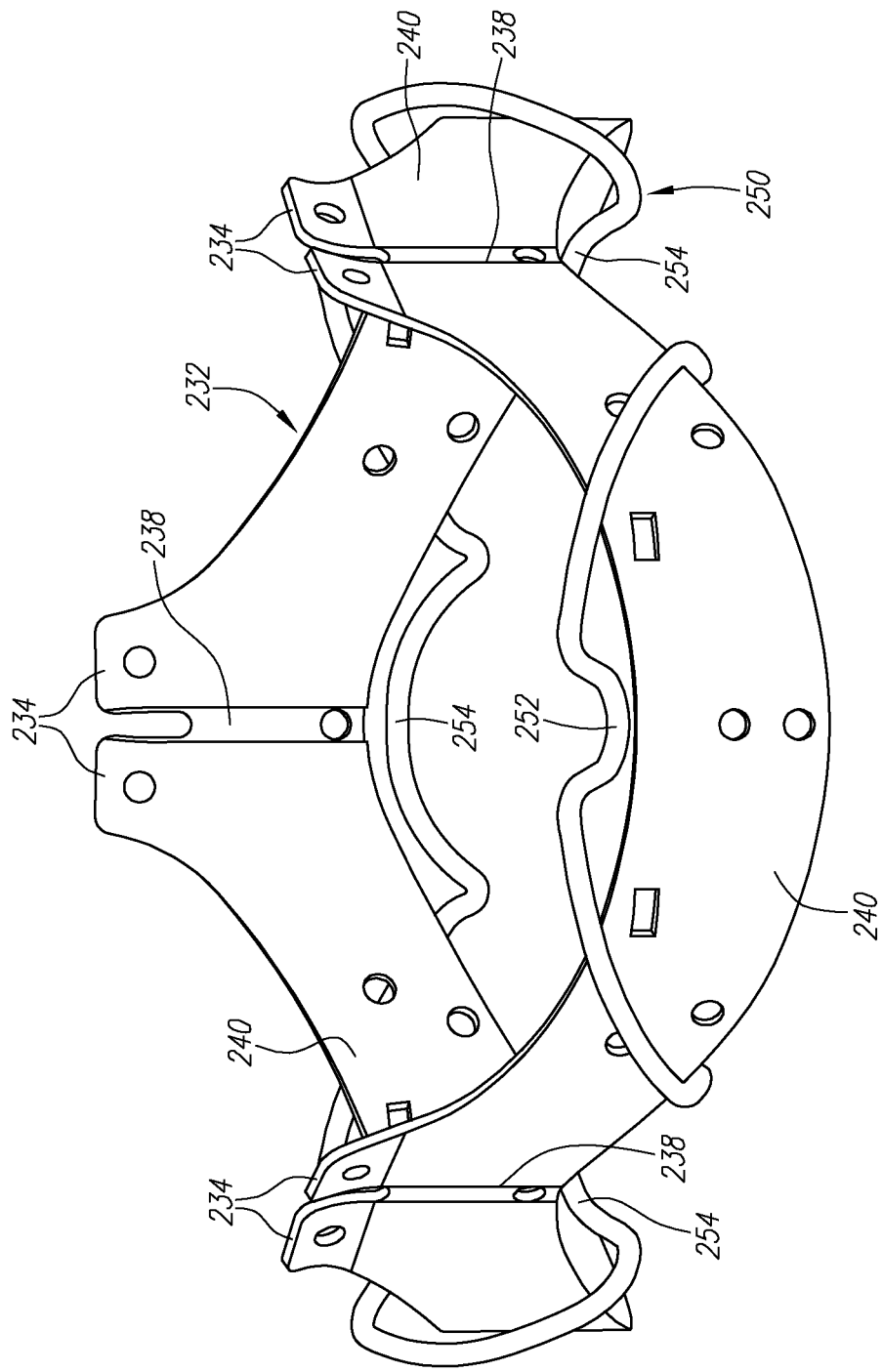
FIG. 14 is a perspective view of a frame of the valve member of FIG. 11 captured by a clip of the gasket member of FIGS. 11 and 13.

Turning to FIGS. 11-13, yet another embodiment of a heart valve assembly 210 is shown that includes a gasket member 212 and a crown 214. Similar to the previous embodiments, the gasket member 212 may include an annular ring 218 and a sewing cuff or ring 220, and the crown 214 may include a frame 232 and a plurality of leaflets 233. Also, similar to the previous embodiments, the annular ring 218 includes a circumference generally defining a plane 216 and a longitudinal axis 217. In addition, similar to the previous embodiments, the gasket member 212 and/or crown 214 may include one or more connectors for securing the crown 214 relative to the gasket member 212. For example, as shown in FIGS. 13 and 14, the gasket member 212 may include a clip 250 that captures or otherwise secures one or more regions of the crown 214, as described further below.

In one embodiment, the annular ring 218 may have a generally circular shape generally parallel to the plane 216, as best seen in FIG. 12, and an undulating shape relative to the longitudinal axis 217 (or in and out of the plane 216), as best seen in FIGS. 11 and 13. For example, as best seen in FIG. 13, the annular ring 218 may include a single undulation 219 at a predetermined location around the circumference of the annular ring 218. The undulation 219 may have rounded edges or blunt angled edges (not shown). As explained further below, the undulation 219 may accommodate implantation of the heart valve assembly 210 without substantial interference with the anterior leaflet of a neighboring mitral valve. Alternatively, the annular ring 218 may include multiple undulations, e.g., three undulations similar to the embodiment described above with reference to FIGS. 9 and 10. In addition or alternatively, the annular ring 218 may have a multi-lobular shape about the circumference, including lobes separated by scallops or cusps (not shown), e.g., similar to the previous embodiments.

With additional reference to FIG. 13, the annular ring 218 may be expandable and/or contractible such that the diameter (or other cross-section if the annular ring 218 is non-circular) may be adjusted, e.g., based upon the anatomy of the patient encountered during a procedure. In one embodiment, the annular ring 218 may biased to expand to a predetermined diameter. Thus, the annular ring 218 may be contracted radially to a smaller diameter, e.g., to facilitate delivery into an annulus, yet may be resiliently expandable to dilate tissue surrounding the annulus and/or to facilitate securing the gasket member 212 within the annulus.

For example, as shown, the annular ring 218 may be an open band including overlapping ends 226 that may slide relative to one another to accommodate expansion and/or compression. The annular ring 218 may be sized such that, in a relaxed state (free from any outside forces), the annular ring 218 may have a predetermined diameter slightly larger than the dilated cross-section of a tissue annulus, e.g., between about nineteen and thirty millimeters (19-30 mm), or between about twenty three and twenty five centimeters (23-25 cm). In the relaxed state, the ends may remain overlapped at least partially, or, alternatively, the ends may be spaced apart such that the annular ring 218 has a "C" shape.

In one embodiment, the overlapping ends 226 may be substantially smooth or otherwise free from any protrusions to facilitate their sliding relationship. In addition or alternatively, the ends 226 may include one or more cooperating elements (not shown) for limiting relative movement of the ends. For example, the cooperating elements may limit the annular ring 218 to expand and/or contract within a predetermined range of diameters. Exemplary cooperating elements that may be provided are disclosed in co-pending application Ser. No. 10/327,821, incorporated by reference above.

Figure 13A:
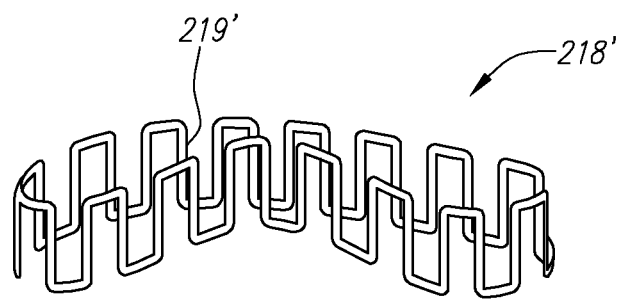
FIG. 13A is a perspective view of an alternative embodiment of an annular ring that may be included in the gasket member of FIGS. 11-13.

Alternatively, the annular ring may be a substantially enclosed band that may be resiliently compressed to a smaller diameter. For example, as shown in FIG. 13A and described further below, the annular ring 218' may be formed from a plurality of sinusoidal elements 219' connected end-to end about the circumference of the annular ring 218.' The annular ring 218' may be formed as a continuous band, e.g., by laser cutting, mechanical cutting, etching, or otherwise forming a tube into the annular ring 218.' Alternatively, the sinusoidal elements 219' may be formed from a flat band, e.g., by laser cutting, mechanical cutting, etching, and the like, and the loose ends of the sinusoidal elements 219' may be attached to one another, e.g., by welding, interference fit, adhesives, connectors, and the like, after the band is rolled into the annular ring 218.'

The sinusoidal elements 219' may be resiliently compressed by a radially compressive force, i.e., to reduce the distance between adjacent sinusoidal elements 219,' to reduce the diameter of the annular ring 218.' This reduced diameter configuration may facilitate introduction of the annular ring 218' into a biological annulus. When the force is removed, the sinusoidal elements 219' may resiliently expand to increase the diameter, e.g., until the annular ring 218' is secured within a tissue annulus. Optionally, the annular ring 218' may be sufficiently biased to at least partially dilate the biological annulus, i.e., direct tissue surrounding the biological annulus radially outwardly to maximize the open area of the biological annulus.

Returning to FIGS. 11 and 13, as shown, the annular ring 218 has a substantially straight or cylindrical wall, e.g., extending substantially parallel to the longitudinal axis 217. A substantially straight wall may accommodate implantation within the tissue annulus of the native valve being replaced, e.g., allowing the wall of the annular ring 218 to dilate and/or retain the tissue surrounding the annulus during and after implantation of the heart valve assembly 210. Alternatively, the annular ring 218 may have a tapered shape, e.g., being wider on its upper or lower edge (not shown). For example, if the annular ring 218 has a larger diameter about the upper edge than the lower edge to define a frusto-conical shape that may accommodate implantation supra-annularly, i.e., at least partially above the tissue annulus. In further alternatives, the wall of the annular ring 218 may include a substantially straight portion and a tapered portion, similar to the embodiments disclosed in application Ser. No. 10/327,821, incorporated by reference above.

The annular ring 218 may be formed from an elastic or superelastic material, such as Nitinol, or any of the other materials described elsewhere herein. For example, the annular ring 218 may be cut from a flat sheet of base material having a desired thickness for the annular ring 218, e.g., between about 0.1-0.5 millimeters, for example, by laser cutting, mechanical cutting, and the like. Thus, the annular ring 218 may be initially formed as a long band of material, having a width corresponding to the desired width of the annular ring 218, e.g., between about 1.5-2.5 millimeters, and a length corresponding to a desired circumference of the annular ring 218, e.g., between about 55-90 millimeters. Optionally, the undulation(s) 219 may be formed as the band is cut out of the flat sheet. Alternatively, the undulation(s) 219 may be formed in the band after cutting, e.g., by plastically deforming the band material and/or heat setting the undulation(s) 219 into the band.

The band may then be wrapped around a mandrel or otherwise restrained in a generally cylindrical shape with the ends 226 adjacent to one another, and the band may be heat treated or otherwise processed to program the generally cylindrical shape to create the annular ring 218. The generally cylindrical shape may include the ends 226 overlapping one another, as shown in FIGS. 12 and 13, or spaced apart from one another to provide an open "C" shape (not shown). Optionally, a tapered shape may also be formed in one or more portions of the annular ring 218, e.g., based upon the shape of the band cut from the base material and/or by heat treating the material once restrained in the tapered shape (which may be simultaneous or separate from heat setting the band in the generally cylindrical shape).

When the annular ring 218 is at least partially covered with fabric (not shown), the fabric may be wrapped around the annular ring 218, while accommodating expansion and contraction of the annular ring 218. For example, at least near the ends 226, the fabric may not be secured to the annular ring 218, allowing the ends 226 to slide circumferentially relative to the fabric. Optionally, sutures and the like (not shown) may be used to secure the fabric to the annular ring 218 at locations removed from the ends 226, e.g., at an intermediate location about the circumference of the annular ring 218. Alternatively, the entire annular ring 218 may be free to slide within the fabric wrapped around the annular ring 218.

Returning to FIGS. 11 and 12, the sewing cuff 220 may be attached to or otherwise extend around the annular ring 218. The sewing cuff 220 may simply be a layer of fabric or other material covering at least a portion of the annular ring 218. For example, a layer of fabric (not shown) may cover all of the annular ring 218 (other than any connectors and/or bearing surfaces, if any) and/or may include a section of material extending radially outwardly from the annular ring 218, similar to the previous embodiments. Optionally, the sewing cuff 220 may include flexible core material that may be attached to or otherwise extend around the annular ring 218.

Figure 15A:
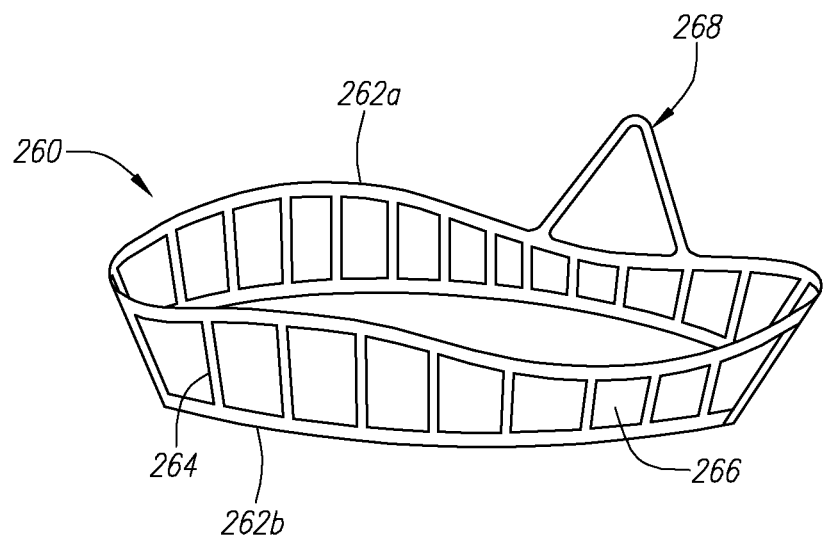
FIGS. 15A and 15B are perspective views of alternate embodiments of a core that may be provided within a sewing cuff for a heart valve assembly.
Figure 15B:
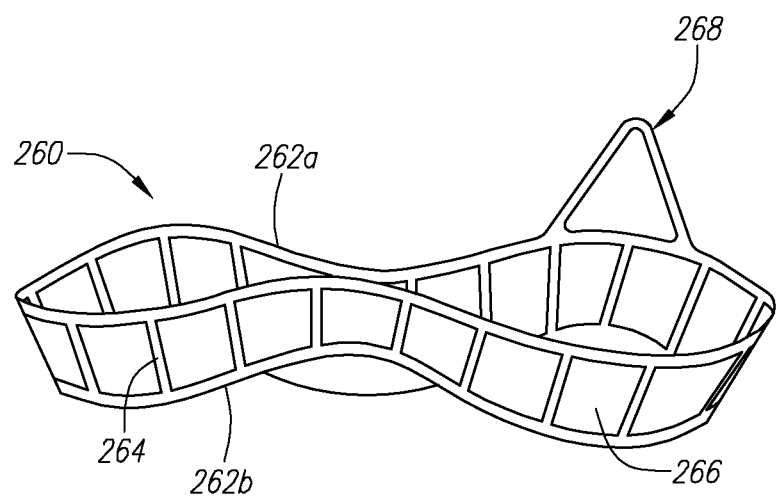

Turning to FIGS. 15A and 15B, exemplary embodiments of a flexible core 260 are shown that include a lattice extending around a circumference of the core 260. As shown, the lattice includes at least two spaced apart circumferential elements 262 and a plurality of ribs or transverse elements 264 extending between the circumferential elements 262, thereby defining openings 266 through the lattice. The openings 266 may be completely open, i.e., free from any material. Alternatively, the openings 266 may be recesses including a relatively thin wall of core material, i.e., that is substantially thinner than the circumferential elements 262 and/or ribs 264. For example, the circumferential elements 262 and/or ribs 264 may have a thickness between about 0.001-0.005 mm, while the openings 266 may have a wall thickness of not more than about half that of the circumferential elements 262 and/or ribs 264. In an exemplary embodiment, the openings 266 may have a thickness not more than about half that of the circumferential elements 262 and/or ribs 264. Alternatively, the lattice may include only the circumferential elements 262 or ribs 264 with thin wall openings extending between adjacent elements (not shown).

In a relaxed state (free from external forces), the core 260 may adopt a generally planar annular shape, as shown in FIG. 15A. Alternatively, in a relaxed state, the core 260 may adopt an undulating annular shape, as shown in FIG. 15B. The core 260 may also be tapered, as shown in FIGS. 15A and 15B, e.g., having a larger diameter or circumference about an upper circumferential element 262a than about a lower circumferential elements 262b. The tapered shape of the core 260 may define an angle relative to the longitudinal axis 217, e.g., between about twenty and forty five degrees (20-45°).

The material of the core 260 may be substantially flexible, e.g., manufactured in a desired annular shape (such as those just described), yet easily deformed, e.g., deflected, stretched, and/or compressed. The core 260 may be sufficiently flexible to be "floppy," i.e., such that the core 260 conforms easily and substantially based upon the particular anatomy and/or implantation arrangements encountered during implantation. Thus, when the sewing cuff 220 is placed above or within a tissue annulus within a patient's heart, the core 260 may conform to the surrounding anatomy and/or may deform when the crown 214 is secured to the gasket member 212, e.g. to enhance sealing between the crown 214 and the gasket member 212.

For example, when implanted within or above a tissue annulus, the core 260 may lie against the surrounding tissue, thereby changing its shape from its original generally circular or multi-lobular shape, changing the shape of any undulations, and/or changing the angel of the original taper. Thus, the core 260 may become more vertical or inward when it lies against the commissures (not shown) of the tissue annulus, and become more horizontal or outward when it lies within the sinuses above and between the commissures. When fasteners (not shown) are driven through the sewing cuff 220, the core 260 may resiliently stretch or compress to distribute forces from the fasteners more evenly, which may reduce bunching of the sewing cuff 220 or other distortions that may otherwise result in leakage, as explained further below.

Exemplary materials for the core 260 include silicone or other elastomeric materials, foam, fabric, felt, polymers, and the like. In addition or alternatively, the core 260 may include swellable material, e.g., foam or sponge materials that may expand when exposed to fluid, such as blood. The materials may be molded or otherwise formed into the core 260, e.g., using known molding, extrusion, cutting, or other manufacturing procedures. For example, the core 260 may be injection molded or otherwise formed in its annular shape. Alternatively, the core 260 may be molded or otherwise formed as a flat sheet, and rolled into the annular shape. In this alternative, the ends of the sheet may be attached to one another, e.g., using sutures, adhesives, ultrasonic welding, and the like. Optionally, to provide a tapered shape, one or more wedges (not shown) may be cut out of the band to provide a desired tapered but annular shape.

Optionally, the core 260 may include one or more ears 268, which may extend from one of the circumferential elements 262. For example, as shown, a single ear 268 extends upwardly from upper circumferential elements 262a. The ear(s) 268 may be provided at a predetermined location about the circumference of the core 260 (and consequently, the gasket member 212), e.g., to provide a visual and/or tactile marker, as explained further below.

In another option, portions of the core 260 may be disconnected from other portions, e.g., to prevent puckering. For example, if the core 260 is formed from a rolled sheet (not shown), ends of the sheet (also not shown) may remain loose to allow the ends to move relative to one another. In addition or alternatively, the circumferential elements 262 may be severed, e.g., vertically, and/or individual ribs 264 may be partially cut or otherwise separated from adjacent ribs 264. These features may allow localized strain on elements of the core 260, which may prevent puckering or otherwise enhance sealing between the core 260 and surrounding tissue.

Figure 16:
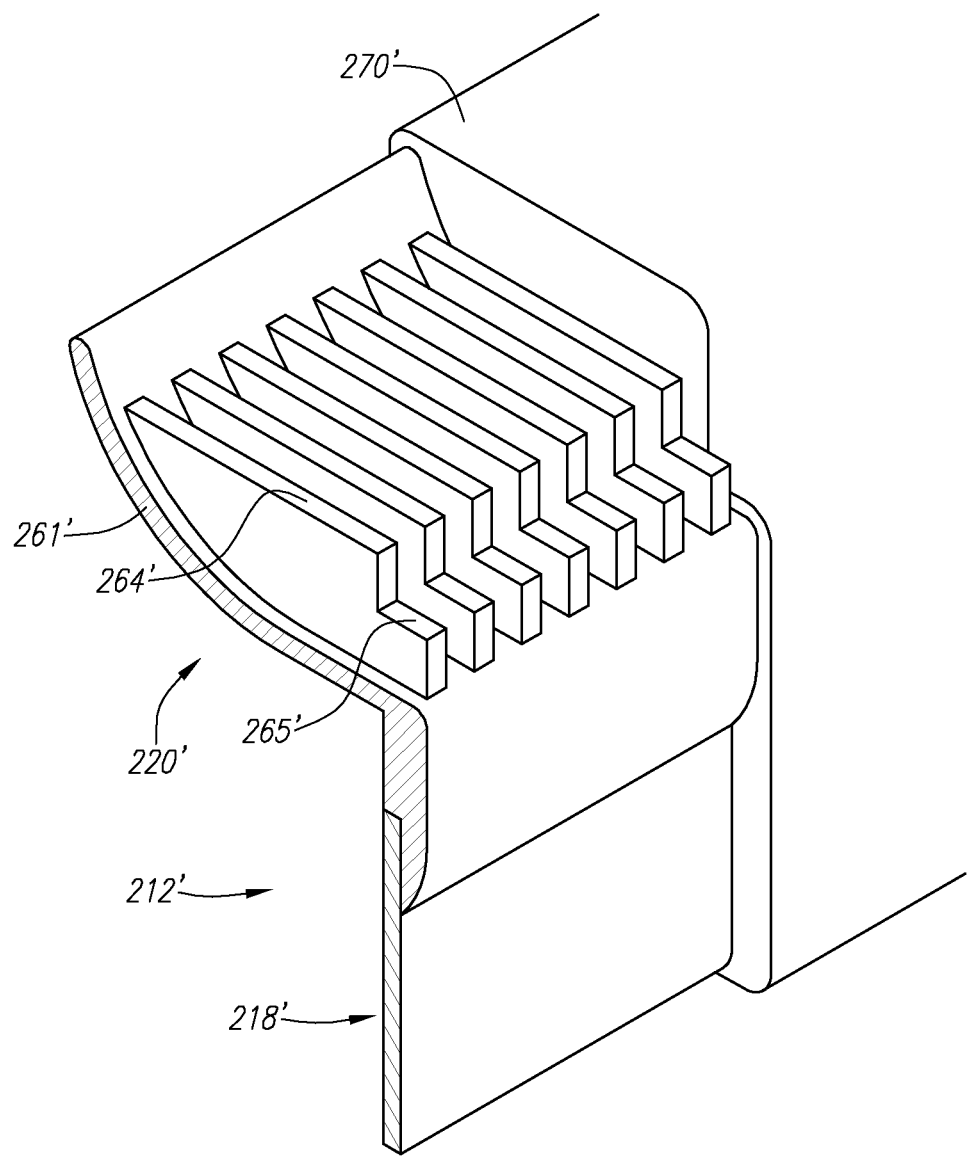
FIG. 16 is a perspective detail of a gasket member for a heart valve assembly with an overlying fabric covering partially removed.

Turning to FIG. 16, another embodiment of a sewing cuff 220' is shown that includes a core 260' extending from an annular ring 218' of a gasket member 212.' The core 260' includes a base or web 261' from which a plurality of ribs 264' extend. As shown, the ribs 264' extend only from an upper surface of the base 261,' e.g., generally upwardly. In addition or alternatively, ribs (not shown) may also extend from a lower or outer surface of the base 261,' e.g., generally downwardly and/or outwardly. The ribs 264' may be relatively narrow, thereby enhancing the flexibility of the ribs.'

The base 261' and ribs 264' may be integrally formed together, e.g., as a single molded component from silicone or other materials, similar to the previous embodiments. A lower edge of the base 261' may be attached to the annular ring 218,' e.g., by chemical bonding, heat bonding, interference fit, molding, and the like. The lower edge of the base 261' may be relatively thick and/or rigid, e.g., to support the ribs 264,' while the rest of the base 261' may be relatively thin, e.g., to provide flexibility for the base 261' such that the base 261' can conform to the surrounding anatomy encountered, similar to the previous cores 260, described with reference to FIGS. 15A and 15B. As shown in FIG. 16, the base 261' and ribs 264' may be covered with a fabric covering 270' to provide the sewing cuff 220.' The fabric covering 270' may also extend over the annular ring 218,' e.g., to substantially cover all of the exposed surfaces of the gasket member 212,' e.g., to encourage tissue ingrowth. If the annular ring 218' is expandable, the fabric covering 270' may not be connected to all or portions of the annular ring 218' to accommodate expansion and contraction, similar to the previous embodiments.

Optionally, as shown in FIG. 16, the ribs 264' may include notches 265' that may define a rim or other peripheral border corresponding, for example, to the size and/or shape of a crown (not shown) that may be secured to the gasket member 212.' When a crown is advanced against the sewing cuff 220,' the frame (also not shown) of the crown may engage or be received by the notches 265.' The ribs 264' may be resiliently compressed between the base 261' and the crown, e.g., to substantially fill any spaces between the base 261' and the crown, which may enhance sealing between the crown and the gasket member 212.'

Returning to FIGS. 11 and 12, the crown 214 generally includes an annular shaped body or frame 232 and one or more leaflets or other valve elements 233. With additional reference to FIG. 14, the frame 232 may have a noncircular, e.g., multiple lobular shape, for example, a tri-lobular shape, including three lobes 240 separated by cusps or scallops 238. The frame 232 may have an undulating shape alternating between adjacent lobe portions 240 and scallop portions 238, e.g., such that the lobe portions 240 are lower than the scallop portions 238, similar to the previous embodiments. In addition, the frame 232 may include commissures 234.

As shown in FIG. 12, the frame 232 may include a plurality of struts 235 (which may be single piece or laminate structures, not shown) that may be attached to and/or otherwise carry the leaflets 233, e.g., using sutures and the like (not shown), similar to the previous embodiments. The struts 235 may be attached to the frame 232 by spacers 237 that may anchor an intermediate region of the struts 235 to the frame 232, while allowing ends of the struts 235 to move to open and close the leaflets 233, similar to the valves disclosed in U.S. Pat. No. 6,371,983, incorporated by reference above. The struts 235, spacers 237, and frame 232 may be connected to one another, e.g., by cooperating detents, such as tabs and mating pockets (not shown), and/or by mechanical or chemical bonding.

Optionally, the gasket member 212 and/or crown 214 may include one or more connectors for securing the crown 214 to the gasket member 212, similar to the previous embodiments. The gasket member 212 and/or crown 214 may also include fabric coverings or other matrices, coatings, and/or guides, also similar to the previous embodiments.

For example, as best shown in FIGS. 13 and 14, the gasket member 212 may include a clip 250 for securing the crown 214 relative to the gasket member 212. The clip 250 may include a plurality of tabs or other securing elements 252, 254 that engage at least a portion of the crown 214. For example, the clip 250 may generally define a diameter or other cross-section that is larger than the frame 232 of the crown 214. Upper tabs 252 may extend inwardly from the clip 250, e.g., at locations corresponding to the lobes 240 of the frame 232, while lower tabs 254 extend inwardly from the clip 250, e.g., at locations corresponding to the scallops 248 of the frame 232. The upper tabs 252 may be angled downwardly, e.g., to define angled upper surfaces.

The clip 250 may be secured to the annular ring 218 and/or sewing cuff 220 of the gasket member 212 to provide a single, integral component. For example, one or more portions, e.g., regions adjacent the lower tabs 254, of the clip 250 may be captured by the fabric covering (not shown) that covers the annular ring 218 and/or sewing cuff 220. In addition or alternatively, one or more sutures (not shown) may be used to tie the clip 250 to the annular ring 218 and/or sewing cuff 220. In further alternatives, the clip 250 may be attached to the annular ring 218 and/or sewing cuff 220 by bonding with an adhesive, welding, interference fit, and the like.

With particular reference to FIG. 14, during implantation, as the frame 232 of the crown 214 is advanced downwardly towards the clip 250, the lower edge of the frame 232 may contact the angled upper surfaces of the upper tabs 252. As the frame 232 is advanced further, the upper tabs 252 may slide radially outwardly, because of the angled upper surfaces until the frame 232 clears and passes below the upper tabs 252 and contacts the lower tabs 254. The tabs 252 may then resiliently deflect back inwardly, thereby passing above the frame 232. The frame 232 is thus captured between the upper and lower tabs 252, 254, thereby securing the crown 214 relative to the gasket member 212. Alternatively, the crown 214 may be angled relative to the gasket member 212 to allow a portion of the frame 232 to be received under one or more of the upper tabs 252, and then the remainder of the frame 232 may be pushed under the remaining upper tabs 252, similar to the methods described further below.

The clip 250 may be formed from an elongate wire bent or otherwise shaped into the shape shown, whereupon its ends may be attached to one another, e.g., by welding, mechanical bonding, chemical bonding, mating connectors, and the like. Alternatively, the clip 250 may be cut or otherwise formed from a flat sheet of material as an enclosed loop that may also be bent or otherwise shaped into the shape shown. In a further alternative, the clip 250 may be formed from a band of material cut from a sheet that may be shaped into the shape shown, whereupon its ends may be attached to one another, similar to the wire. The clip 250 may be formed from an elastic or superelastic material, such as Nitinol, that may be heat treated to set the final shape into the clip material. Thus, the clip material may allow the upper tabs 252 of the clip 250 to deform outwardly as the frame 232 is advanced against the clip 250, yet resiliently return inwardly to substantially securely engage the frame 232. After the clip 250 has been formed, the clip 250 may be secured to the annular ring 218 and/or sewing cuff 220 to create the gasket member 212.

To make the heart valve assembly 210 of FIG. 11, the components, e.g., the annular ring 218, frame 232, struts 235, spacers 237, and clip 250 may be formed, e.g., using the methods and materials described elsewhere herein. If the sewing cuff 220 includes a core 260, the core 260 may also be formed, e.g., using the methods and materials described above. The annular ring 218, core 260, and clip 250 may be assembled together, as described above, e.g., using sutures and/or by wrapping one or more fabrics or other covering over and/or around exposed surfaces of the annular ring 218 and core 260, and/or around portions of the clip 250. When assembled, the core 260 may be substantially covered with fabric to provide the sewing cuff 220, which extends radially from the annular ring 218. In one embodiment, the sewing cuff 220 extends from an upper edge of the annular 218, e.g., for intra-annular placement of the annular ring 218 and supra-annular placement of the sewing cuff 220. Alternatively, the sewing cuff 220 may extend from a lower edge or intermediate region of the annular ring 218 (not shown) for other implantation configurations.

Returning to FIG. 11, the heart valve assembly 210 may be implanted within a biological annulus, similar to the previous embodiments. With the annular ring 218 contracted into a relatively small diameter (if the annular ring 218 is radially compressible), the gasket member 212 may be advanced into the annulus using a delivery tool (not shown). The gasket member 212 may be advanced until the annular ring 218 extends at least partially into the biological annulus. In one embodiment, the annular ring 218 extends entirely through the biological annulus, with the lower edge of the annular ring 218 remaining free within the sub-annular space below the biological annulus. The sewing cuff 220 may contact the tissue within the supra-annular space above the biological annulus, although the sewing cuff 220 may not provide any structural support of the annular ring 218.

If the annular ring 218 is expandable or otherwise compressed, the annular ring 218 may then be expanded within the biological annulus, e.g., to dilate the biological annulus or otherwise direct the surrounding tissue outwardly against the underlying tissue structures. For example, the annular ring 218 may simply be released by the delivery tool, whereupon the annular ring 218 may resiliently expand against the tissue surrounding the biological annulus, thereby substantially securing the annular ring 218 (and consequently, the gasket member 212) relative to the biological annulus. In addition or alternatively, a dilation tool (not shown) may be advanced into the gasket member 212 and expanded to forcibly (e.g., plastically) expand the annular ring 218 within the biological annulus. An exemplary dilation tool that may be used is shown in co-pending application Ser. No. 10/327,821, incorporated by reference above.

If the sewing cuff 220 is restrained by the delivery tool, the sewing cuff 220 may be released to allow the sewing cuff 220 to contact the surrounding tissue, e.g., within the aortic root above the biological annulus. Because of the floppy (i.e., flexible and conformable) nature of the core 260, the sewing cuff 220 may adopt the shape of the surrounding tissue, e.g., lying flatter within the coronary sinus regions, while becoming more vertical adjacent the commissures.

If the sewing cuff 220 includes an ear 268, the gasket member 212 may be angularly aligned in a predetermined manner during advancement into the biological annulus. For example, if the sewing cuff 220 includes a single ear 268, the ear 268 may be aligned with the commissure between the right coronary and non-coronary sinus cusps (the RC/NC commissure). Consequently, the ear 268 may provide a visual and/or tactile marker for the surgeon, identifying the location of underlying nerves in the RC/NC commissure region. In addition or alternatively, if the annular ring 218 includes an undulation 219, the gasket member 212 may be angularly aligned to position the undulation 219 above the commissure between the left coronary sinus and non-coronary sinus cusps (the LC/NC commissure). The undulation 219 may thereby provide clearance for the anterior mitral leaflet to avoid interference with the mitral valve. If the gasket member 212 includes both the ear 268 and the undulation 219, the ear 268 and undulation 219 should be angularly aligned relative to one another such that the ear 268 is aligned with the RC/NC commissure when the undulation 219 is aligned with the LC/NC commissure.

With the gasket member 212 in place, a plurality of fasteners, e.g., clips, staples, sutures, and the like, may be directed through the sewing cuff 220 into the tissue surrounding the biological annulus to secure the gasket member 112 relative to the biological annulus. If the sewing cuff 220 includes ribs (not shown) on a lower surface of a core 260, the ribs may be compressed at least partially between the sewing cuff 220 and the surrounding tissue to enhance sealing. Optionally, the core 260 may swell when exposed to fluid to enhance sealing of the sewing cuff 220. In addition or alternatively, material may be injected into the sewing cuff 260, e.g., using a syringe and the like (not shown), or otherwise applied to an exterior or interior of the sewing cuff 260, e.g., to fill any gaps or puckers that may result after the fasteners are delivered. Exemplary materials that may be injected include silicone or other polymers, which may expand upon delivery to enhance sealing.

The crown 214 may then be advanced into the biological annulus, e.g. using another delivery tool or the same tool (not shown) used to deliver the gasket member 212, and angularly aligned with the gasket member 212. As the crown 214 is advanced towards the gasket member 212, the frame 232 of the crown 214 may engage the clip 250, as described above, thereby securing the crown 214 to the gasket member 212. If the sewing cuff 220 includes ribs (not shown) on the core 260 that extend upwardly, the ribs may be compressed between the frame 260 and the sewing cuff 220 to also enhance sealing. Any tools may be removed, and the procedure completed using known methods, similar to the previous embodiments. Optionally, the crown 214 may include a flexible skirt that may enhance sealing with the sewing cuff 220. The flexible skirt may include a core (not shown), similar to the sewing cuff 220 described above. In addition or alternatively, additional sealing material may be injected or otherwise applied to the skirt to enhance sealing.

Turning to FIGS. 17A-19, yet another embodiment of a heart valve assembly 310 is shown that includes a gasket member 312 and a crown 314, which may be at least partially covered by one or more pieces of fabric or other material 336, 370 (not shown in some drawings for clarity), similar to other embodiments described herein. Generally, the gasket member 312 includes an annular ring 318, a flexible baleen element 330, and a sewing cuff or ring 320, and the crown 314 includes a frame 332, and a plurality of leaflets 333 carried by struts 335. The annular ring 318 and/or crown 314 generally include a circumference or other periphery extending generally parallel to a plane 316 and transverse to a longitudinal axis 317.

Similar to the previous embodiments, the gasket member 312 and/or crown 314 may include one or more connectors for securing the crown 314 relative to the gasket member 312. For example, as shown in FIG. 17B, the gasket member 312 may include a clip 350 that captures or otherwise secures one or more regions of the crown 314, e.g., between tabs 352, 354, similar to the previous embodiments. In addition or alternatively, one or more other connectors (not shown), such as the other embodiments described elsewhere herein, may be provided for securing the crown 314 to the gasket member 312.

Figure 18:
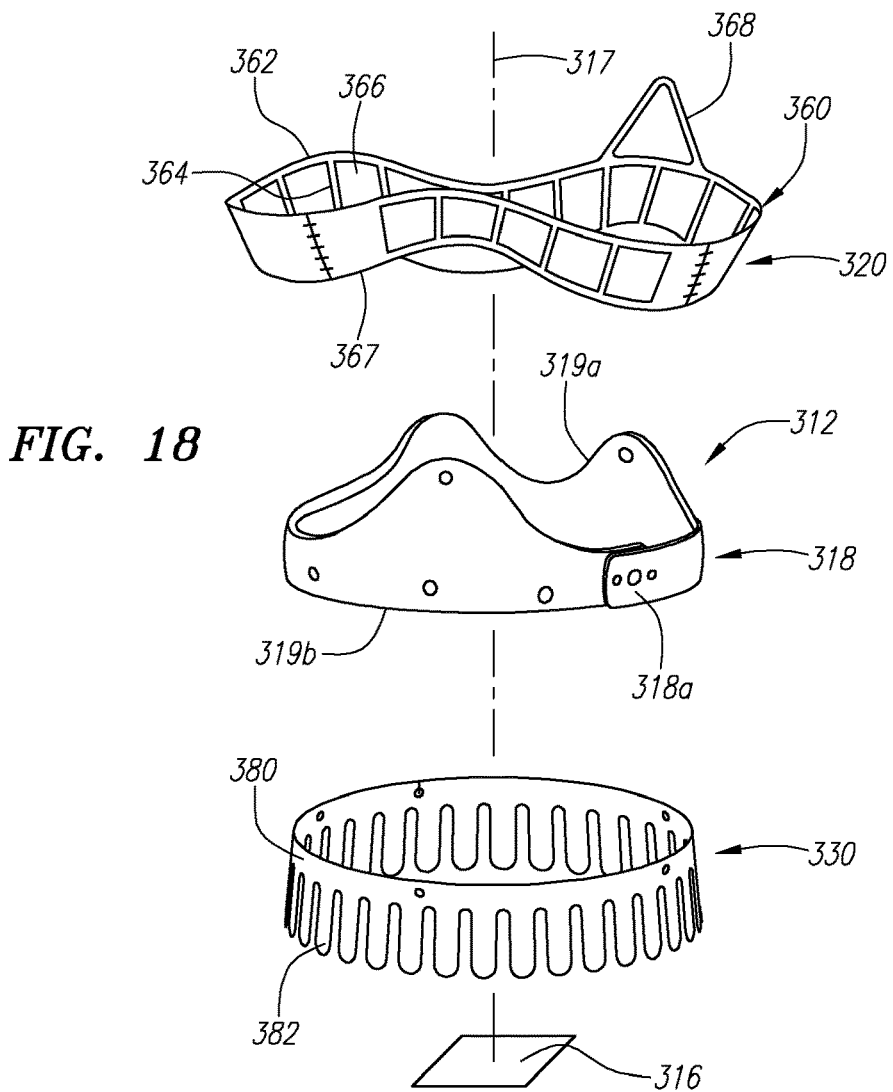
FIG. 18 is an exploded perspective view of the gasket member of FIGS. 17A and 17B with the fabric covering removed for clarity.

In one embodiment, the annular ring 318 may have a substantially circular shape generally parallel to the plane 316, as best seen in FIG. 18. In addition, the annular ring 318 may have an undulating shape relative to the longitudinal axis 317. For example, an upper edge 319a of the annular ring 318 may include one or more undulations, e.g., three undulations corresponding to the tri-lobular shape of the sinus cavity or supra-annular space above a biological annulus. In addition or alternatively, a lower edge 319b may include at least one undulation (not shown), e.g., corresponding to a location of the anterior leaflet of a neighboring mitral valve, similar to the previous embodiments. In a further alternative, the annular ring 318 may have a multi-lobular shape about the circumference, e.g., including lobes separated by scallops or cusps (not shown), similar to the previous embodiments.

With additional reference to FIG. 18, the annular ring 318 may include overlapping edges 318a that are secured to one another, e.g., by resistance welding, ultrasonic welding, adhesives, fasteners, and the like. Alternatively, the overlapping edges 318a may be movable relative to one another (not shown), e.g., allowing the annular ring 318 to expand and/or contract such that the diameter (or other cross-section if the annular ring 218 is noncircular) may be adjusted, similar to the previous embodiments. In another alternative, the annular ring 318 may be a substantially enclosed band that may be resiliently compressed to a smaller diameter, e.g., formed from a plurality of sinusoidal elements (not shown) connected end-to end about the circumference of the annular ring, similar to the annular ring 218' shown in FIG. 13A and described elsewhere herein.

The annular ring 318 may have a substantially straight or cylindrical wall, e.g., extending substantially parallel to the longitudinal axis 317, as shown. Alternatively, at least a portion of the annular ring 318 may have a tapered shape, e.g., being wider on its upper or lower edge (not shown), similar to other embodiments described herein. The annular ring 318 may be formed from elastic or superelastic material, such as Nitinol, and/or using any of the other materials and methods described elsewhere herein.

As best seen in FIG. 18, the sewing cuff 320 may include a flexible core 360, e.g., including a lattice extending around a circumference of the flexible core 360. As shown, the flexible core 360 includes an upper circumferential element 362 and a plurality of ribs or transverse elements 364 extending generally vertically from the circumferential element 362, thereby defining openings 366. The openings 366 may be recesses including a relatively thin wall of core material, i.e., that is substantially thinner than the circumferential element 362 and/or ribs 364, similar to the previous embodiments. Alternatively, the openings 366 may be completely open, i.e., extending completely through the flexible core 360 such that the openings 366 are free from any material. In addition or alternatively, the flexible core 360 may include a lower circumferential element (not shown), e.g., similar to the embodiment shown in FIG. 15A. Optionally, the flexible core 360 may also include one or more ears 368 (one shown), which may extend from the upper circumferential element 362.

In a relaxed state, the core 360 may be tapered, e.g., having a larger diameter or circumference about the upper circumferential element 262 than about its lower edge 367. The core 360 may adopt an undulating annular shape, e.g., including three undulations, or may have a generally planar shape. The material of the core 360, e.g., silicone or other elastomeric materials, foam, felt, polymers, and the like, may be substantially flexible, yet may be easily deformed, e.g., deflected, stretched, and/or compressed. Thus, when the sewing cuff 320 is placed above or within a tissue annulus within a patient's heart, the core 360 may conform at least partially to the surrounding anatomy and/or may deform when the crown 314 is secured to the gasket member 312, e.g. to enhance sealing between the crown 314 and the gasket member 312. Optionally, the core 360 may be attached to the annular ring 318, e.g., along the upper edge 319a. For example, the core 360 may be fused along the upper edge 319a, e.g., by softening or melting the core material, or attached using adhesives, an interference fit, one or more fasteners (not shown), and the like. Alternatively, the core 360 may be butted against the annular ring 318 or otherwise disposed adjacent the upper edge 319a, and held in relative position by the fabric covering 370, one or more sutures or other fasteners (not shown), and the like.

With continued reference to FIGS. 17A-19, the baleen element 330 may be an annular member including a plurality of flexible fingers 382 extending from a base 380. The base 380 may have a diameter corresponding substantially to the annular ring 318, e.g., such that the base 380 may be disposed around the annular ring 318. Optionally, the base 380 may be secured to the annular ring 318, e.g., by one or more of an interference fit, adhesive, ultrasonic welding, one or more fasteners, and the like. The fingers 382 may be biased to extend outwardly from the base 380, thereby defining a frusto-conical shape, as shown in FIG. 18. For example, the baleen element 330 may be biased to an angle of between about one and ten degrees (1-10°) relative to the longitudinal axis 317.

Figure 20A:
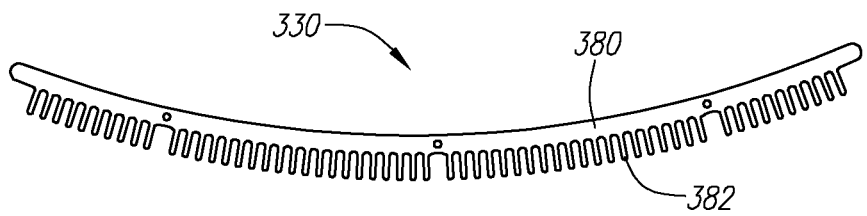
FIGS. 20A-20D show exemplary embodiments of baleen elements that may be included in the gasket member of FIGS. 17-19.
Figure 20B:
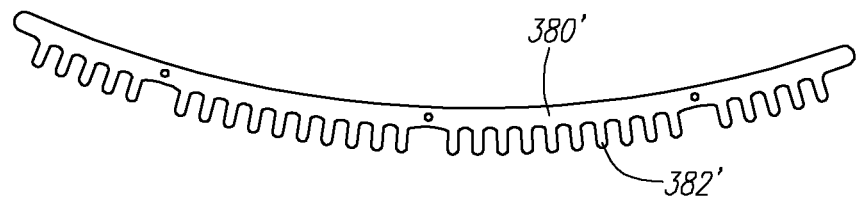
Figure 20C:
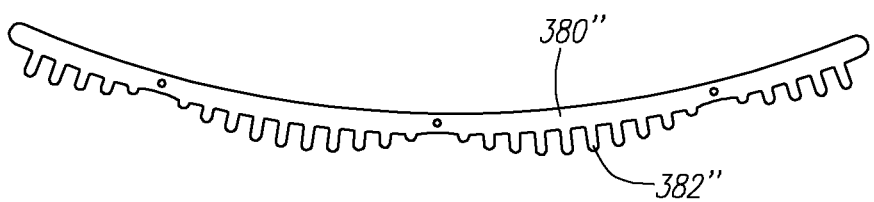
Figure 20D:
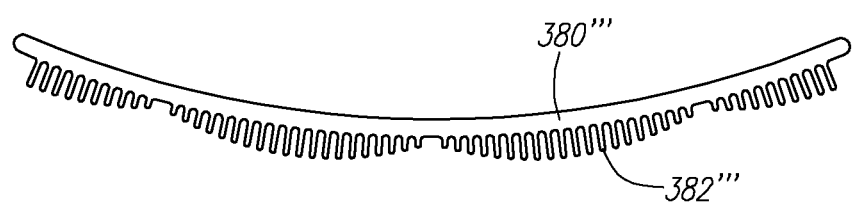

The baleen element 330 may be formed from an elongate flat band having the fingers 382 formed therein, such as the baleen elements 330 shown in FIGS. 20A-20D. In FIGS. 20A and 20B, the fingers 382, 382' have substantially uniform lengths, while in FIGS. 20C and 20D, the fingers 382", 382' have varying lengths, e.g., defining undulations or lobes, which may correspond to a shape below a biological annulus within which the gasket member 318 may be implanted. In addition, the fingers 382,' 382" in FIGS. 20B and 20C are thicker than the fingers 382, 382' in FIGS. 20A and 20D, which may provide a greater outward bias to enhance billowing the fabric covering 336 outwardly.

The baleen element 330 may be formed from a relatively thin band of mylar, polyester, or other polymer, an elastic or superelastic alloy, such as Nitinol, and the like, from which the base 380 and fingers 382 may be cut, e.g., by die-cutting, laser-cutting, and the like. In exemplary embodiments, the band (and consequently, the baleen element 330) may have a thickness between about 0.002 and 0.010 inch (0.05-0.25 mm). After the baleen element 330 is formed, the base 380 may have a width, e.g., between about 0.01-0.08 inch (0.25-2.0 mm), and the fingers 382 may have lengths, e.g., between about 0.01-0.08 inch (0.25-2.0 mm), and widths between about 0.01-0.04 inch (0.25-1.0 mm). The flat band may define a curve, e.g., such that when the band is rolled and its ends attached together, the base 380 and/or fingers 382 may be tapered to define a frusto-conical shape, as described above. The ends of the band may be attached together by ultrasonic welding, adhesives, and the like. Alternatively, the baleen element 330 may be molded or otherwise formed as a continuous piece in the frusto-conical shape.

Figure 19:
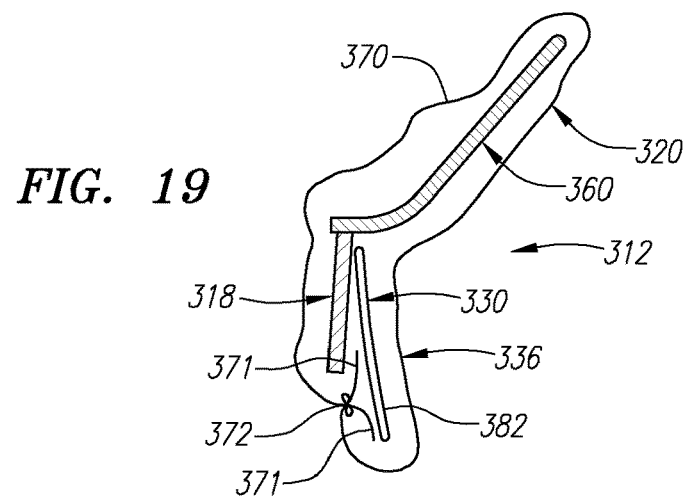
FIG. 19 is a cross-section of the gasket member of FIG. 17A, taken along line 19-19.

Turning to FIG. 19, a fabric covering 336 may be provided around the annular ring 318 and the baleen element 330, and a fabric covering 370 may be provided around the flexible core 360. As shown, the fabric covering 336, 370 may be a single piece of fabric that may be wrapped around the components of the gasket member 312, with any loose ends or edges 371 of the fabric secured together, e.g., by sutures 372, and/or by adhesives, other connectors (not shown), and the like. Alternatively, multiple pieces of fabric may be used, if desired. Optionally, the fabric covering 336, 370 may be fixed relative to one or more locations of the components of the gasket member 312 (e.g., the annular member 318, the flexible core 360, and/or the baleen element 330), e.g., by one or more sutures delivered through the fabric covering 336, 370 and/or one or more openings in the components.

Because the fingers 382 of the baleen element 330 are biased or otherwise flared outwardly, the fingers 382 may direct the fabric covering 336 radially outwardly away from the annular ring 318, e.g., adjacent the lower edge 319b. Thereafter, the fabric covering 336 and fingers 382 may be compressed inwardly, e.g., towards or against the annular ring 318. When such compressive force is released, however, the fingers 382 may resiliently return outwardly, thereby directing the fabric covering 336 outwardly. This feature may enhance a seal between the fabric covering 336 and surrounding tissue, as explained further below.

Figure 21A:
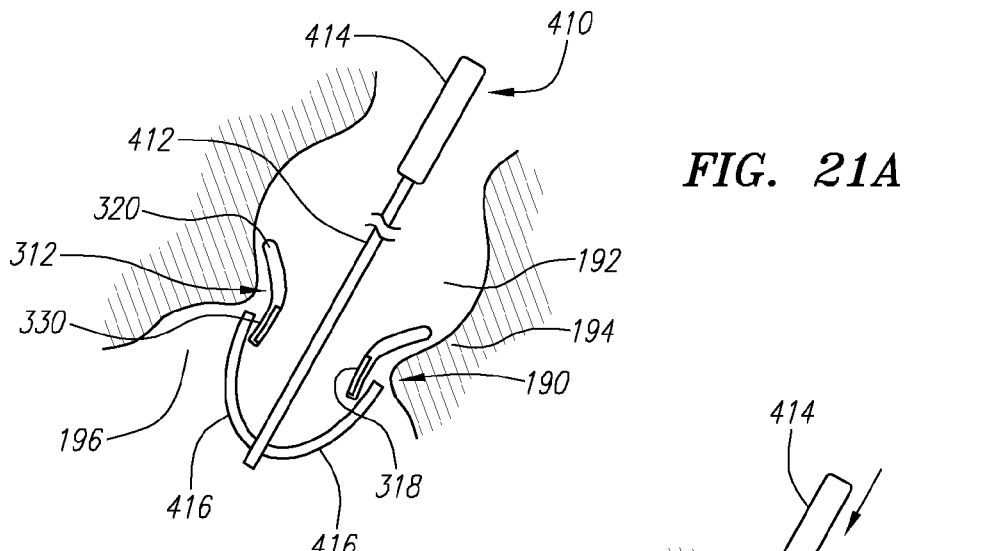
FIGS. 21A-21C are cross-sectional views of a heart, showing a method for implanting a gasket member within a biological annulus within the heart.
Figure 21B:
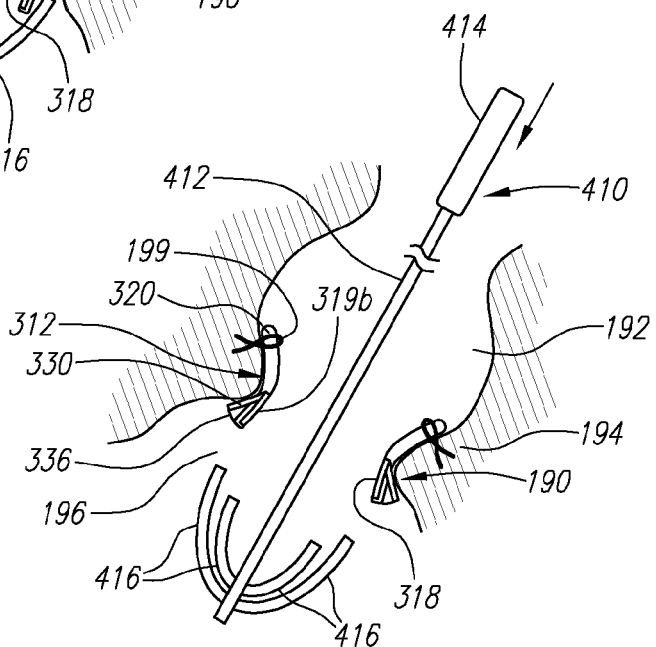
Figure 21C:
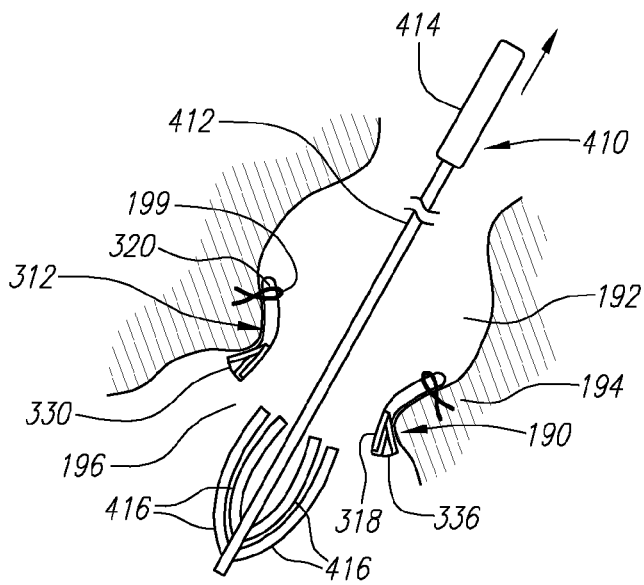

Turning to FIGS. 21A-21C, the gasket member 312 may be implanted within a biological annulus 190, e.g., to receive the crown 314 (not shown, see FIG. 17A) and thereby provide a heart valve prosthesis 310, similar to the previous embodiments. With the annular ring 318 and baleen element 330 contracted into a relatively smaller diameter (if the annular ring 318 is radially compressible), the gasket member 312 may be advanced into the annulus 190 using a delivery tool 410. The annular ring 318 may be advanced into the biological annulus 190 such that the sewing cuff 320 is disposed within the sinus cavity or other supra-annular space 192. A plurality of fasteners, such as clips 199, sutures, and the like (not shown) may be delivered through the sewing cuff 320 into the tissue 194 surrounding the sinus cavity 192. Exemplary tools and methods for delivering such fasteners are disclosed in co-pending application Ser. Nos. 10/681,700 and 11/004,445, filed Dec. 3, 2004, the entire disclosures of which are expressly incorporated by reference herein.

With continued reference to FIGS. 21A-21C, an expandable/contractable delivery tool 410 is shown that may be used for delivering the gasket member 312. As shown, the delivery tool 410 includes an elongate shaft 412 including a proximal handle 414 and a plurality of struts 416. The struts 416 may be movable between an expandable configuration (shown in FIGS. 21A and 21B) and a collapsed configuration (shown in FIG. 21C), using an actuator (not shown) on the proximal handle 412. Optionally, the struts 416 may be substantially transparent members that may be movable from a first transverse position (in the expandable position) to a second substantially axial position (in the collapsed configuration). Thus, the struts 416 may assume a shape similar to the struts of an umbrella that may be selectively opened and closed.

Initially, the struts 416 of the tool 410 may be expanded, and the gasket member 312 may be secured to the struts 416, e.g., by compressing the annular ring 318 (if compressible), and/or the baleen element 330 and fabric covering 336 towards the annular ring 318 between the struts 416. In this configuration, the struts 416 may substantially minimize a cross-section of the gasket member 312 below the sewing cuff 320, i.e., the size of the annular ring 318 and fabric covering 336, which may facilitate insertion of the gasket member 312 into the biological annulus 190. The gasket member 312 may be releasably secured to the tool 410 simply by friction or interference fit between the struts 416 and the gasket member 312. Alternatively, the struts 416 and/or gasket member 312 may include interlocking elements (not shown) for releasably securing the gasket member 312 to the struts 416.

As shown in FIG. 21A, the gasket member 312 may be advanced into the patient's body until the annular ring 318 extends at least partially into the biological annulus 190, similar to the previous embodiments. In one embodiment, the annular ring 218 may extend entirely through the biological annulus, with the lower edge 319b of the annular ring 318 extending into the sub-annular space 196 below the biological annulus 190. The sewing cuff 320 may contact the tissue 194 within the sinus cavity or supra-annular space 192 above the biological annulus 190. The sewing cuff 320 and/or annular ring 318 may substantially engage the surrounding tissue, such that, when the tool 410 is advanced further distally, the gasket member 312 may be released from the struts 416, as shown in FIG. 21B. Optionally, if the struts 416 and/or gasket member 312 include interlocking elements, the struts 416 may be expanded further to disengage the interlocking elements and/or otherwise release the gasket member 312. Finally, as shown in FIG. 21C, the struts 416 may be collapsed, and the tool 410 withdrawn from the biological annulus 190 and the patient's body.

When the gasket member 312 is released, the annular ring 318 may resiliently expand within the biological annulus 190, e.g., to dilate or otherwise open the biological annulus 190. In addition, as shown in FIGS. 21B and 21C, the baleen element 330 may resiliently expand outwardly, thereby directing the fabric covering 336 outwardly against tissue surrounding the sub-annular space 196. The baleen element 330 may cause the fabric covering 336 to billow outwardly to enhance a seal between the gasket member 312 and the surrounding tissue. Because of the relatively thin, flexible nature of the baleen element 330, the gasket member 312 may be removed, if desired, and the baleen element 330 may create minimal resistance. Thus, the baleen element 330 may not enhance anchoring the gasket member 312 relative to the biological annulus 190, but, instead, may enhance billowing or other shaping of the fabric covering 336, which may enhance apposition and/or sealing against the surrounding tissue.

Optionally, a dilation tool (not shown) may be advanced into the gasket member 312 after removing the tool 410, and expanded to forcibly expand the annular ring 318 within the biological annulus, if desired, similar to the previous embodiments. If the sewing cuff 320 is restrained by the delivery tool, the sewing cuff 320 may be released to allow the sewing cuff 320 to contact the surrounding tissue, e.g., before or while releasing the annular ring 318. Because of the flexible and/or conformable nature of the core 360, the sewing cuff 320 may at least partially conform or even substantially adopt the shape of the surrounding tissue 194. If the sewing cuff 320 includes an ear 368, the gasket member 312 may be angularly aligned in a predetermined manner during advancement into the biological annulus 190, i.e., before the gasket member 312 is released from the tool 410.

With the annular member 318 and sewing cuff 330 in place, a plurality of fasteners 199 may be directed through the sewing cuff 320 into the surrounding tissue 194 to secure the gasket member 112 relative to the biological annulus 190. The fasteners 199 may be delivered before the gasket member 312 is released from the tool 410, e.g., thereby anchoring the gasket member 312, which may facilitate releasing the gasket member 312 from the struts 416. Alternatively, the fasteners 199 may be delivered once the gasket member 312 is released and/or after the tool 410 is removed from the patient's body.

Figure 17A:
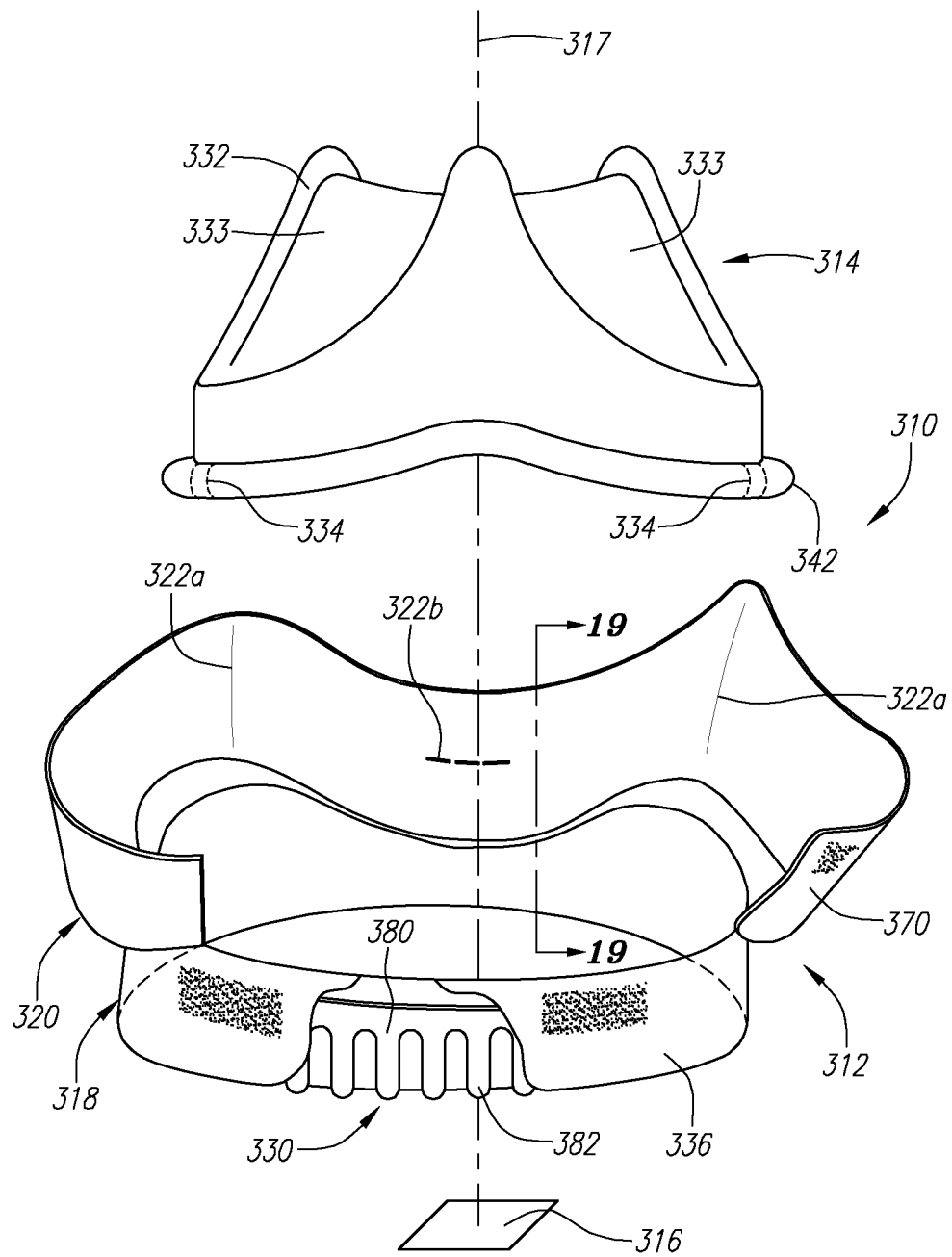
FIG. 17A is a partially cut-away perspective view of another embodiment of a heart valve assembly, including a gasket member and a valve member.
Figure 17B:
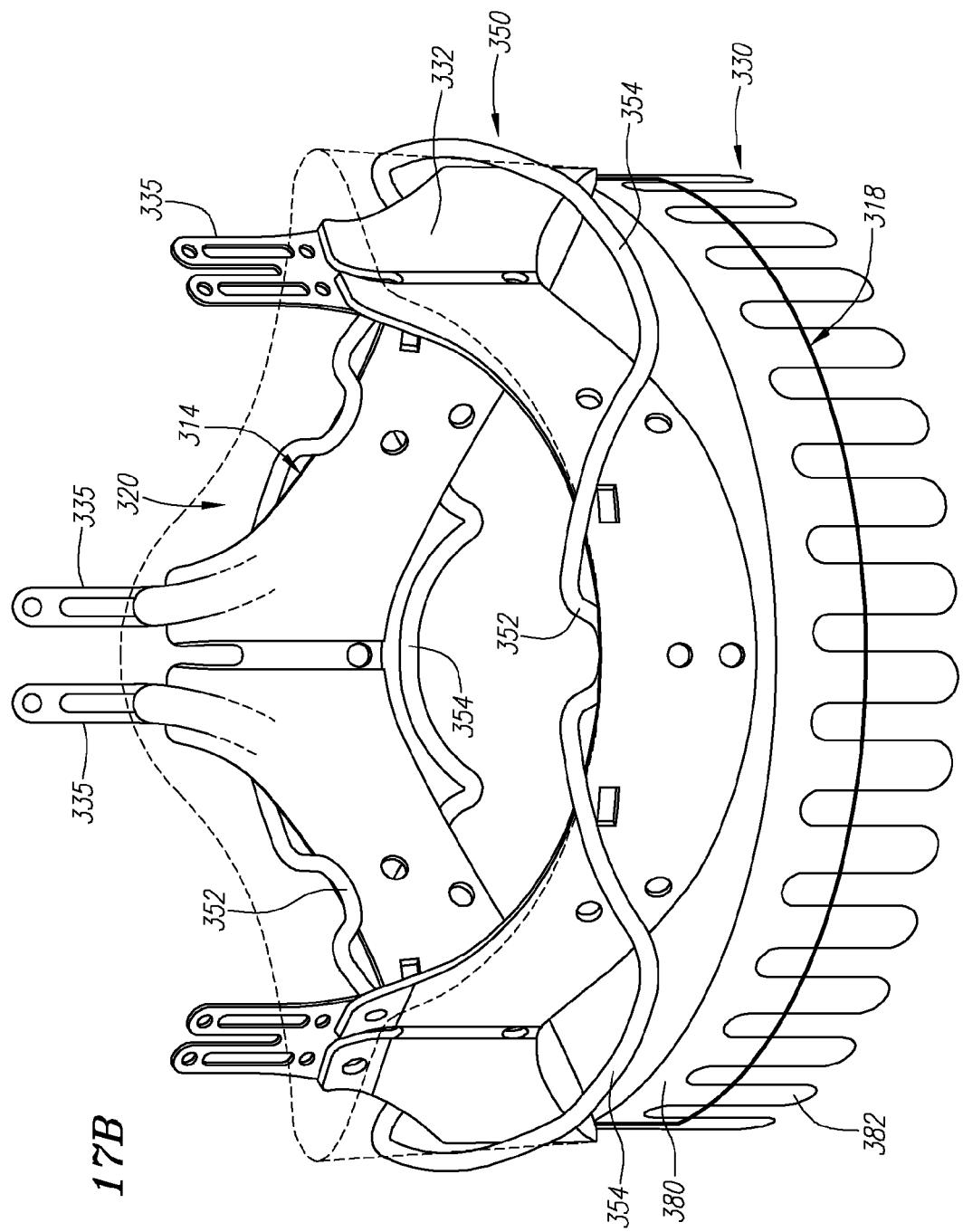
FIG. 17B is a perspective view of the heart valve assembly of FIG. 17A, with the valve member secured to the gasket member and with the fabric covering removed for clarity.

With additional reference to FIGS. 17A and 17B, the crown 314 may then be advanced into the sinus cavity 192, e.g. using another delivery tool or the same tool used to deliver the gasket member 312 (not shown). Optionally, the crown 314 may be angularly aligned with the gasket member 312, e.g., with the aid of one or more markers. For example, as shown in FIG. 17A, the gasket member 312 may include commissure markers 322a and/or nadir markers 322b, e.g., one or more sutures or other stitches, ink or dye indicators, and the like, that may be provided on desired locations of the sewing cuff 320 to facilitate orienting the gasket member 312 during insertion. The crown 314 may also include markers 334, e.g., on a flexible skirt 342 extending radially outwardly from the crown 314. As shown, the markers 334 may be located on the nadir of the crown 314, such that the markers 334 may be aligned with the nadir markers 322b on the gasket member 312 to angularly orient the crown 314 before being secured to the gasket member 312.

If the gasket member 312 includes the clip 350, the crown 314 may be advanced towards the gasket member 312, and tilted such that the frame 332 of the crown 314 may be received under two of the tabs 352 of the clip 350. The crown 314 may then be forced down into a planar orientation, causing the final tab 352 to be deflected outwardly until the frame 332 passes under the final tab 352. Alternatively, a tool, such as a hemostat, a suture line, or specialized valve holder (not shown) may be used to deflect the final tab 352 sufficiently such that the frame 332 may be received thereunder, thereby securing the frame to the clip 350.

In alternative embodiments, other materials and/or methods may be used for securing the crown 314 to the gasket member 312, such as those described elsewhere herein. For example, one or more clips or other fasteners (not shown) may be directed through the crown 314 and the sewing cuff 320 into surrounding tissue, as described above. For example, if the crown 314 includes a flexible skirt 342, the fasteners may be directed through the skirt 342 and the sewing cuff 320 substantially simultaneously. The fasteners may be spaced about the circumference of the crown 314, for example, e.g., at locations adjacent the nadir markers 334, thereby securing the crown 314 and/or enhancing a seal between the crown 314 and the sewing cuff 320.

Figure 17C:
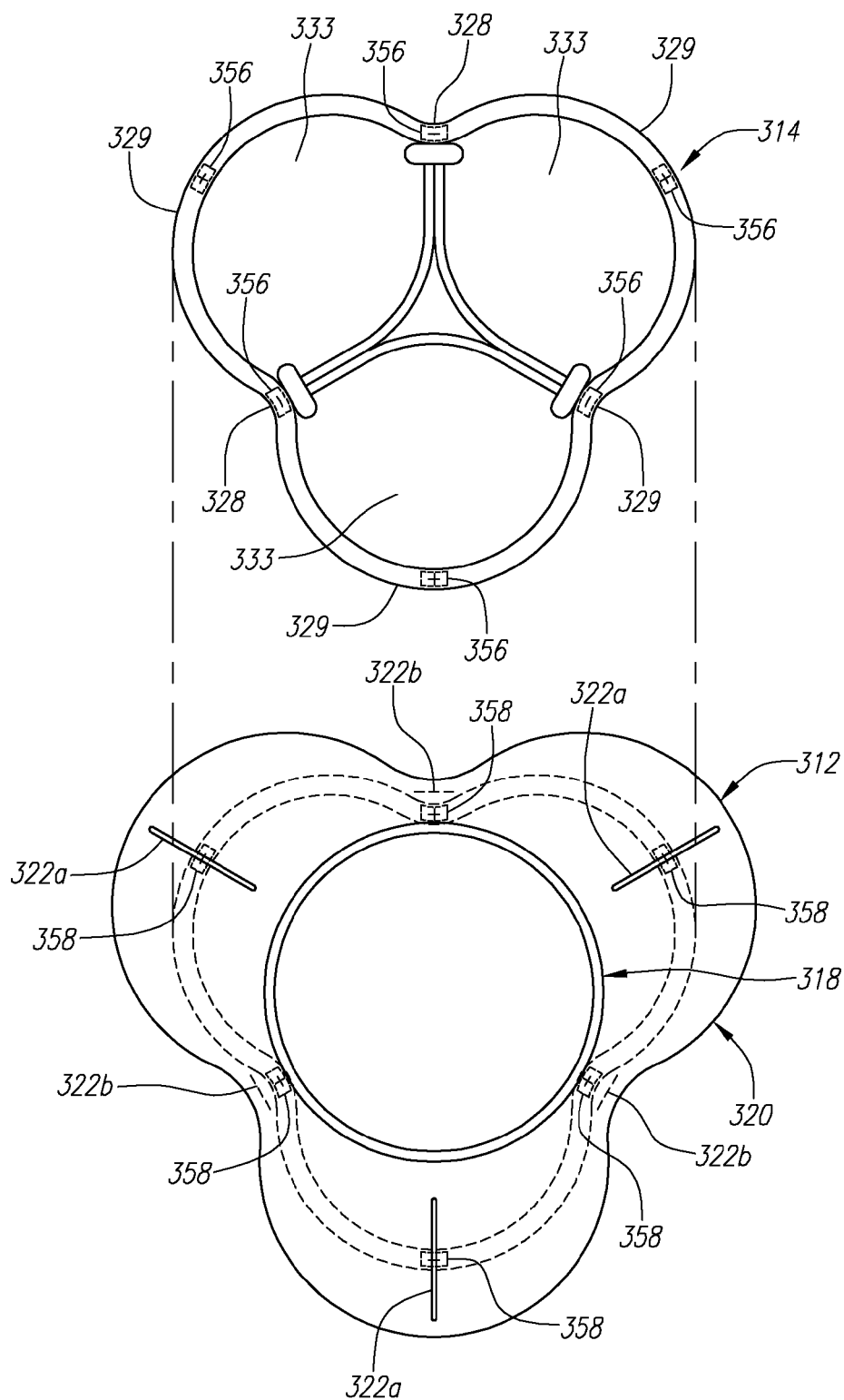
FIG. 17C is a top view of the valve member and gasket member of FIGS. 17A and 17B, including magnets for securing the valve member to the gasket member in a predetermined angular orientation.

Alternatively or in addition, one or more magnets (not shown) may be provided on the crown 314 and gasket member 312 (e.g., on the sewing cuff 320), similar to those disclosed in application Ser. No. 327,821, incorporated by reference above. The magnets may bias the crown 314 into a desired orientation relative to the gasket member 312, e.g., by arranging the polarity of the magnets about the circumference of the crown 314 and gasket member 312. For example, as shown in FIG. 17C, the crown member 314 may include a magnet 356 at each lobe 329 and cusp 328, e.g., providing six magnets 356 substantially evenly distributed about the circumference of a tri-lobular crown 314. The polarity of the magnets 356 at the lobes 329 may be reversed (e.g., negative) compared to the magnets 356 at the cusps 328 (e.g., positive). Thus, the polarities of the magnets 356 may alternate between positive and negative about the circumference of the crown member 314.

Similarly, the gasket member 312 may include magnets 358, e.g., substantially evenly disposed about the circumference of the sewing cuff 320. The magnets 358 may be disposed at locations corresponding to the desired orientation of the crown member 314 relative to the gasket member 312, e.g., at regions corresponding to the commissures and nadirs of the sinus cavity (not shown) into which the gasket member 312 is to be implanted. The polarities of the magnets 358 on the gasket member 312 may be alternated, similar to the magnets on the crown 314, thereby biasing the crown 314 to a predetermined angular orientation relative to the gasket member 312. For example, the magnets 358 adjacent markers 322a may be oriented with a negative polarity and the magnets 358 adjacent markers 322b may be oriented with a negative polarity. In this configuration, the magnets 356 on the crown member 314 may be attracted to the magnets 358 on the gasket member 312 with the opposite polarity, thereby automatically orienting the crown member 314 such that the lobes 329 overly the markers 322a and the cusps 328 overly the markers 322b. Other configurations and/or arrangements of magnets may be provided, e.g., such that the crown member 314 is automatically secured to the gasket member 312 in a desired angular orientation, e.g., to orient the crown member 314 within the sinus cavity in a desired orientation.

Turning to FIGS. 22 and 23, in another embodiment, a heart valve assembly 510 is shown that includes a plurality of retainer elements 550 that may be used to secure a crown 514 to a gasket member 512. The crown 514 and gasket member 512 may include any of the embodiments described elsewhere herein, except that the gasket member 512 includes a plurality of retainer elements 550 that are shown more particularly in FIGS. 24A-25B.

Turning to FIG. 24A, each retainer element 550 includes an enlarged base 552, and a tubular section 554 extending from the base 554. The tubular section 554 may include a plurality of slots 556 formed therein, allowing the tubular section 554 to buckle in a desired manner. In one embodiment shown in FIG. 25A, the slots 556 may be laser-cut, or otherwise cut in a vertical pattern extending around the tubular section 554. Alternatively, as shown in FIG. 25B, the slots 556' may be cut in a diagonal pattern extending around the tubular section 554.'

An actuator 560 may be provided for causing each retainer element 550 to buckle in a desired manner at the slots 556. For example, a pull wire 562 may be provided in each tubular section 554 that is attached to the base 552 or otherwise below the slots 556. A hypotube or other element 564 having substantial column strength may be provided around or adjacent the pull wire 562. The hypotube 564 may include a distal end 566 that may engage the tubular section 554 such that the base 552 may be moved while the tubular section 554 above the slots 556 may remain substantially stationary.

Returning to FIGS. 22 and 23, the retainer elements 550 may be secured to the gasket member 512, e.g., to a sewing cuff 520 extending radially from an annular member 518. For example, the enlarged bases 552 may be embedded within the sewing cuff 520 such that the tubular sections 554 extend through the sewing cuff 520. Alternatively, the bases 552 may be secured to an outer surface of the sewing cuff 520, e.g., using one or more sutures or other fasteners, adhesives, ultrasonic welding, and the like.

Each of the actuators 560 may extend upwardly from the gasket member 512, terminating in a handle 568 on the pull wire 562 that extends beyond the hypotube 564, best seen in FIG. 23. As shown in FIG. 22, the crown 514 may include a plurality of receiver elements 538, e.g., openings or tubular elements secured to the skirt 542, frame, or fabric covering. Exemplary receiver elements 538 that may be provided on the crown 514 are disclosed in application Ser. No. 10/765,725, incorporated by reference above. The receiver elements 538 may receive the actuators 560 therethrough, such that the crown 514 may be advanced down the actuators 560 until disposed against or adjacent the gasket member 512, e.g., in a desired angular orientation.

With the crown 514 disposed against the gasket member 512 (e.g., as shown in FIG. 24C), the actuators 560 may be activated to expand the retainer elements 550 to secure the crown 514 to the gasket member 512. Returning to FIGS. 24A and 24B, the pull wires 562 may be pulled using the handles 568 while the hypotubes 564 restrain the tubular sections 554 of the retainer elements 550 from moving. This compressive force causes the tubular sections 554 to buckle at the slots 556, thereby capturing the receiver elements 538 between the buckled tubular sections 554 and the enlarged bases 552, as shown in FIG. 24C. The pull wires 562 may include a weakened joint (not shown) adjacent the enlarged bases 552 such that additional force on the pull wires 562 causes the weakened joints to break, thereby allowing the pull wires 562 and hypotubes 564 to be removed from the patient's body, leaving the crown 514 secured to the gasket member 512.

Figure 26A:
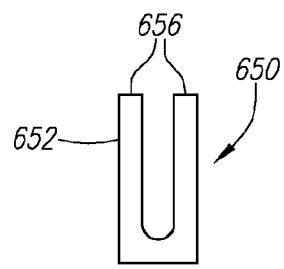
FIGS. 26A and 26B are front and side views, respectively, of a spring element for making a latch.
Figure 26B:
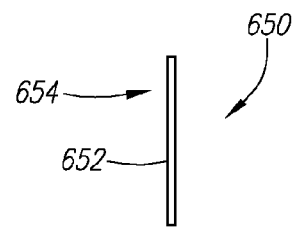
Figure 27A:
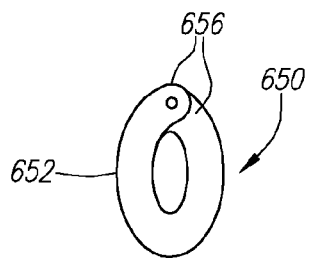
FIGS. 27A and 27B are front and side views, respectively, of the spring element of FIGS. 26A and 26B, with ends of the spring element attached together to create a two-position latch.
Figure 27B:
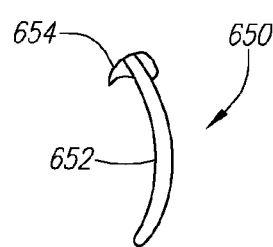

Turning to FIGS. 26A-28C, yet another embodiment of a connector 650 is shown that may be used to secure a crown or other valve member 614 to a gasket member 612. As shown, the connector 650 may be a two-position latch 652 including a hook 654 thereon. As shown in FIGS. 26A and 26B, the latch 652 may be a substantially flat clip including two prongs 656, the ends of which may be overlapped and attached to one another, e.g., by spot welding, riveting, bonding with adhesives, and the like, as shown in FIGS. 27A and 27B. A hook 654 or other catch mechanism may be provided on one end, e.g., adjacent the overlapped ends.

Figure 28A:
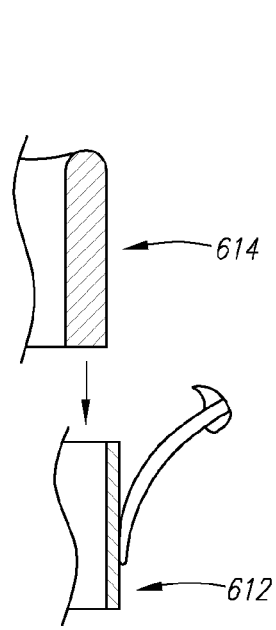
FIGS. 28A-28C are details of the two-position latch of FIGS. 27A and 27B being used to secure a valve member to a gasket member.
Figure 28B:
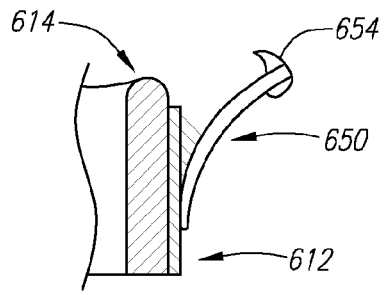
Figure 28C:
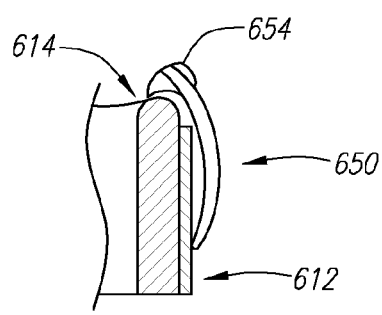

Turning to FIGS. 28A-28C, the resulting latch 652 may be biased to move between an open position (shown in FIGS. 28A and 28B) and a closed position (shown in FIG. 28C), similar to a spring hairclip. A plurality of latches 652 (only one shown) may be attached about a circumference of gasket member 612, which may be similar to any of the embodiments described herein, such that the hooks 654 extend above a plane defined generally by the gasket member 612. A crown 614, which may be any of the embodiments described herein, may be directed against the gasket member 612, as shown in FIG. 28B, whereupon the latches 652 may be moved to the closed position, as shown in FIG. 28C, thereby securing the crown 614 beneath the hooks 654.

Figure 29A:
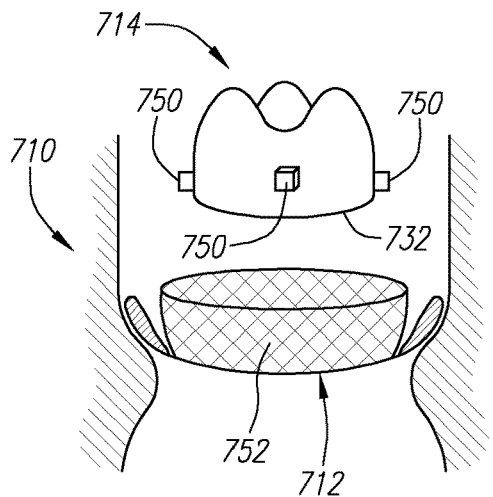
FIGS. 29A and 29B are side views of heart valve assemblies that include a valve member with protrusions that may engage a portion of a gasket member.

Turning to FIG. 29A, yet another alternative embodiment of a heart valve assembly 710 is shown that includes a gasket member 712 and crown 714, which may be similar to any of the embodiments described herein. As shown, the crown 714 may include a plurality of protrusions 750 extending radially outwardly from a frame 732 of the crown 714. The gasket member 712 may include a wire mesh or other lattice 752 on an interior surface of the gasket member 712. When the crown 714 is inserted into the gasket member 712 and rotated within a plane generally defined by the gasket member 712, the protrusions 750 may interlock with the mesh 752 to secure the crown 714 relative to the gasket member 714. For example, if the mesh 752 includes a plurality of interwoven diagonal threads, wires, or other filaments, rotation of the crown 714 with the protrusions 750 interlocked with the mesh 752 may cause the mesh to contract radially and/or shorten vertically, thereby tightening the mesh 752 around the crown 714. Thus, the mesh 752 may create a substantial interference fit around the crown 714 that may enhance securing the crown 714 relative to the gasket member 712.

Figure 29B:
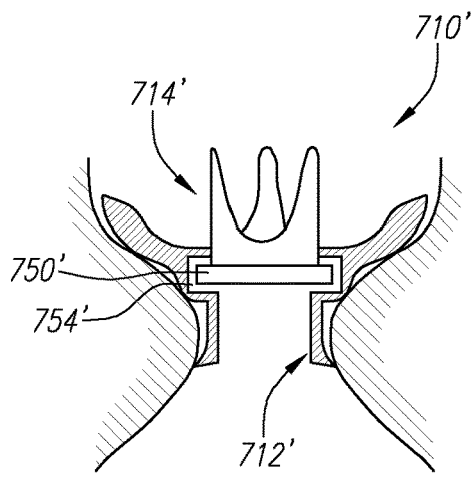

Alternatively, as shown in FIG. 29B, the gasket member 712' may include an annular groove 754' along an interior surface thereof. The crown 714' may include one or more protrusions 750' that may be received in the groove 754' to secure the crown 714' to the gasket member 712.' For example, the protrusion(s) 750' may include ramped edges (not shown), allowing the protrusion(s) 750' to be directed into the groove 754' by rotating the crown 714' relative to the gasket member 712.' This action may direct a portion of the gasket member 712' radially outwardly sufficiently to allow the protrusion(s) 750' to enter and be captured within the groove 754.'

Alternatively, other interlocking rings, e.g., including one or more annular protrusions and/or grooves (not shown) may be provided that facilitate securing a crown to a gasket member. Optionally, such interlocking rings may be at least partially covered with fabric to allow tissue ingrowth and/or may be sprayed or otherwise coated with a matrix that enhances tissue ingrowth. In another option, the interlocking rings or the protrusion(s) and/or groove(s) may be formed from different color materials that together change color in appearance when properly interlocked. The interlocking rings may be substantially permanently or removably attached to the crown and/or gasket member, e.g., using welding, adhesives, sutures and/or other connectors.

Figure 30A:
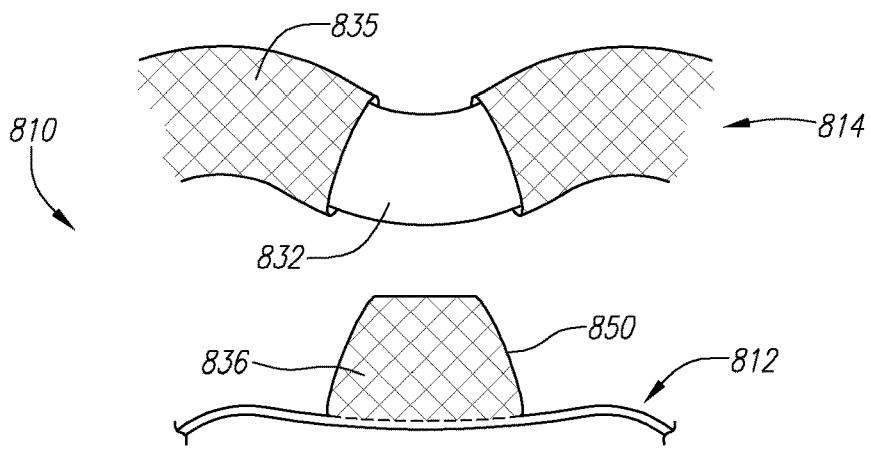
FIG. 30A is a detail of another embodiment of a heart valve assembly, including a latch on a gasket member for engaging a frame of a valve member.

Turning to FIGS. 30A and 20B, still another embodiment of a heart valve assembly 810 is shown that includes a gasket member 812 and a valve member 814, which may be similar to any of the other embodiments described herein. In this embodiment, the gasket member 812 includes one or more latches 850, preferably a plurality of latches (not shown) disposed around the circumference of the gasket member 812. The latch(es) 850 may be covered with fabric 836 or other matrix allowing tissue ingrowth. The valve member 814 includes a frame 832 that is also at least partially covered by fabric 835. As shown, the frame 832 is not covered with fabric at the location(s) corresponding to the latch(es) 850, thereby facilitating interlocking of the latch (es) 850 with the frame 832.

Figure 30B:
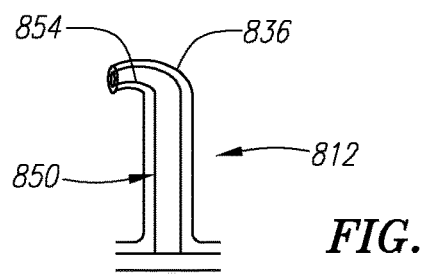
FIG. 30B is a side view of the latch of FIG. 30A.

As shown in FIG. 30B, the latch(es) 850 may include a hook 854 or other element for interlocking with the frame 832 of the valve member 814. The latch(es) 850 may include ramped or tapered upper end(s) (not shown), allowing the frame 832 to deflect the latch(es) 850 at least partially outwardly as the frame 832 is directed towards the gasket member 812. Once the frame 832 passes below the hook(s)

854, the latch(es) 850 may resiliently return inwardly, thereby securing the frame 832 relative to the gasket member 812.

Figure 31A:
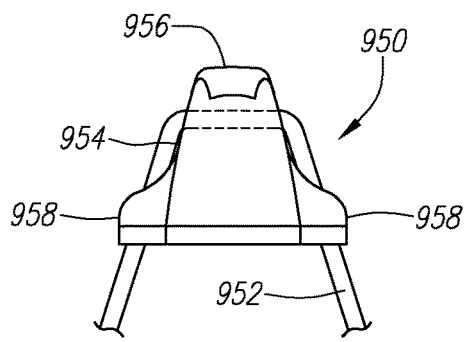
FIGS. 31A and 31B are front and side views, respectively, of a pivotable latch in an open position.
Figure 31B:
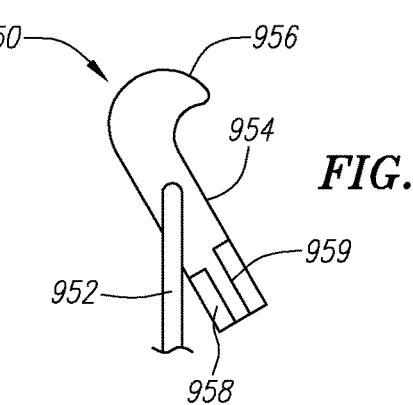
Figure 32A:
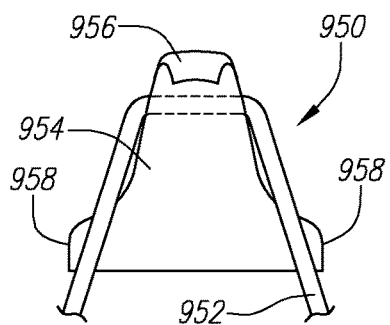
FIGS. 32A and 32B are front and side views, respectively, of the latch of FIGS. 31A and 31B in a closed position.
Figure 32B:
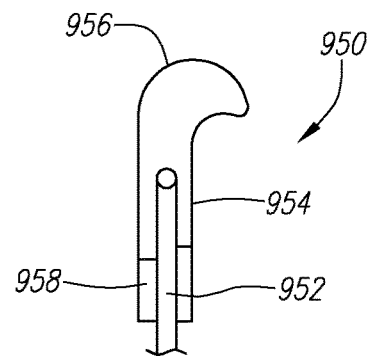
Figure 33:
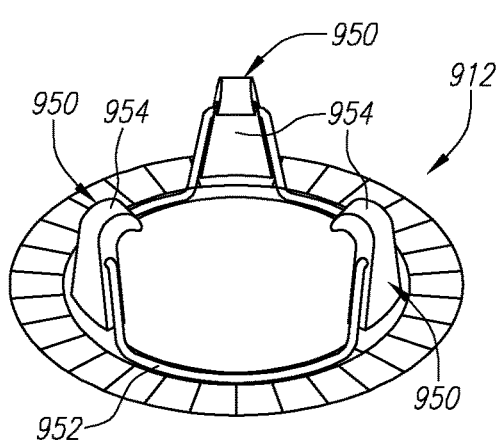
FIG. 33 is a perspective view of a gasket member, including a plurality of the latches shown in FIGS. 31A-32B.
Figure 34:
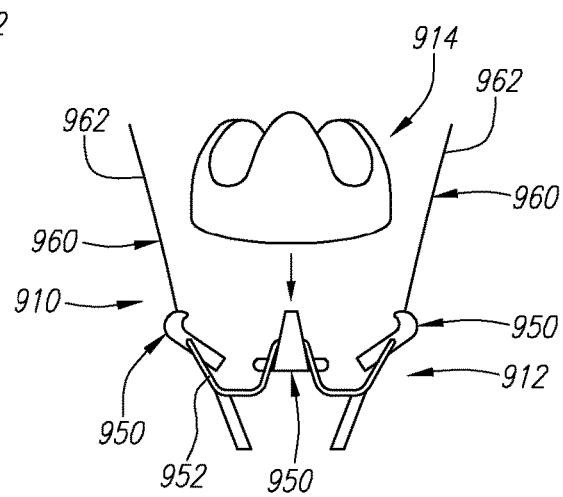
FIG. 34 is a partial cross-sectional side view of a heart valve assembly including the gasket member of FIG. 34 and a valve member.

Turning to FIGS. 31A-32B, yet another embodiment of a latch 950 is shown that may be used to secure a valve member 914 to a gasket member 912, such as that shown in FIGS. 33 and 34. Generally, the latch 950 includes a wire frame 952 to which a latch member 954 is pivotally attached. The latch member 954 includes a hook or other latch element 956 on an upper end, and a pair of ramped tabs 958 on a lower end thereof. The latch member 954 is pivotable between a transverse or open position, shown in FIGS. 31A and 31B, and a vertical or closed position, shown in FIGS. 32A and 322B.

In the open position, the ramped tabs 958 may be disposed in front of the wire frame 952, as shown in FIGS. 31A and 31B, such that the latch member 954 is free to pivot relative to the wire frame 952. If the latch member 954 is directed towards the vertical position, the tabs 958 may contact the wire frame 952, thereby resisting moving the latch member 954 further vertically. If additional force is applied, the ramped edges of the tabs 958 may cause the wire frame 952 to deflect outwardly, thereby allowing the tabs 958 to pass behind the wire frame 952, as shown in FIGS. 32A and 32B. Once the tabs 958 are disposed behind the wire frame 952, the wire frame 952 may resiliently return inwardly to engage the latch member 954. Optionally, the latch member 954 may include a groove 959 (shown in FIG. 31B) in one or both sides for receiving the wire frame 952 therein, thereby substantially locking the latch member 9544 in the closed position. The rigidity of the wire frame 952 may be selected to provide sufficient softness to allow the tabs 958 to pass behind the wire frame 952 with relative ease, yet the wire frame 952 may be sufficiently resilient to return inwardly to secure the latch member 954 in the closed position.

Turning to FIG. 33, a gasket member 912 is shown, which may be similar to any of the embodiments described herein. As shown, the gasket member 912 includes a wire frame 952 that extends around a circumference of the gasket member 912, and to which are pivotably attached a plurality of latch member 954, thereby providing latches 950. Although three latches 950 are shown for exemplary purposes, it will be appreciated that more or fewer latches 950 may be provided, as desired. The wire frame 952 may be secured to the gasket member 912 by a fabric covering (not shown), similar to previous embodiments, and/or by one or more sutures or other connectors (also not shown). Although a single wire frame 952 is shown, it will be appreciated that a plurality of wire frames (not shown) may be provided instead, e.g., corresponding to one or more individual latches.

Turning to FIG. 34, the latches 950 may be used to secure a valve member 914, which may be similar to any of the embodiments described herein, to the gasket member 912 of FIG. 33. With the latches 950 in the open position, the valve member 914 may be advanced towards the gasket member 912. Once the valve member 914 is disposed below the edges of the latches 950, the latches 950 may be activated, thereby capturing a portion of the valve member 914 (e.g., the frame) below the hooks 956.

To activate the latches 950, an actuator 960 may be provided that is coupled to each of the latches 950 (only two shown in FIG. 34 for clarity). As shown, the actuator 960 includes a wire 962 coupled to the latch member 954, e.g., to the hook 956. The wire 962 may be detachably connected to the latch member 954, e.g., by a weakened region (not shown) that may break when a predetermined tensile force is applied to the wire 962. Thus, a first tensile force may be applied to the wires 962 to move the latches 950 from the open to the closed positions, and then, a second greater tensile force may be applied to break the wires 962 at the weakened region, whereupon the wires 962 may be removed.

Alternatively, the wire 962 may include two ends, one of which is looped through an opening in the latch member 954 (not shown). To activate each latch 950, both ends of the wire 962 may be grasped and pulled, thereby pulling the latch member 954 to the closed position. After the wire 962 is used to activate the latch 950, one end may be released and pulled through the opening in the latch member 954 to release and remove the wire 962. In yet a further alternative, the lower end of the latches 950 may be configured such that the valve member 914 contacts the lower ends directly, thereby directing the latches 950 to the closed position as the valve member 914 is directed against the gasket member 912.

Figure 35A:
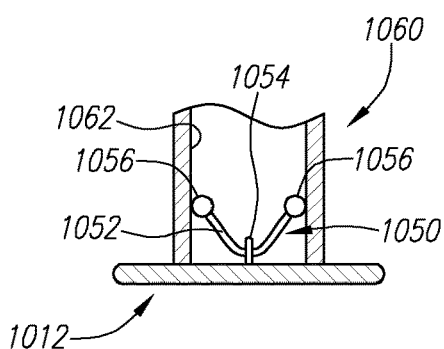
FIGS. 35A and 35B are cross-sectional views of an expandable latch in compressed and expanded configurations, respectively.
Figure 35B:
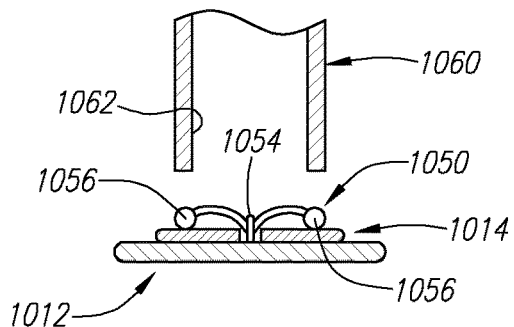
Figure 36A:
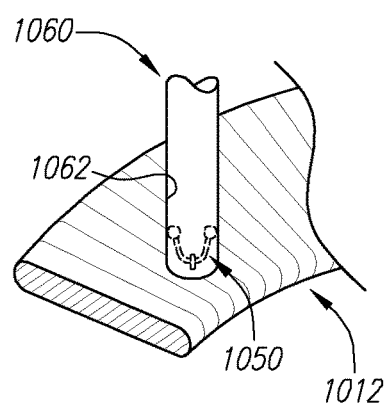
FIGS. 36A-36C are perspective details of a heart valve assembly including a valve member being secured to a gasket member using the latch of FIGS. 35A and 35B.
Figure 36B:
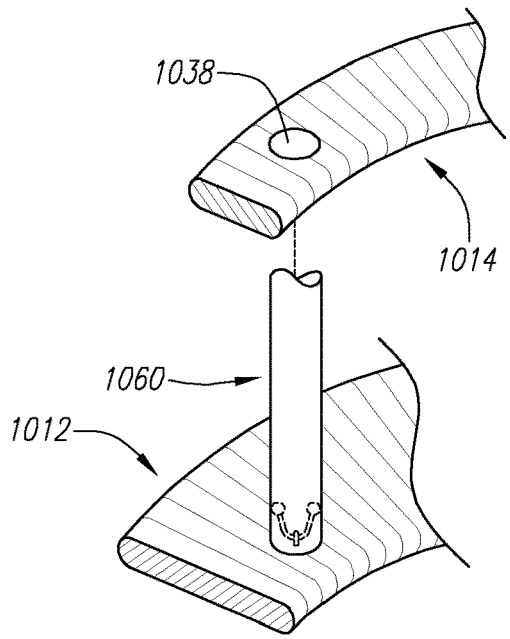
Figure 36C:
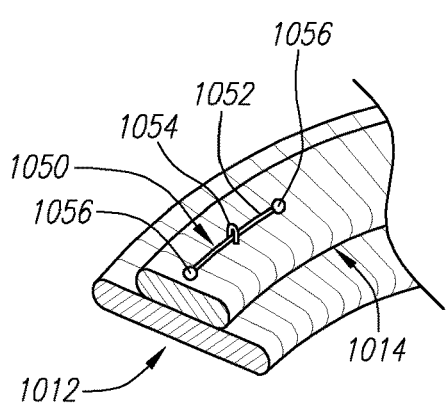

Turning to FIGS. 35A and 35B, still another embodiment of a latch 1050 is shown that may be used to secure a valve member 1014 to a gasket member 1012, as shown in FIGS. 36A-36C. Generally, the latch 1050 includes a deformable latch element 1052 secured to the gasket member 1012, which may be similar to any of the embodiments described herein, at an intermediate region of the latch element, e.g., by a suture 1054 or other connector (not shown). The latch element 1052 includes opposing ends 1056 that may be deformed about the intermediate region from a substantially planar or closed position, shown in FIGS. 35B and 36C, and a bent or open position, shown in FIGS. 35A and 36A.

In the embodiment shown, the latch element 1052 includes an elongate rod, tube, or other wire, e.g., formed from Nitinol or other elastic or superelastic material, having enlarged balls on the ends 1056, thereby providing a latch element similar to a "dog bone" or "cuff-link." The wire may be bent about an intermediate region, e.g., by pulling the ends 1056 upwardly away from the gasket member 10012. When the ends 1056 are released, the latch element 1052 may substantially straighten towards the closed position shown in FIGS. 35B and 36C. In one embodiment, the latch element 1052 may be formed from a plurality of sections of wires with ends connected by ball welds, which may reduce the strain experienced by each section of wire as compared to using a single length of wire for the latch element 1052.

Figure 37A:
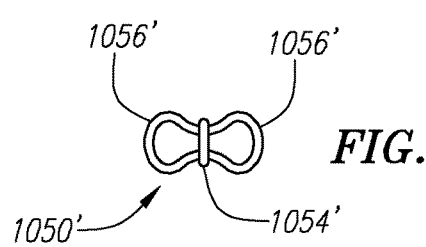
FIGS. 37A and 37B are top and side views of an alternative embodiment of an expandable latch.
Figure 37B:
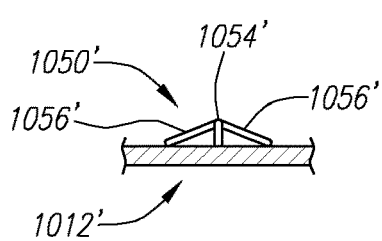

In another embodiment, shown in FIGS. 37A and 37B, the latch 1050' may include a loop latch element 1052' secured by a suture 1054.' The latch element 1052,' which may include an elastic or superelastic material, e.g., Nitinol, may be formed from a wire that is looped and whose ends are attached together, e.g., by welding, interference fit, mechanical connectors, bonding with adhesives, and the like, to provide a bow-tie shape. Alternatively, the latch element 1052' may be formed by cutting a thin section off of a length of tubing to provide a ring having a diameter similar to the size of the loop. The ring may be deformed into the bow-tie shape and heat set, or otherwise treated to set the bow-tie shape, yet allow the latch element 1052' to bend. In another alternative, the latch element 1052' may be laser cut from a flat sheet, a ring, or a length of tubing, and formed and treated to provide the latch element 1052.' Similar to the latch 1050, the latch 1050' may be bent from a closed position, shown in FIG. 37B, to an open position, shown in FIG. 37A, by pulling upwardly on opposing ends 1056' of the latch member 1052.'

The latch element 1052 may be biased to the closed position, but may be resiliently deformed and retained in the open position, e.g., by a retaining element 1060. As shown in FIGS. 35A and 35A, the retaining element 1060 may be a tubular member, e.g., a section of substantially rigid hypotube, having a lumen 1062 for receiving the latch element 1052 therein in the open position. Because the latch element 1052 may be biased to return to the planar position, the ends 1056 of the latch element 1052 may bear against the inner wall of the retaining member 1060. As the retaining member 1060 is removed, as shown in FIG. 35B, the ends 1056 of the latch element 1052 may slide along the retaining member 1060 until released, whereupon the ends 1056 may return to the closed position.

Turning to FIGS. 36A-36C, during use, the gasket member 1012 may be introduced into and secured to the biological annulus (not shown), similar to the previous embodiments, with the retaining member(s) 1060 retaining the latch(es) 1050 in the open position. A valve member 1014, which may be similar to any of the embodiments described herein, may include a receiving element 1038 through which each retaining member 1060 may pass as the valve member 1014 is directed towards the gasket member 1012, as shown in FIG. 36B. Once the valve member 1014 is disposed adjacent the gasket member 1012, as shown in FIG. 36C, the retaining member 1060 may be withdrawn, releasing the latch 1050. The latch element 1052 may press downwardly on the valve member 1014, substantially securing the valve member 1014 to the gasket member 1012.

Turning to FIGS. 38A-39B, another spring latch 1150 is shown that may be used to secure a valve member 1114 to a gasket member 1112, which may include any of the embodiments described herein. Similar to the previous embodiment, the latch 1150 may be movable between a closed position, shown in FIG. 38B, and an open position, shown in FIG. 38A, and a retaining member 1160 may be provided that may constrain the latch 1150 in the open position. Unlike the previous embodiment, the latch 1150 includes a post 1152 and a loop 1154 that overlies and/or surrounds the post 1152 in the closed position, as best seen in FIG. 38B. The loop 1154 may be a length of wire formed into a loop whose loose ends are secured to the gasket member 1112. The wire may be formed from Nitinol or other elastic or superelastic material, such that the loop 1154 may be bent away from the post 1152 to the open position. The retaining member 1160 may include a lumen 1162 or other recess for receiving the loop 1154 in the open position, thereby constraining the loop 1154.

Turning to FIGS. 39A and 39C, during use, the gasket member 1112 may be introduced into and secured to the biological annulus (not shown), similar to the previous embodiments, with the retaining member(s) 1160 retaining the latch(es) 1150 in the open position. Although only a single latch 1150 and retaining member 1160 are shown, it will be appreciated that a plurality of latches 1150 may be provided around the circumference of the gasket member 1112, with each latch 1150 having a corresponding retaining member 1160. A valve member 1114 may include receiving elements 1138 (one shown) through which respective retaining members 1160 may pass as the valve member 1114 is directed towards the gasket member 1112, as shown in FIG. 39A. Once the valve member 1114 is disposed adjacent the gasket member 1112, as shown in FIG. 39B, the retaining member 1160 may be withdrawn, releasing the latch 1150. The loop 1154 may resiliently pivot to the closed position surrounding the post 1152, thereby substantially securing the valve member 1014 to the gasket member 1012.

Turning to FIGS. 40A-40B, another embodiment of a clip 1250 is shown that includes a plurality of transverse elements 1252 defining an opening 1254 therein. As shown, the clip 1250 includes four transverse elements 1252 defining a diamond shape, although it will be appreciated that other shapes, including fewer or additional transverse elements (not shown), may also be provided. The clip 1250 is compressible to a first position, i.e., wherein the clip 1250 is deformed inwardly in a generally horizontal direction, whereby the clip 1250 may elongate vertically, as best seen in FIG. 40A. The clip 1250 may be biased towards a second position, i.e., wherein the clip 1250 widens and shortens, as shown in FIG. 40B.

To constrain the clip 1250 in the first position, a retaining member 1260 may be provided, similar to the previous embodiments, that includes a lumen 1262 for receiving the clip 1250 therein. Unlike previous embodiments, the retaining member 1260 includes a slot 1264 at its lower end that may be aligned with the opening 1254 in the clip 1250, as shown in FIG. 40A. For example, with the slot 1264 aligned with the opening 1254, the clip 1250 may be compressed and inserted into the lumen 1262 of the retaining member 1260. Because of the bias of the clip 1250, the transverse elements 1252 may bear against the inner wall of the retaining member 1260, yet allow the clip 1250 to slide along the inner wall when the retaining member 1260 is withdrawn. Once released from the retaining member 1260, the clip 1250 may resiliently widen and shorten.

Turning to FIG. 41, a plurality of clips 1250 may be provided on a gasket member 1212, which may be similar to any of the embodiments described herein. Initially, the clips 1250 may be constrained within respective retaining elements 1260 (shown in phantom for clarity). The gasket member 1212 may be introduced and implanted within a biological annulus, similar to previous embodiments. Thereafter, a valve member 1214, which may be similar to any of the embodiments described herein, may be introduced and advanced towards the gasket member 1212. The valve member 1214 may include a plurality of buttons or catches 1238 disposed about a circumference of the valve member 1214, e.g., corresponding to locations of respective clips 1250 on the gasket member 1212. An alternative embodiment of a catch 1238' that may be provided on the valve member 1214' is shown in FIG. 43.

Turning to FIG. 42A, as the valve member 1214 is directed towards the gasket member 1212, the catch 1238 may be received in the slot 1264 of a respective retaining member 1260, thereby aligning the catch 1238 within the opening 1254 of the clip 1250. Once the catch 1238 is received in the opening 1254, the retaining member 1260 may be withdrawn, as shown in FIG. 42B, whereupon the clip 1250 may shorten, thereby capturing the catch 1238 therein. The resulting compressive force from the clip 1250 may direct the valve member 1214 further towards the gasket member 1212, thereby resisting the valve member 1214 being separated from the gasket member 1212.

Figure 44:
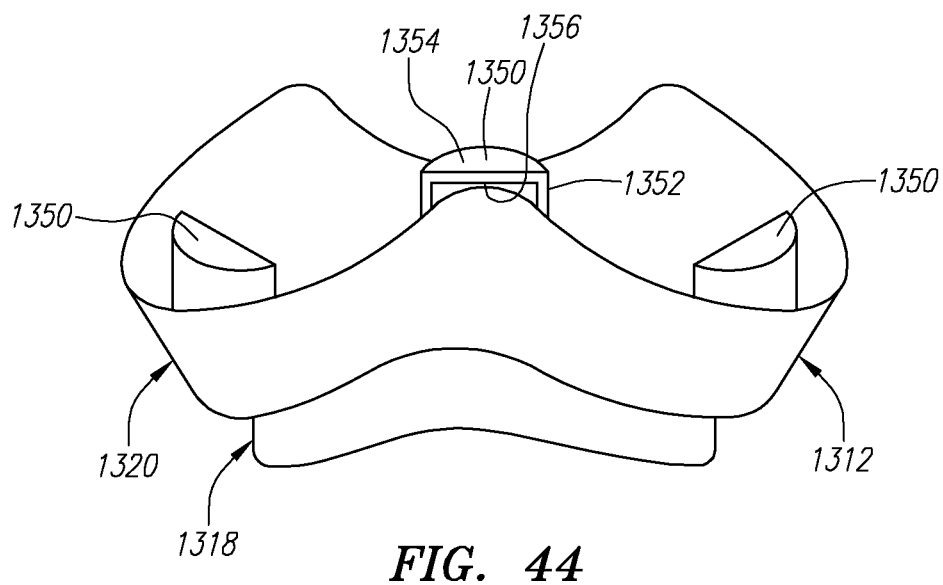
FIG. 44 is a perspective view of another embodiment of a gasket member that may be used to secure a valve member to a tissue annulus.
Figure 45:
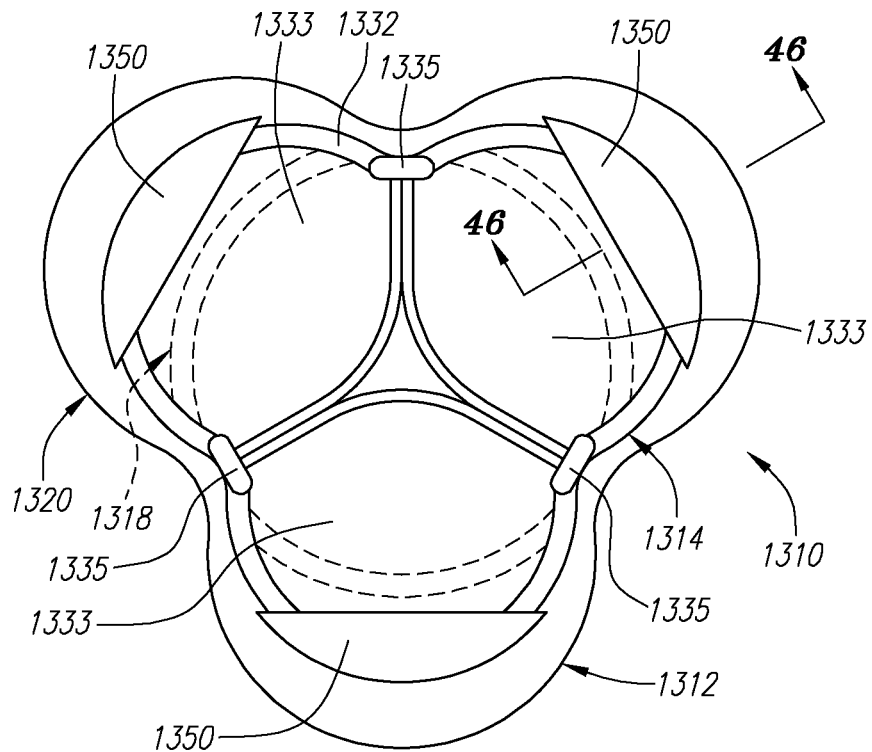
FIG. 45 is a top view of the gasket member of FIG. 44 with a valve member secured thereto to provide a prosthetic valve.
Figure 46:
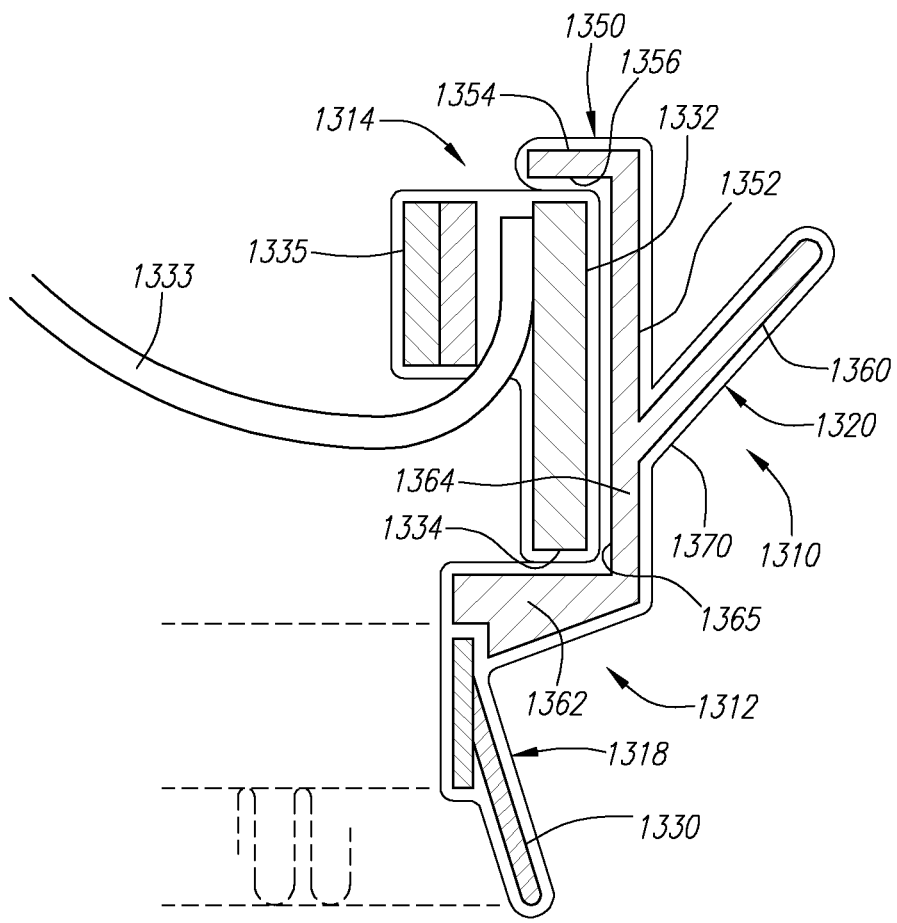
FIG. 46 is a cross-section of the prosthetic valve of FIG. 45, taken along line 46-46.

Turning to FIGS. 44-46, yet another embodiment of a heart valve assembly 1310 is shown that includes a gasket member 1312 and a crown 1314. Similar to the previous embodiments, the gasket member 1312 may include an annular ring 1318 and a sewing cuff or ring 1320. The sewing cuff 1320 may include a flexible core 1360 and a fabric covering 1370, similar to previous embodiments, and a baleen element 1330 may be provided between the annular member 1318 and fabric covering 1370, also similar to previous embodiments. The crown 1314 may include a frame 1332 and a plurality of leaflets 1333 carried by struts 1335, also similar to previous embodiments. In addition, similar to previous embodiments, the gasket member 1312 and/or crown 1314 may include one or more connectors for securing the crown 1314 relative to the gasket member 1312.

For example, as shown in FIGS. 44 and 46, the gasket member 1312 may include a plurality of pockets 1350 that capture or otherwise secure one or more regions of the crown 1314. As best seen in FIG. 46, each pocket 1350 may include an outer wall 1352 and a cover 1354, thereby defining a recess 1356. The pockets 1350 may be integrally formed with the core 1360 of the sewing cuff 1320, e.g., from a base 1362 of the core 1360. For example, the pockets 1350 and core 1360 may be molded or otherwise formed from silicone or other flexible or semi-rigid material. Alternatively, the pockets 1350 may be formed separately and attached to the base 1362, e.g., by bonding, heat fusion, interlocking connectors (not shown), and the like. The pockets 1350 may be sufficiently flexible to be directed radially outwardly, e.g., to facilitate receiving the valve member 1314 (as explained below), yet sufficiently resilient to return to its original position upon release.

During use, the gasket member 1312 may be implanted within a tissue annulus, similar to the methods and materials described elsewhere herein. The valve member 1314 may be introduced into the tissue annulus, e.g., into the sinus cavity above a native tissue valve site (not shown), with the frame 1332 angled diagonally relative to the gasket member 1312. The frame 1332 may be directed under the pockets 1350 such that a portion of the frame 1332 is received within the recesses 1356. For example, first two lobes of the valve member 1314 may be directed into two of the pockets 1350, which may cause the pockets 1350 to be deflected slightly to facilitate insertion. Then, the remaining pocket 1350 may be deflected outwardly, while the valve member 1314 is directed horizontally against the sewing cuff 1320 of the gasket member 1312. The deflected pocket 1350 may then be released such that the cover 1354 passes over the frame 1332 of the valve member 1314. Thus, the frame 1332 is secured within the recesses 1356 below the covers 1354.

Optionally, as shown in FIG. 46, the gasket member 1312 may include a rim 1364 that extends vertically from the base 1362, thereby at least partially defining a space 1365. A lower edge 1334 of the frame 1332 of the valve member 1314 may be received in the space 1365, e.g., similar to the embodiments described above. The frame 1332 may bear against the rim 1364, e.g., to provide an interference fit, thereby further securing the valve member 1314 relative to the gasket member 1312. Optionally, other connectors (not shown) may be provided in addition to or instead of the pockets 1350 and/or rim 1364.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A prosthetic heart valve for implantation at a biological annulus, the prosthetic heart valve comprising:
   a sealing member comprising an annular member, a fabric member, and a baleen element, the sealing member having a first diameter in a contracted state and a second diameter in an expanded state, the second diameter being greater than the first diameter, the fabric member covering at least a portion of the baleen element and at least a portion of the annular member, wherein, in the contracted state, the baleen element is compressed against the annular member and in the expanded state, an angle between the annular member and the baleen element increases such that the baleen element billows at least a portion of the fabric member outwardly away from the annular member as the sealing member transitions from the contracted state to the expanded state within the biological annulus; wherein the baleen element is positioned exterior with respect to the annular member in both the contracted and expanded states; the sealing member further having a lattice extending around a circumference of the annular member; and
   a valve member attached to the sealing member.

2. The prosthetic heart valve of claim 1, wherein the sealing member is penetrable by fasteners for securing the sealing member to tissue of the biological annulus.

3. The prosthetic heart valve of claim 1, wherein the sealing member has a multiple lobular shape corresponding to the shape of tissue of the biological annulus.

4. The prosthetic heart valve of claim 1, wherein the sealing member is resiliently conformable with a shape of the biological annulus such that at least one of a circumference and a taper of the sealing member change to accommodate to the shape of the biological annulus.

5. The prosthetic heart valve of claim 1, wherein the lattice comprises a plurality of ribs at least partially defining openings.

6. The prosthetic heart valve of claim 1, further comprising a core, wherein the lattice comprises a plurality of ribs extending from at least one of an upper surface and a lower surface of the core.

7. The prosthetic heart valve of claim 1, wherein the lattice has a plurality of enclosed openings that are completely open and free from any material.

8. The prosthetic heart valve of claim 1, wherein the lattice has a plurality of recesses in which a wall of core material is positioned.

9. The prosthetic heart valve of claim 8, wherein the lattice comprises a plurality of ribs extending from at least one of an upper surface and a lower surface of the annular member, the ribs being compressible for conforming to a shape of the valve member attached to the sealing member to enhance sealing between the valve member and the sealing member.

10. The prosthetic heart valve of claim 1, the baleen element comprising a plurality of finger elements for billowing at least a portion of the fabric member outwardly away from the annular member.

11. The prosthetic heart valve of claim 10, wherein the plurality of finger elements have varying lengths.

12. The prosthetic heart valve of claim 1, wherein the valve member is connected to the sealing member with at least one connector.

13. The prosthetic heart valve of claim 12, wherein the at least one connector comprises a clip.

14. The prosthetic heart valve of claim 12, wherein the at least one connector comprises a magnet.

15. A prosthetic heart valve for implantation in a biological annulus, the prosthetic heart valve comprising:
   an expandable sealing member comprising an annular ring and a sewing cuff extending from the annular ring, a fabric covering, and a baleen element, wherein fabric covering covers at least a portion of the baleen element, wherein in a contracted state, the baleen element is compressed against the annular member and in an expanded state, an angle between the annular member and the baleen element increases and an angle between the sewing cuff and the baleen element decreases such that the baleen element billows at least a portion of the fabric covering outwardly away from the annular ring as the sealing member transitions from the contracted state to the expanded state within the biological annulus; wherein the baleen element is positioned exterior with respect to the annular ring in both the contracted and expanded states; and a valve member attached to the expandable sealing member.

16. The prosthetic heart valve of claim 15, further comprising at least one connector for attaching the valve member to the expandable sealing member.

17. The prosthetic heart valve of claim 15, wherein the fabric covering also covers at least a portion of the annular ring.

18. The prosthetic heart valve of claim 15, wherein the baleen element comprises a plurality of finger elements for billowing at least a portion of the fabric covering outwardly away from the annular ring.

* * * * *